United States Patent
Ottoboni et al.

(10) Patent No.: US 9,694,079 B2
(45) Date of Patent: *Jul. 4, 2017

(54) LONG-ACTING POLYMERIC DELIVERY SYSTEMS

(71) Applicant: Heron Therapeutics, Inc., Redwood City, CA (US)

(72) Inventors: Thomas B. Ottoboni, Belmont, CA (US); Lee Ann Lynn Girotti, San Bruno, CA (US)

(73) Assignee: Heron Therapeutics, Inc., Redwood City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/260,820

(22) Filed: Sep. 9, 2016

(65) Prior Publication Data

US 2016/0375140 A1    Dec. 29, 2016

Related U.S. Application Data

(63) Continuation of application No. 14/691,464, filed on Apr. 20, 2015.

(60) Provisional application No. 61/982,314, filed on Apr. 21, 2014, provisional application No. 61/996,788, filed on May 14, 2014, provisional application No. 62/131,797, filed on Mar. 11, 2015.

(51) Int. Cl.
| | | |
|---|---|---|
| *A61K 47/34* | (2017.01) | |
| *A61K 31/5415* | (2006.01) | |
| *A61K 31/445* | (2006.01) | |
| *A61K 31/196* | (2006.01) | |
| *A61K 9/127* | (2006.01) | |
| *A61K 9/14* | (2006.01) | |
| *A61K 9/00* | (2006.01) | |
| *A61K 47/12* | (2006.01) | |
| *A61K 47/14* | (2017.01) | |
| *A61K 31/00* | (2006.01) | |
| *A61K 47/20* | (2006.01) | |
| *A61K 47/32* | (2006.01) | |

(52) U.S. Cl.
CPC ............ *A61K 47/34* (2013.01); *A61K 9/0019* (2013.01); *A61K 9/0024* (2013.01); *A61K 9/0085* (2013.01); *A61K 9/127* (2013.01); *A61K 9/14* (2013.01); *A61K 31/00* (2013.01); *A61K 31/196* (2013.01); *A61K 31/445* (2013.01); *A61K 31/5415* (2013.01); *A61K 47/12* (2013.01); *A61K 47/14* (2013.01); *A61K 47/20* (2013.01); *A61K 47/32* (2013.01)

(58) Field of Classification Search
CPC .................................................. A61K 47/30
See application file for complete search history.

(56) References Cited

U.S. PATENT DOCUMENTS

| | | |
|---|---|---|
| 4,079,038 A | 3/1978 | Choi et al. |
| 4,093,709 A | 6/1978 | Choi et al. |
| 4,131,648 A | 12/1978 | Choi et al. |
| 4,138,344 A | 2/1979 | Choi et al. |
| 4,180,646 A | 12/1979 | Choi et al. |
| 4,304,767 A | 12/1981 | Heller et al. |
| 4,549,010 A | 10/1985 | Sparer et al. |
| 4,946,931 A | 8/1990 | Heller et al. |
| 4,957,998 A | 9/1990 | Heller et al. |
| 5,968,543 A | 10/1999 | Heller et al. |
| 6,132,766 A | 10/2000 | Sankaram et al. |
| 6,613,335 B1 | 9/2003 | Ruelle |
| 7,666,914 B2 | 2/2010 | Richlin et al. |
| 8,182,835 B2 | 5/2012 | Kim et al. |
| 8,252,304 B2* | 8/2012 | Ng ........................... A61K 8/85 424/422 |
| 8,834,821 B2 | 9/2014 | Kim et al. |

(Continued)

FOREIGN PATENT DOCUMENTS

| | | |
|---|---|---|
| EP | 0795329 A1 | 9/1997 |
| WO | WO 03/059320 A1 | 7/2003 |

(Continued)

OTHER PUBLICATIONS

Einmahl et al., "A new poly(ortho ester)-based drug delivery system as an adjunct treatment in filtering surgery", Inv. Ophthalmol. Vis. Sci., vol. 42, No. 3, pp. 695-700 (2013).

Elhakim et al., "Effects of intraperitoneal lidocaine combined with intravenous or intraperitoneal tenoxicam on pain relief and bowel recovery after laparoscopic cholecystectomy", Acta Anaesthesiol. Scand., vol. 44, No. 8, pp. 929-933 (2000).

Heller et al., "Preparation of polyacetals by the reaction of divinyl ethers and polyols", J. Polymer Sci.: Polymer Letters Ed., vol. 18, No. 4, pp. 293-297 (1980).

International Search Report from PCT/US2015/026695 mailed Oct. 7, 2015, Application now published as International Publication No. WO2015/164272 on Oct. 29, 2015.

*Primary Examiner* — Frederick Krass
*Assistant Examiner* — Amanda Heyes
(74) *Attorney, Agent, or Firm* — Susan L. Harlocker; Judy Mohr; McDermott Will & Emery LLP

(57) ABSTRACT

Compositions comprised of a delivery vehicle or delivery system and an active agent dispersed within the delivery vehicle or system, wherein the delivery vehicle or system contains a polyorthoester polymer and a polar aprotic solvent. Also disclosed are low viscosity delivery systems for administration of active agents. The low viscosity delivery systems have a polyorthoester polymer, a polar aprotic solvent and a solvent containing a triglyceride viscosity reducing agent. Compositions described include an amide- or anilide-type local anesthetic of the "caine" classification, and a non-steroidal anti-inflammatory drug (NSAID), along with related methods, e.g., for treatment of post-operative pain or for prophylactic treatment of pain. The compositions are suitable for delivery via, e.g., direct application and instillation, intradermal injection, subcutaneous injection, and nerve block (perineural).

14 Claims, 13 Drawing Sheets

(56) References Cited

U.S. PATENT DOCUMENTS

| | | |
|---|---|---|
| 8,920,820 B2 | 12/2014 | Folger et al. |
| 2002/0037300 A1 | 3/2002 | Ng et al. |
| 2002/0168336 A1 | 11/2002 | Ng et al. |
| 2005/0079202 A1 | 4/2005 | Chen et al. |
| 2006/0100160 A1 | 5/2006 | Xu et al. |
| 2007/0265329 A1 | 11/2007 | Devang et al. |
| 2008/0299168 A1* | 12/2008 | Dadey ............ A61K 9/0024 424/423 |
| 2010/0305500 A1 | 12/2010 | Lambert et al. |
| 2013/0165429 A1 | 6/2013 | Ray, II et al. |
| 2014/0275046 A1 | 9/2014 | Ottoboni et al. |
| 2014/0275145 A1 | 9/2014 | Ottoboni et al. |
| 2014/0296282 A1 | 10/2014 | Ottoboni et al. |
| 2015/0297729 A1 | 10/2015 | Ottoboni et al. |

FOREIGN PATENT DOCUMENTS

| | | |
|---|---|---|
| WO | WO 2010/093374 A1 | 8/2010 |
| WO | WO 2014/143635 A1 | 9/2014 |
| WO | WO 2015/164272 A2 | 10/2015 |

\* cited by examiner

LONG-ACTING POLYMERIC DELIVERY SYSTEMS

CROSS-REFERENCE TO RELATED APPLICATIONS

This application is a continuation application of U.S. application Ser. No. 14/691,464 filed Apr. 20, 2015, which claims the benefit of U.S. Provisional Application No. 61/982,314 filed Apr. 21, 2014, and of U.S. Provisional Application No. 61/996,788 filed May 14, 2014, and of U.S. Provisional Application No. 62/131,797 filed Mar. 11, 2015, each of which is incorporated herein in its entirety.

TECHNICAL FIELD

The present disclosure is directed to compositions for delivery of pharmaceutically active agents to subjects in need thereof. In one embodiment, compositions disclosed herein provide delivery of one or more active agents over a period of up to about eight days. Exemplary compositions are formulated for the treatment and management of pain, such as post-operative pain, or for the treatment or prophylactic treatment of emesis.

BACKGROUND

Optimizing the time release profile for delivery of therapeutic agents after administration to a patient is a primary consideration when formulating pharmaceuticals for use in the medical community. The administered formulation can significantly affect both the duration of the drug release and delivery to a patient, as well as the ability of the active agent to remain in the body to provide its intended therapeutic effect. Depending on the condition being treated, it may be necessary to provide rapid delivery over a relatively short period of time or extended release for long term treatment without the inconvenience of repeated administrations. Regardless, the ultimate goal is often to provide optimal therapeutic benefit with minimal adverse side effects.

Pain is defined by the International Association for the Study of Pain (IASP) as an unpleasant sensory and emotional experience associated with actual or potential tissue damage, or described in terms of such damage (Classification of Chronic Pain, $2^{nd}$ Ed., Eds. Merkskey & Bogduk, IASP Press, 1994). An effective pain treatment modality is generally considered to be one which provides relief of pain with minimal adverse and/or unwanted side-effects. Treatment of acute pain, such as post-operative pain following surgery, is an area of active investigation. Indeed, the effective treatment of post-operative pain is now considered to be an essential component of the overall care of a surgical patient.

Surgical pain is generally due to inflammation from tissue trauma (e.g., due to the surgical incision, dissection or burns) or direct nerve injury (e.g., nerve transection, stretching, or compression). Pain relief is of primary importance to almost every patient undergoing surgery and to medical personnel treating or caring for a patient undergoing or recovering from a surgical procedure. Pre-operatively, one of the most common questions asked by patients pertains to the amount of pain that they will experience following surgery (Vadivelu, N., Yale J. of Biology and Medicine 83 (2010), p. 11-25). Effective analgesia is vital for ensuring patient comfort, encouraging early mobilization, promoting earlier patient discharge from the medical setting (e.g., hospital, outpatient facility or the like), and for providing enhanced recovery times. Effective treatment of post-operative pain may also reduce the onset/occurrence of chronic pain syndromes such as neuropathic pain and/or the development of depression. Additional advantages of effective post-operative pain management include fewer pulmonary and cardiac complications and a reduced risk of deep vein thrombosis (Ramsay, M., Proc (Bayl Univ Med Centr). 2000 July; 13(3):244-247). In contrast, inadequate pain control may result in increased morbidity or mortality (Sharrock N E, et al., Anesth Analg. 1995 February; 80(2):242-8).

Unfortunately, although there has been a significant increase in knowledge related to the physiology of pain over the last decade, the resulting implications in clinical practice have failed to follow suit. Even after decades of advances in the understanding of the physiology and psychology of pain, one of the mainstays of pain therapy remains the use of opioids. While effective analgesics, opioids also carry with them many undesirable side effects, such as sedation, respiratory depression, nausea and vomiting, hypotension, bradycardia, risk of addiction, to name a few.

One approach for providing localized, effective, long-acting relief of pain, particularly acute pain such as post-surgical pain, is the utilization of a sustained or extended release system. Numerous factors can impact the design of an effective drug delivery system and certain classes of drugs, such as the local anesthetics, are typically considered to be relatively short lasting such that they are most often used only in relatively minor or moderate procedures. There remains a need for compositions for the treatment of pain that are long-lasting, efficacious, convenient to administer, and that can overcome some of the drawbacks associated with the use of opioids. The present compositions and methods satisfy these and other needs.

BRIEF SUMMARY

In one aspect, a composition comprising an amide-type local anesthetic, a non-steroidal anti-inflammatory drug (NSAID) and a delivery vehicle is provided.

In one embodiment, the composition is an aqueous based solution.

In another embodiment, the delivery vehicle is a sustained-release delivery vehicle.

In one embodiment, the composition is injectable.

In another embodiment, the composition is suitable for administration as an intramuscular injection, transdermally, topically, as a subcutaneous injection, as a perineural injection or to a wound.

In one embodiment, the sustained-release delivery vehicle is a polymeric composition, a liposomal composition, a microsphere composition, a non-polymeric composition or an implantable device.

In one embodiment, the sustained release delivery vehicle is not a microsphere composition.

In one embodiment the sustained release delivery vehicle is not a liposomal composition.

In one embodiment the sustained release delivery vehicle is not a non-polymeric composition.

In one embodiment the sustained release delivery vehicle is not an implantable device.

In one embodiment, the composition has a viscosity of less than 10,000 mPa-s when viscosity is measured at 37° C. using a viscometer.

In yet another embodiment, the sustained-release delivery vehicle is a liposome selected from the group consisting of small unilamellar vesicles (SUV), large unilamellar vesicles (LUV), multi-lamellar vesicles (MLV) and multivesicular liposomes (MVL).

In another embodiment, the amide-type local anesthetic is entrapped in an aqueous space of the liposome or in a lipid layer of the liposome.

In another embodiment, the non-steroidal anti-inflammatory drug (NSAID) is entrapped in an aqueous space of the liposome or in a lipid layer of the liposome.

In still another embodiment, the sustained-release delivery vehicle is a microsphere comprised of a bioerodible or biodegradable polymer.

In one embodiment, the amide-type local anesthetic and the non-steroidal anti-inflammatory drug (NSAID) are entrapped in the microsphere.

In one embodiment, the implantable device is an osmotic pump with a reservoir comprising the amide-type local anesthetic and the non-steroidal anti-inflammatory drug (NSAID).

In another embodiment, the sustained-release delivery vehicle is a non-polymeric formulation comprising sucrose acetate isobutyrate.

In still another embodiment, the sustained-release delivery vehicle is a polymeric formulation in the form of a semi-solid polymer formulation comprising a polymer, the amide-type local anesthetic and the non-steroidal anti-inflammatory drug (NSAID).

In one embodiment, the polymer is a bioerodible or biodegradable polymer.

In yet another embodiment, the polymer formulation forms an implant or depot in situ.

In still another embodiment, the polymer is selected from the group consisting of polylactides, polyglycolides, poly(lactic-co-glycolic acid) copolymers, polycaprolactones, poly-3-hydroxybutyrates, and polyorthoesters.

In a further embodiment, the sustained-release delivery vehicle is a polymeric formulation in the form of a semi-solid polymer formulation comprising a polyorthoester, the amide-type local anesthetic and the non-steroidal anti-inflammatory drug (NSAID).

In one embodiment, the amide-type local anesthetic is selected from the group consisting of bupivacaine, ropivacaine, levobupivacaine, dibucaine, mepivacaine, procaine, lidocaine, and tetracaine.

In yet another embodiment, the active agent is ropivacaine.

In yet an alternative embodiment, the active agent is bupivacaine.

In a further embodiment related to any one or more of the foregoing embodiments, the non-steroidal anti-inflammatory drug (NSAID) is an enolic-acid NSAID. Exemplary enolic-acid NSAID include meloxicam, piroxicam, tenoxicam, droxicam, lornoxicam, and isoxicam.

In a specific embodiment, the enolic-acid NSAID is meloxicam.

In a particular embodiment, the composition comprises bupivacaine and meloxicam.

In one embodiment, the NSAID is not diclofenac.

In another aspect, a composition comprising a delivery vehicle and an amide type local anesthetic of the "caine" classification and an enolic-acid non-steroidal anti-inflammatory drug (NSAID) is provided.

In one embodiment, the amide type local anesthetic is selected from the group consisting of bupivacaine and ropivacaine.

In yet another embodiment, the active agent is ropivacaine.

In yet an alternative embodiment, the active agent is bupivacaine.

In a further embodiment related to any one or more of the foregoing embodiments, the non-steroidal anti-inflammatory drug (NSAID) is an enolic-acid NSAID selected from the group consisting of meloxicam, piroxicam, tenoxicam, droxicam, lornoxicam, and isoxicam.

In a specific embodiment, the enolic-acid NSAID is meloxicam.

In a particular embodiment, the composition comprises bupivacaine and meloxicam.

In a further embodiment related to any one or more of the foregoing embodiments, the composition is a semi-solid or solid composition.

In one embodiment, the delivery vehicle is a sustained-release delivery vehicle. In one embodiment, the sustained-release vehicle is a polymeric vehicle or formulation.

In another embodiment, the sustained-release polymeric vehicle is a solid or semi-solid vehicle comprising a bioerodible or biodegradable polymer.

In an embodiment, the biodegradable or bioerodible polymeric formulation comprises a polymer selected from the group consisting of polylactide, polyglycolide, a poly(lactic-co-glycolic acid) copolymer, polycaprolactone, poly-3-hydroxybutyrate, or a polyorthoester.

In one embodiment, the polyorthoester is selected from the polyorthoesters represented by Formulas I, II, III and IV set forth herein.

In yet a particular embodiment related to the foregoing, the polyorthoester is represented by Formula I.

In yet an additional embodiment, the composition or delivery vehicle further comprises a solvent. The solvent may be either protic or aprotic in nature. In one embodiment, the composition comprises as the delivery vehicle a polyorthoester and a solvent.

In another embodiment, the sustained-release delivery vehicle is selected from the group consisting of microspheres, microparticles, and homogeneous or heterogeneous matrix depots. In one embodiment, the microsphere, microparticle or depot vehicle is biodegradable or bioerodible.

In another embodiment, the sustained-release delivery vehicle is a liposomal formulation or a lipid-based formulation.

In another embodiment, the sustained-release formulation is a polymeric-based solid or semi-solid implant where the amideamide-type local anesthetic and the enolic-acid NSAID are dispersed in the polymeric-based implant. In one embodiment, the implant is a solid polymeric-based vehicle in the form of a suture or a staple.

In yet an additional aspect, provided is a method for extending the pain-relief profile of a delivery vehicle comprising an amide-type local anesthetic and an efficacy-enhancing amount of an NSAID, to thereby provide a composition capable of providing effective pain relief for a period of time that is extended over that of the same composition absent the NSAID. In particular, the resulting composition is generally effective to provide pain relief from about 1 day to at least about 5 days following administration, i.e., is a long-acting formulation for pain relief, rather than a short-acting formulation.

In yet an additional aspect, provided is a method for altering the pain relief profile of a composition comprising a delivery vehicle and an amide-type local anesthetic incorporated and an efficacy-enhancing amount of an enolic acid NSAID in the vehicle, to thereby provide a composition that exhibits a long-term pain reducing effect over a period of about 1-5 days, about 1-2 days, about 1-3 days or about 1-4 days, and optionally beyond, that is at least about 50% of its average pain-relieving effect exhibited from about 1-5 hours post-administration.

In a particular embodiment, the composition is effective to provide measurable plasma concentrations of the amide- or anilide-type local anesthetic and/or the NSAID for a period of at up to about 3 days or up to about 5 days or up to about 7 days or up to about 10 days following administration, or for a period of about 1 days to 3 days, about 1 day to about 5 days, about 1 day to about 7 days, about 3 days to about 5 days, about 3 days to about 7 days or about 5 days to about 10 days. In one embodiment, the plasma concentration of the amide- or anilide-type local anesthetic and/or the NSAID is measured by LC/MS/MS (liquid chromatography/tandem mass spectrometry).

In a particular embodiment, the composition is effective to release a significant portion of both the amide-type local anesthetic and the NSAID from the composition, such that about 80% by weight or more of the amide- or anilide-type local anesthetic and/or the NSAID is released, either in vitro or in vivo, over a period of up to about 3 days or up to about 5 days or up to about 7 days or up to about 10 days following administration or initiation of an in vitro drug release experiment (e.g. as described in Example 5), or for a period of about 1 day to about 3 days, about 1 day to about 5 days, about 1 day to about 7 days or about 5 days to about 10 days, about 2 days to about 5 days, about 3 days to about 5 days, about 4 days to about 5 days, about 2 days to about 4 days, about 3 days to about 4 days, or about 3 days, about 4 days or about 5 days.

In one embodiment, the composition is a synergistic composition wherein release of the amide-type local anesthetic and NSAID in combination provides a synergistic level of pain relief that is greater than a level of pain relief provided by an additive effect of adding the amide-type local anesthetic and NSAID independently. In another embodiment, the composition provides a duration of pain relief that is longer than a duration resulting from an additive effect of adding the amide-type local anesthetic and NSAID independently.

In another aspect, provided is a method of treatment, the method comprising dispensing from a needle a composition comprising an amide- or anilide type local anesthetic combined with an NSAID, such as an enolic-acid NSAID, and a delivery vehicle, to thereby achieve a controlled release of both the local anesthetic and the NSAID from the composition, wherein about 80% by weight or more of both drugs are released over a period of about 3 days, about 4 days, about 5 days, about 6 days, about 7 days, about 8 days, about 9 days, or about 10 days.

In another embodiment, the compositions provided herein are for use in a method of providing local anesthesia to a patient in need thereof. The treatment includes administering to a patient a composition as set forth herein, e.g., comprising an amide or anilide-type local anesthetic, a delivery vehicle and an NSAID, to provide rates of release of both the anesthetic and the NSAID, as well as accompanying pharmacokinetic profiles of each effective for reducing or preventing pain over an extended period following administration. Local administration can be, e.g., at a nerve, into the epidural space, intrathecal, or directly to a surgical site or wound. In one embodiment, about 80% by weight or more of both drugs are released over a period of about 5 days. In another embodiment, the composition is effective to provide significant pain relief for up to about 2 days, about 3 days, about 4 days, about 5 days, about 6 days, or about 7 days following application. In still another embodiment, the composition is effective to provide significant pain relief for about 2 hours to about 4 hours, about 2 hours to about 6 hours, about 2 hours to about 8 hours, about 2 hours to about 10 hours, about 4 hours to about 12 hours, about 6 hours to about 18 hours, about 6 hours to about 24 hours, about 2 hours to about 2 days, about 2 hours to about 4 days, about 1 hour to about 3 days, about 1 hour to about 5 days, about 1 day to about 5 days, about 1 day to about 3 days, about 2 days to about 5 days, about 3 days to about 5 days, about 4 days to about 5 days, about 2 days to about 4 days, about 3 days to about 4 days, or about 2 days, about 3 days or about 4 days.

In yet another embodiment, the compositions and delivery systems provided herein are effective for reducing or treating acute or chronic pain.

In still another aspect, a method for providing pain relief to a patient in need thereof is provided. The method comprises providing a composition as described herein, and instructing that the composition be administered to the patient to provide pain relief for an extended period.

In one embodiment, the extended period of pain relief is at least about 5 days. In another embodiment, the extended period is for up to or equal to about 5 days. In still another embodiment, the extended period is from about 1 day to at least about 5 days or from about 1 day to up to about 5 days. In yet another embodiment, the extended period is for about 3 days.

In one embodiment, the method results in a synergistic increase in pain relief wherein the level of pain relief is greater than a level of pain relief provided by an additive effect of adding the amide-type local anesthetic and NSAID independently. In another embodiment, the method results in a synergistic increase in the duration of pain relief wherein the duration of pain relief is greater than a duration of pain relief provided by an additive effect of adding the amide-type local anesthetic and NSAID independently.

In one embodiment, the composition is administered as a perineural injection. In a further embodiment, the perineural injection is a nerve block.

In a specific embodiment, the composition is administered as a nerve block to treat a painful condition in a subject in need thereof.

In a further specific embodiment, the composition is administered as a nerve block as prophylactic treatment of a painful condition, such as administration prior to surgery for the treatment of pain after surgery, in a subject in need thereof.

In another aspect, an aqueous pharmaceutical composition comprising a therapeutically effective amount of meloxicam and a therapeutically effective amount of an amide-type local anesthetic is provided.

In one embodiment, administration of the aqueous pharmaceutical composition to a subject provides pain relief to the subject for a duration of about 1 hour to about 24 hours, about 1 hour to about 16 hours, about 1 hour to about 12 hours, about 2 hours to about 12 hours, about 3 hours to about 12 hours, about 4 hours to about 12 hours, about 4 hours to about 10 hours, about 5 hours to about 10 hours, about 6 hours to about 10 hours, about 6 hours to about 9 hours, about 6 hours to about 8 hours or about 4 hours to about 8 hours after administration to the subject. In another embodiment, the duration of analgesia is longer than the duration of pain relief provided by administration of a therapeutically effective amount of an aqueous pharmaceutical composition of the amide-type local anesthetic or the meloxicam alone.

In one embodiment, the amide-type local anesthetic is selected from the group consisting of bupivacaine, ropivacaine, levobupivacaine, dibucaine, mepivacaine, procaine, lidocaine, and tetracaine. In another embodiment, the amide-type local anesthetic is bupivacaine. In still another embodiment, the amide-type local anesthetic is ropivacaine.

In another aspect, a pharmaceutically acceptable aqueous solution of meloxicam or pharmaceutically acceptable salt thereof is provided wherein the aqueous solution is suitable for combining with a pharmaceutically acceptable aqueous solution of an amide-type local anesthetic to generate a pharmaceutical mixture suitable for administration to a subject.

In one embodiment, the amide-type local anesthetic is selected from the group consisting of bupivacaine, ropivacaine, levobupivacaine, dibucaine, mepivacaine, procaine, lidocaine, and tetracaine. In another embodiment, the amide-type local anesthetic is bupivacaine. In still another embodiment, the amide-type local anesthetic is ropivacaine.

In one embodiment, the subject is suffering from acute or chronic pain. In another embodiment, the subject is in need of prophylactic treatment for pain.

In one embodiment, the pharmaceutical mixture is suitable for administration as an intramuscular, subcutaneous injection, or perineural injection. In another embodiment, the pharmaceutical mixture is suitable for intravenous administration. In another embodiment, the pharmaceutical mixture is suitable for administration to a wound.

In another aspect, a method for treating a subject in pain or a subject in need of prophylactic treatment of pain is provided, wherein the method comprises administering to the subject an aqueous pharmaceutical composition comprising a therapeutically effective amount of meloxicam and a therapeutically effect amount of an amide-type local anesthetic.

In one embodiment, the amide-type local anesthetic in the aqueous pharmaceutical composition is selected from the group consisting of bupivacaine, ropivacaine, levobupivacaine, dibucaine, mepivacaine, procaine, lidocaine, and tetracaine. In another embodiment, the amide-type local anesthetic is bupivacaine. In still another embodiment, the amide-type local anesthetic is ropivacaine.

In one embodiment the administration of the aqueous pharmaceutical composition to the subject provides pain relief to the subject for a duration of about 1 hour to about 24 hours, about 2 hours to about 18 hours, about 3 hours to about 16 hours, about 4 hours to about 24 hours, about 4 hours to about 22 hours, about 4 hours to about 20 hours, about 4 hours to about 18 hours, about 4 hours to about 16 hours, about 4 hours to about 14 hours, about 4 hours to about 12 hours, about 6 hours to about 48 hours, about 6 hours to about 36 hours, about 6 hours to about 24 hours, about 6 hours to about 20 hours, about 6 hours to about 18 hours, about 6 hours to about 16 hours, about 6 hours to about 14 hours, about 6 hours to about 12 hours or about 6 hours to about 10 hours after administration.

In one embodiment, the pain is chronic or acute pain.

In another aspect, a method for treating a subject in pain or a subject in need of prophylactic treatment of pain is provided, wherein the method comprises mixing a pharmaceutical solution of meloxicam or a pharmaceutically acceptable salt thereof with a pharmaceutical solution of amide-type local anesthetic to prepare a mixed solution and administering the mixed solution to the subject.

In one embodiment the mixed solution is administered to the subject within about 24 hours, about 20 hours, about 16 hours, about 12 hours, about 8 hours, about 6 hours, about 4 hours, about 2 hours, about 1 hour, about 45 minutes, about 30 minutes, about 15 minutes or about 5 minutes after preparing the mixed solution.

In one embodiment, the pharmaceutical solution of meloxicam is an aqueous solution.

In one embodiment, the mixed solution is administered by intramuscular, subcutaneous, or perineural injection. In another embodiment, the mixed solution is administered to a wound.

In one embodiment the administering of the mixed solution to the subject provides pain relief to the subject for a duration of about 1 hour to about 24 hours, about 2 hours to about 18 hours, about 3 hours to about 16 hours, about 4 hours to about 24 hours, about 4 hours to about 22 hours, about 4 hours to about 20 hours, about 4 hours to about 18 hours, about 4 hours to about 16 hours, about 4 hours to about 14 hours, about 4 hours to about 12 hours, about 6 hours to about 48 hours, about 6 hours to about 36 hours, about 6 hours to about 24 hours, about 6 hours to about 20 hours, about 6 hours to about 18 hours, about 6 hours to about 16 hours, about 6 hours to about 14 hours, about 6 hours to about 12 hours or about 6 hours to about 10 hours after administration.

In another aspect, a delivery system comprised of a polyorthoester, a solvent comprising a triglyceride viscosity reducing agent and a polar aprotic solvent in which the polyorthoester is miscible to form a single phase, and a therapeutically active agent dispersed or solubilized in the single phase is provided. In one embodiment, the triglyceride viscosity reducing agent comprises three fatty acid groups each independently comprising between 1-7 carbon atoms, which is also referred to herein as a 'short chain' triglyceride.

In one embodiment, the active agent is released from the delivery system over a period ranging from about 1 day to 8 weeks, about 1 day to 7 weeks, about 1 day to 6 weeks, about 1 day to 5 weeks, about 1 day to 4 weeks, about 1 day to 3 weeks, about 1 day to 2 weeks, about 1 week to 8 weeks, about 1 week to 6 weeks, about 1 week to 4 weeks, about 1 day to 7 days, about 1 day to 6 days, about 1 day to 5 days, about 1 hour to 24 hours, about 2 hours to 18 hours, about 3 hours to 16 hours, about 4 hours to 24 hours, about 4 hours to 22 hours, about 4 hours to 20 hours, about 4 hours to 18 hours, about 4 hours to 16 hours, about 4 hours to 14 hours, about 4 hours to 12 hours, about 6 hours to 48 hours, about 6 hours to 36 hours, about 6 hours to 24 hours, about 6 hours to 20 hours, about 6 hours to 18 hours, about 6 hours to 16 hours, about 6 hours to 14 hours, about 6 hours to 12 hours or about 6 hours to 10 hours.

In one embodiment, the delivery system has a viscosity of less than about 10,000 mPa-s when viscosity is measured at 25° C. using a viscometer, less than about 5,000 mPa-s when viscosity is measured at 25° C. using a viscometer, or less than about 2,500 mPa-s when viscosity is measured at 25° C. using a viscometer. In another embodiment, the delivery system has a viscosity ranging from about 2500 mPa-s to 10,000 mPa-s when measured at 25° C. using a viscometer.

In one embodiment the triglyceride viscosity reducing agent is glycerin triacetate (also called triacetin, 1,2,3-triacetoxypropane, or glycerol triacetate).

In one embodiment, the polar aprotic solvent is an organic solvent having a water solubility of greater than 25% by weight of the solvent in water at room temperature.

In one embodiment, the polar aprotic solvent has a dipole moment greater than about 2 Debye (D).

In one embodiment, the polar aprotic solvent is in a class selected from the group consisting of an amide, an ether, a ketone, and a sulfoxide.

In another embodiment, the polar aprotic solvent is a sulfoxide selected from the group consisting of dimethyl sulfoxide and decylmethylsulfoxide.

In yet another embodiment, the polar aprotic solvent is an amide selected from the group consisting of 2-pyrrolidone, dimethyl formamide, N-methyl-2-pyrrolidone, and dimethyl acetamide.

In one embodiment, the polar aprotic solvent is an ether selected from dimethyl isosorbide and tetrahydrofuran.

In one embodiment, the polar aprotic solvent is a ketone selected from the group consisting of acetone and methyl ethyl ketone.

In one embodiment, the polar aprotic solvent is a lactone selected from the group consisting of ester-caprolactone and butyrolactone.

In one embodiment, the polar aprotic solvent is an ester of an alcohol, propylene carbonate (4-methyl-1,3-diololan-2-one).

In one embodiment, the polar aprotic solvent is 1-dodecylazacycloheptan-2-one.

In one embodiment, the polar aprotic solvent is dimethylsulfoxide (DMSO) or N-methyl pyrrolidone (NMP) or dimethyl acetamide (DMAC).

In one embodiment, the polar aprotic solvent is dimethylsulfoxide (DMSO) or N-methyl pyrrolidone (NMP).

In one embodiment, the therapeutically active agent is an anti-emetic.

In one embodiment, the therapeutically active agent is granisetron.

In one embodiment, the therapeutically active agent is an anesthetic. In another embodiment, the anesthetic is a local amide-type anesthetic. In yet another embodiment, the anesthetic is selected from the group consisting of bupivacaine, levobupivacaine, dibucaine, mepivacaine, procaine, lidocaine, tetracaine, and ropivacaine.

In one embodiment, the therapeutically active agent is ropivacaine or bupivacaine.

In one embodiment, the composition comprising the anesthetic further comprises a nonsteroidal anti-inflammatory agent (NSAID). In another embodiment, the NSAID is an enolic-acid NSAID. In still another embodiment, the NSAID is selected from the group consisting of meloxicam, piroxicam, tenoxicam, droxicam, lornoxicam, and isoxicam.

In one embodiment, the therapeutically active agent is a opioid. In another embodiment, the therapeutically active agent is buprenorphine.

In one embodiment, the polyorthoester is selected from the polyorthoesters represented by Formulas I, II, III and IV set forth herein below.

In one embodiment, the polyorthoester is the polyorthoester represented by the structure shown as Formula I,

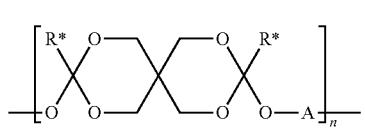

I where: R* is a methyl, ethyl, propyl or butyl, n is the number of repeating units and is an integer ranging from 5 to 400, and A in each subunit is $R^1$ or $R^3$.

In one embodiment, R* is ethyl.

In one embodiment, A corresponds to $R^1$, where $R^1$ is

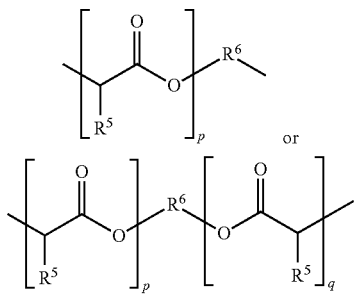

where p and q are each independently integers ranging from about 1 to 20, each $R^5$ is independently hydrogen or $C_{1-4}$ alkyl; and $R^6$ is:

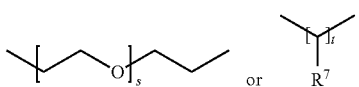

where s is an integer from 0 to 10; t is an integer from 2 to 30; and $R^7$ is hydrogen or $C_{1-4}$ alkyl. In another embodiment, R7 is C1, C2, C3, or C4 alkyl. In a particular embodiment, $R^7$ is H. In still another embodiment, the $R^1$ subunits are α-hydroxy acid-containing subunits. In another embodiment, p and q are each independently selected from 1, 2, 3, 4, 5, 6, 7, 8, 9, 10, 11, 12, 13, 14, 15, 16, 17, 18, 19, and 20. In yet another embodiment, R5 is independently hydrogen, or C1, C2, C3, or C4 alkyl.

In one embodiment, A corresponds to $R^3$, where $R^3$ is:

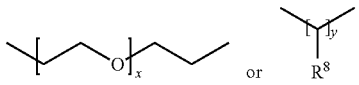

and x is an integer ranging from 1 to 100. In another embodiment, x is selected from 0, 1, 2, 3, 4, and 5; y is an integer in a range from 2 to 30; and $R^8$ is hydrogen or $C_{1-4}$ alkyl. In still another embodiment, $R^8$ is a C1, C2, C3 or C4 alkyl. In another embodiment, $R^8$ is H.

In one embodiment, the polyorthoester is one in which A is $R^1$ or $R^3$, where $R^1$ is

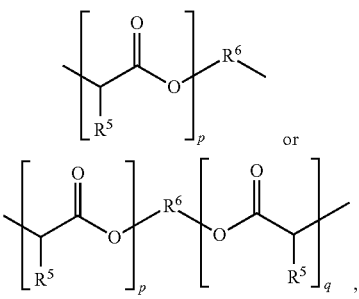

where p and q are each independently selected from 1, 2, 3, 4, 5, 6, 7, 8, 9, 10, 11, 12, 13, 14, 15, 16, 17, 18, 19, and 20 in any repeating unit, where the average number of p or the average number of the sum of p and q (p+q) is between about 1 and 7; x and s are each independently an integer ranging from 0 to 10; and t and y are each independently an integer ranging from 2 to 30. In another embodiment, the sum of p and q is 1, 2, 3, 4, 5, 6 or 7 in any repeating unit of $R^1$. In yet another embodiment, $R^5$ is H.

In one embodiment, A is $R^1$ or $R^3$, where $R^1$ is

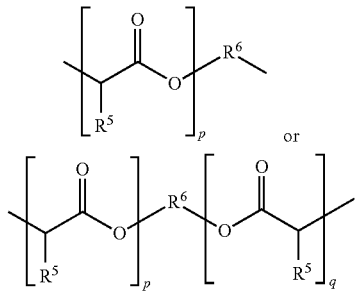

and p and q are each independently integers ranging from about 1 and 20, about 1 and 15, or about 1 and 10 in any repeating unit of $R^1$, where the average number of p or the average number of the sum of p and q (i.e., p+q) is between about 1 and 7. In another embodiment, x and s each independently range from 0 to about 7 or from 1 to about 5. In still another embodiment, t and y each independently range from 2 to 10.

In one embodiment, $R^5$ is hydrogen or methyl.

In one embodiment, s and x are each independently selected from 1, 2, 3, 4, 5, 6, 7 and 8. In another embodiment, s is 2. In still another embodiment, x is 2.

In one embodiment, the polyorthoester comprises alternating residues of 3,9-diethyl-3,9-2,4,8,10-tetraoxaspiro[5.5]undecane-3,9-diyl and A:

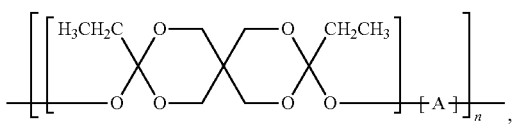

where A is as described above.

In one particular embodiment related to the polyorthoester in the delivery system, the polyorthoester has a molecular weight ranging from about 2,500 daltons to 10,000 daltons.

In one embodiment related to the delivery system, the polyorthoester is represented by the structure shown as Formula I and is in an amount ranging from about 65 to 75 percent by weight of the delivery system.

In one embodiment related to the delivery system, the triglyceride viscosity reducing agent is present in an amount ranging from about 10 wt % to 50 wt %, 10 wt % to 35 wt %, 15 wt % to 30 wt %, or 20 wt % to 25 wt %, or about 15 wt %, 16 wt %, 17 wt %, 18 wt %, 19 wt %, 20 wt %, 21 wt %, 22 wt %, 23 wt %, 24 wt %, 25 wt %, 27 wt %, 28 wt %, 29 wt %, 30 wt %, 31 wt %, 32 wt %, 33 wt %, 34 wt %, or 35 wt % of the delivery system.

In one embodiment related to the delivery system, the aprotic solvent is present in an amount ranging from about 10 wt % to 35 wt %, 10 wt % to 30 wt %, 10 wt % to 20 wt %, 10 wt % to 15 wt %, or about 2 wt %, 3 wt %, 4 wt %, 5 wt %, 6 wt %, 7 wt %, 8 wt %, 9 wt %, 10 wt %, 11 wt %, 12 wt %, 13 wt %, 14 wt %, 15 wt %, 16 wt %, 17 wt %, 18 wt %, 19 wt %, or 20 wt % of the delivery system.

In one embodiment related to the delivery system, the active agent is present in an amount ranging from about 1 to 8 percent, 2 to 6 percent, 2 to 5 percent, or 1 to 5 percent by weight of the delivery system.

In one embodiment related to the delivery system, the polyorthoester is represented by the structure shown as Formula I in accordance with any one or more of the combinations and sets of variables related thereto as provided herein, the active agent is granisetron in an amount ranging from about 1 to 5 percent by weight of the delivery system, the aprotic solvent is DMSO or NMP in an amount ranging from about 5 to 35 percent by weight of the delivery system, and the triglyceride viscosity reducing agent is triacetin in an amount ranging from about 10 to 30 percent by weight of the delivery system.

In a particular embodiment, the solvent comprising the triglyceride viscosity reducing agent and the polar aprotic solvent is in an amount ranging from about 15 to 50 percent by weight of the delivery system, and the therapeutic agent is in an amount ranging from about 3 to 30 percent by weight of the delivery system.

In yet another embodiment, the polyorthoester is represented by the structure shown as Formula I in accordance with any one or more of the combinations and sets of variables related thereto as provided herein, the active agent is ropivacaine or bupivacaine in an amount ranging from about 3 to 30 percent by weight of the delivery system, the triglyceride viscosity reducing agent is triacetin in an amount ranging from about 15 to 30 percent by weight of the delivery system, and the solvent is selected from dimethyl sulfoxide, dimethyl acetamide and N-methyl pyrrolidone and is in an amount ranging from about 15 to 50 percent by weight of the delivery system.

In one embodiment, the polyorthoester is represented by the structure shown as Formula I, the active agent is granisetron in an amount ranging from about 1 to 5 percent by weight of the composition, and the solvent is DMSO in an amount ranging from about 10 to 35 percent by weight of the composition.

In another aspect, a method of administering a therapeutically active agent is provided. The method comprises dispensing from a needle a delivery system or a composition as described herein comprising a polyorthoester, a triglyceride viscosity reducing agent and an aprotic solvent in which the polyorthoester is miscible to form a single phase, and a therapeutically active agent dispersed or solubilized in the single phase, wherein the solvent is selected to achieve a controlled release of the active agent from the composition according to a predetermined release profile, and wherein the active agent is released from the delivery system or composition over a period ranging from about 1 day to 8 weeks, 1 day to 7 weeks, 1 day to 6 weeks, 1 day to 5 weeks, 1 day to 4 weeks, 1 day to 3 weeks, 1 day to 2 weeks, 1 week to 8 weeks, 1 week to 6 weeks, 1 week to 4 weeks, 1 day to 7 days, 1 day to 6 days, 1 day to 5 days, 1 hour to 24 hours, 2 hours to 18 hours, 3 hours to 16 hours, 4 hours to 24 hours, 4 hours to 22 hours, 4 hours to 20 hours, 4 hours to 18 hours, 4 hours to 16 hours, 4 hours to 14 hours, 4 hours to 12 hours, 6 hours to 48 hours, 6 hours to 36 hours, 6 hours to 24 hours, 6 hours to 20 hours, 6 hours to 18 hours, 6 hours to 16 hours, 6 hours to 14 hours, 6 hours to 12 hours or 6 hours to 10 hours.

In another aspect, provided is a method of treatment comprising dispensing from a needle to a patient in need there of a delivery system composition comprised of a polyorthoester, comprising a triglyceride viscosity reducing agent, an aprotic solvent in which the polyorthoester is miscible to form a single phase, and a therapeutically active agent dispersed or solubilized in the single phase, wherein the triglyceride viscosity reducing agent and the aprotic solvent are selected to achieve a controlled release of the active agent from the composition according to a predetermined release profile, and wherein the active agent is released from the delivery system or composition over a period ranging from about 1 day to 8 weeks, 1 day to 7 weeks, 1 day to 6 weeks, 1 day to 5 weeks, 1 day to 4 weeks, 1 day to 3 weeks, 1 day to 2 weeks, 1 week to 8 weeks, 1 week to 6 weeks, 1 week to 4 weeks, 1 day to 7 days, 1 day to 6 days, 1 day to 5 days, 1 hour to 24 hours, 2 hours to 18 hours, 3 hours to 16 hours, 4 hours to 24 hours, 4 hours to 22 hours, 4 hours to 20 hours, 4 hours to 18 hours, 4 hours to 16 hours, 4 hours to 14 hours, 4 hours to 12 hours, 6 hours to 48 hours, 6 hours to 36 hours, 6 hours to 24 hours, 6 hours to 20 hours, 6 hours to 18 hours, 6 hours to 16 hours, 6 hours to 14 hours, 6 hours to 12 hours or 6 hours to 10 hours. In one embodiment, the delivery system is administered as a perineural injection. In a further embodiment, the perineural injection is a nerve block.

In a specific embodiment, the delivery system is administered as a nerve block to treat a painful condition in a subject in need thereof.

In a further specific embodiment, the delivery system is administered as a nerve block as prophylactic treatment of a painful condition, such as administration prior to surgery for the treatment of pain after surgery, in a subject in need thereof.

For each of the above embodiments of the composition, or related methods or systems, each embodiment directed to an amide- or anilide-type local anesthetic is meant to apply to each and every embodiment of the NSAID, and each embodiment of delivery vehicle is meant to apply to each embodiment of the combination of the amide- or anilide-type local anesthetic and the enolic-acid NSAID, etc.

Additional embodiments of the present systems, compositions and methods will be apparent from the following description, drawings, examples, and claims. As can be appreciated from the foregoing and following description, each and every feature described herein, and each and every combination of two or more of such features, is included within the scope of the present disclosure provided that the features included in such a combination are not mutually inconsistent. In addition, any feature or combination of features may be specifically excluded from any embodiment of the present invention. Additional aspects and advantages of the present invention are set forth in the following description and claims, particularly when considered in conjunction with the accompanying examples and drawings.

DETAILED DESCRIPTION

I. Definitions

Figure 1A:
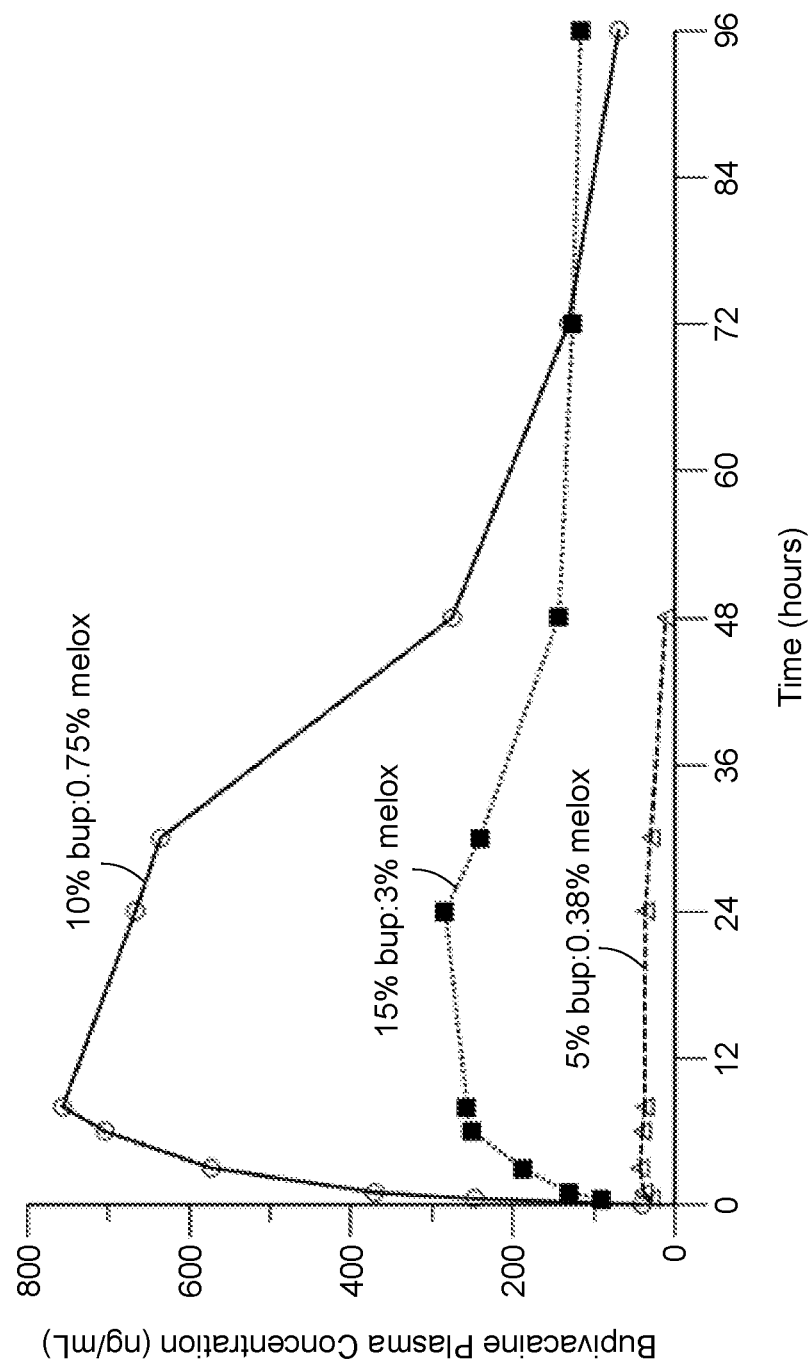
FIGS. 1A-1B are graphs of plasma concentration of bupivacaine (FIG. 1A) and of meloxicam (FIG. 1B), in ng/mL, as a function of time, in hours, after administration in vivo to sheep of exemplary compositions comprised of a polyorthoester delivery vehicle and bupivacaine and meloxicam at concentrations of 15 wt % bupivacaine/3 wt % meloxicam (closed squares; composition no. 8026-04-03); 10 wt % bupivacaine/0.75 wt % meloxicam (open circles; composition no. 8026-04-04); and 5 wt % bupivacaine/0.38 wt % meloxicam (open triangles; composition no. 8026-04-05)

As used in this specification, the singular forms "a," "an," and "the" include plural referents unless the context clearly dictates otherwise. Thus, for example, reference to a "polymer" includes a single polymer as well as two or more of the same or different polymers, reference to an "excipient" includes a single excipient as well as two or more of the same or different excipients, and the like.

Where a range of values is provided, it is intended that each intervening value between the upper and lower limit of that range and any other stated or intervening value in that stated range is encompassed within the disclosure. For example, if a range of 10 to 20 weight percent (wt %) is stated, it is intended that 11, 12, 13, 14, 15, 16, 17, 18, and 19 wt % are also explicitly disclosed, as well as the range of values greater than or equal to 10 wt % up to about 20 wt % and the range of values less than or equal to 20 wt % down to about 10 wt %.

"Bioerodible", "bioerodibility" and "biodegradable", which are used interchangeably herein, refer to the degradation, disassembly or digestion of a polymer by action of a biological environment, including the action of living organisms and most notably at physiological pH and temperature. As an example, a principal mechanism for bioerosion of a polyorthoester is hydrolysis of linkages between and within the units of the polyorthoester.

A "polymer susceptible to hydrolysis" such as a polyorthoester refers to a polymer that is capable of degradation, disassembly or digestion via reaction with water molecules. Such a polymer contains hydrolyzable groups in the polymer. Examples of polymers susceptible to hydrolysis may include, but are not limited to, polymers described herein, and those described in U.S. Pat. Nos. 4,079,038, 4,093,709, 4,131,648, 4,138,344, 4,180,646, 4,304,767, 4,957,998, 4,946,931, 5,968,543, 6,613,335, and 8,252,304, and U.S. Patent Publication No. 2007/0265329, which are incorporated herein by reference in its entirety.

"Molecular mass" in the context of a polymer such as a polyorthoester, refers to the nominal average molecular mass of a polymer, typically determined by size exclusion chromatography, light scattering techniques, or velocity. Molecular weight can be expressed as either a number-average molecular weight or a weight-average molecular weight. Unless otherwise indicated, all references to molecular weight herein refer to the weight-average molecular weight. Both molecular weight determinations, number-average and weight-average, can be measured using gel permeation chromatographic or other liquid chromatographic techniques. Other methods for measuring molecular weight values can also be used, such as the measurement of colligative properties (e.g., freezing-point depression, boiling-point elevation, or osmotic pressure) to determine number-average molecular weight or the use of light scattering techniques, ultracentrifugation or viscometry to determine weight-average molecular weight. The polymers of the invention are typically polydisperse (i.e., number-average molecular weight and weight-average molecular weight of the polymers are not equal), possessing low polydispersity values such as less than about 3.0, less than about 2.75, less than about 2.25, less than about 1.5, and less than about 1.03.

"Semi-solid" denotes the mechano-physical state of a material that is flowable under moderate stress. More specifically, a semi-solid material will generally have a viscosity between about 1,000 and 3,000,000 mPa-s at 37° C., especially between about 1,000 and 50,000 mPa-s at 37° C.

An "active agent" or "active ingredient" refers to any compound or mixture of compounds which produces a beneficial or useful result. Generally, "active agent" or "drug" refers to any organic or inorganic compound or substance having bioactivity and adapted or used for therapeutic purposes. As used herein, reference to a drug, as well as reference to other chemical compounds herein, is meant to include the compound in any of its pharmaceutically acceptable forms, including isomers such as diastereomers and enantiomers, salts, solvates, and polymorphs, particular crystalline forms, as well as racemic mixtures and pure isomers of the compounds described herein, where applicable. Active agents are distinguishable from such components as vehicles, carriers, diluents, lubricants, binders and other formulating aids, and encapsulating or otherwise protective components. Examples of active agents are pharmaceutical, agricultural or cosmetic agents.

Examples of active agents are pharmaceutical, agricultural or cosmetic agents. Suitable pharmaceutical agents include locally or systemically acting pharmaceutically active agents which may be administered to a subject by topical or intralesional application (including, for example, applying to abraded skin, lacerations, puncture wounds, etc., as well as into surgical wounds or incisions) or by injection, such as subcutaneous, intradermal, intramuscular, intraocular or intra-articular injection. Suitable pharmaceutical agents include polysaccharides, DNA and other polynucleotides, antisense oligonucleotides, antigens, antibodies, vaccines, vitamins, enzymes, proteins, naturally occurring or bioengineered substances, and the like, anti-infectives (including antibiotics, antivirals, fungicides, scabicides or pediculicides), antiseptics (e.g., benzalkonium chloride, benzethonium chloride, chlorhexidine gluconate, mafenide acetate, methylbenzethonium chloride, nitrofurazone, nitromersol and the like), steroids (e.g., estrogens, progestins, androgens, adrenocorticoids and the like), opioids (e.g. buprenorphine, butorphanol, dezocine, meptazinol, nalbuphine, oxymorphone and pentazocine), therapeutic polypeptides (e.g. insulin, erythropoietin, morphogenic proteins such as bone morphogenic protein, and the like), analgesics and anti-inflammatory agents (e.g., aspirin, ibuprofen, naproxen, ketorolac, COX-1 inhibitors, COX-2 inhibitors and the like), antipsychotic agents (for example, phenothiazines including chlorpromazine, triflupromazine, mesoridazine, piperacetazine and thioridazine; thioxanthenes including chlorprothixene and the like), antiangiogenic agents (e.g., combresiatin, contortrostatin, anti-VEGF and the like), anti-anxiety agents (for example, benzodiazepines including diazepam, alprazolam, clonazepam, oxazepam; and barbiturates), antidepressants (including tricyclic antidepressants and monoamine oxidase inhibitors including imipramine, amitriptyline, doxepin, nortriptyline, amoxapine, tranylcypromine, phenelzine and the like), stimulants (for example, methylphenidate, doxapram, nikethamide and the like), narcotics (for example, buprenorphine, morphine, meperidine, codeine and the like), analgesic-antipyretics and anti-inflammatory agents (for example, aspirin, ibuprofen, naproxen and the like), local anesthetics (e.g., the amide- or anilide-type local anesthetics such as bupivacaine, levobupivacaine, dibucaine, mepivacaine, procaine, lidocaine, tetracaine, ropivacaine, and the like), fertility control agents, chemotherapeutic and anti-neoplastic agents (for example, mechlorethamine, cyclophosphamide, 5-fluorouracil, thioguanine, carmustine, lomustine, melphalan, chlorambucil, streptozocin, methotrexate, vincristine, bleomycin, vinblastine, vindesine, dactinomycin, daunorubicin, doxorubicin, tamoxifen and the like), cardiovascular and anti-hypertensive agents (for example, procainamide, amyl nitrite, nitroglycerin, propranolol, metoprolol, prazosin, phentolamine, trimethaphan, captopril, enalapril and the like), drugs for the therapy of pulmonary disorders, anti-epilepsy agents (for example, phenyloin, ethotoin and the like), anti-hidrotics, keratoplastic agents, pigmentation agents or emollients, antiemetic agents (such as ondansetron, granisetron, tropisetron, metoclopramide, domperidone, scopolamine, palonosetron, and the like). The composition of the present application may also be applied to other locally acting active agents, such as astringents, antiperspirants, irritants, rubefacients, vesicants, sclerosing agents, caustics, escharotics, keratolytic agents, sunscreens and a variety of dermatologics including hypopigmenting and antipruritic agents. The term "active agents" further includes biocides such as fungicides, pesticides and herbicides, plant growth promoters or inhibitors, preservatives, disinfectants, air purifiers and nutrients. Pro-drugs and pharmaceutically acceptable salts of the active agents are included within the scope of the present application.

A "small molecule" is a molecule, typically a drug, having a molecular weight of less than about 900 daltons.

The term "amide-type" as used herein refers to an amide- or amino-anilide-type or "-caine" class of local anesthetic-amide, such as bupivacaine, levobupivacaine, ropivacaine, etidocaine, lidocaine, mepivacaine, prilocaine and the like. Molecules in this class contain an amino functionality as well as an anilide group, for example, an amide group formed from the amino nitrogen of a phenyl-substituted aniline. These molecules are generally weak bases, with pKb values ranging from about 5.8 to about 6.4.

An "enolic-acid NSAID" as used herein refers to non-steroidal anti-inflammatory drug of the Oxicam class such as meloxicam, piroxicam, tenoxicam, droxicam (prodrug of piroxicam), lornoxicam and the like. Molecules in this class contain an acidic enol functional group.

"Pharmaceutically acceptable salt" denotes a salt form of a drug having at least one group suitable for salt formation that causes no significant adverse toxicological effects to the patient. Pharmaceutically acceptable salts include salts prepared by reaction with an inorganic acid, an organic acid, a basic amino acid, or an acidic amino acid, depending upon the nature of the functional group(s) in the drug. Suitable pharmaceutically acceptable salts include acid addition salts which may, for example, be formed by mixing a solution of a basic drug with a solution of an acid capable of forming a pharmaceutically acceptable salt form of the basic drug, such as hydrochloric acid, iodic acid, fumaric acid, maleic acid, succinic acid, acetic acid, citric acid, tartaric acid, carbonic acid, phosphoric acid, sulfuric acid and the like. Typical anions for basic drugs, when in protonated form, include chloride, sulfate, bromide, mesylate, maleate, citrate and phosphate. Suitable pharmaceutically acceptable salt forms are found in, e.g., *Handbook of Pharmaceutical Salts: Properties, Selection and Use*, Weinheim/Zürich:Wiley-VCH/VHCA, 2002; P. H. Stahl and C. G. Wermuth, Eds.

As referred to herein, an "organic acid" is an organic molecule having at least one carboxylic acid group that generally possesses a molecular weight that is less than about 300 daltons. An organic acid may have 2 or more carboxylic acid groups, e.g., 2, 3, or 4, carboxylic acid groups. The organic acid may be aliphatic or aromatic, and may optionally contain additional non-basic substituents such as hydroxyl, ester, or the like. Aliphatic organic acids may also contain one or more elements of unsaturation, e.g., a double or a triple bond. Exemplary organic acids include ethanoic acid, propanoic acid, butanoic acid, pentanoic acid, benzoic acid, acetyl salicylic acid, citric acid, fumaric acid, maleic acid, salicylic acid, succinic acid, oxalic acid, malonic acid, glutaric acid, adipic acid, pimelic acid, and so forth.

"Polyorthoester-compatible" refers to, in one particular aspect of the properties of the polyorthoester, the properties of an excipient which, when mixed with the polyorthoester, forms a single phase and does not cause any chemical changes to the polyorthoester.

A "therapeutically effective amount" means the amount that, when administered to a human or an animal for treatment of a disease, is sufficient to effect treatment for that disease or condition.

"Treating" or "treatment" of a disease or condition includes preventing the disease or condition from occurring in a human or an animal that may be predisposed to the disease or condition but does not yet experience or exhibit symptoms of the disease or condition (prophylactic treatment), inhibiting the disease or condition (slowing or arresting its development), providing relief from the symptoms or side-effects of the disease or condition (including palliative treatment), and relieving the disease or condition (causing regression of the disease).

As used herein, "synergistic" when used in relation to the combination refers to a combination that allows a lower amount of analgesic agent (amide-type local anesthetic) and, in some embodiments, also a lower amount of NSAID, than would be required to achieve a given level of analgesia or pain relief if the amide-type local anesthetic or NSAID were administered alone. The synergistic combination may allow a lower amount of amide-type local anesthetic and NSAID to be administered in a single dose to provide a given level of analgesia or pain relief than if the amide-type local anesthetic or NSAID were administered alone thereby providing a greater than additive analgesic effect in combination. In some instances, the lower amount of the amide or anilide-type local anesthetic and NSAID is a sub-analgesic amount in which one or both of the components of the combination are administered at a dosage normally considered not to provide an analgesic or pain relief effect.

Alternatively, the term "synergistic" when used in relation to the combination refers to a combination that extends the duration or degree of the analgesic or pain relief effect beyond the duration observed when either the amide-type local anesthetic or the NSAID is administered alone. In this instance, the amount of amide-type local anesthetic and/or the NSAID may be the same as the amount normally provided in a single dose to achieve analgesia, thereby allowing a lower amount of amide or anilide-type local anesthetic and NSAID to be administered over the course of multiple doses of analgesic or pain relief therapy as dosing is less frequent a allowing greater analgesia or pain relief than would otherwise be achievable with a given dose of amide-type local anesthetic or NSAID.

"Optional" or "optionally" means that the subsequently described circumstance may or may not occur, so that the description includes instances where the circumstance occurs and instances where it does not.

The term "substantially" in reference to a certain feature or entity means to a significant degree or nearly completely (i.e. to a degree of 85% or greater) in reference to the feature or entity.

The term "about," particularly in reference to a given quantity, is meant to encompass deviations of plus or minus 5%, 10%, 15% or 20%.

Additional definitions may also be found in the sections which follow.

II. Compositions and Methods of Use

Currently available local anesthetic formulations used to manage post-operative pain generally don't work particularly well after 24 hours—i.e., they are short acting in nature. In exploring the use of semi-solid compositions of amide-type anesthetics such as bupivacaine or ropivacaine (in free base form) with a model delivery vehicle in the form of a polyorthoester as a local anesthetic for treating post-operative pain, it was observed that some of the compositions, while effective immediately after application to the surgical site (for a period of up to about 5 hours post-application or even over the first 24 hours or so), diminished in their efficacy when considered in the days following surgery. More specifically, compositions comprising bupivacaine or ropivacaine as the only active agent in a delivery vehicle generally resulted in significantly diminished efficacy over the period from about 1-3 days post-surgery, when compared to their efficacy in the short-term (e.g., from about 1-5 hours or so following application) (see FIG. 3). However plasma concentrations of the corresponding compositions containing only bupivacaine or ropivacaine demonstrate a relatively constant plasma concentration over the same period indicating drug release is relatively constant (see FIG. 1A). While exploring ways in which to provide more effective, long-acting compositions comprised of an amide local anesthetic, the Applicants discovered that the incorporation of an NSAID into the composition, e.g., an enolic-acid NSAID, was extremely effective in altering the pharmacodynamics of the resulting compositions. While a small drop in efficacy was still observed for the resulting composition from about 5 hours to 24 hours post-application (see FIG. 4 and FIGS. 4 and 5A-5B), interestingly, the efficacy of the composition increased beyond the efficacy achieved with compositions comprised of amide-type local anesthetic as the sole active agent such that pain relief (i.e., efficacy) during the period from about 1 day or about 2 days to up to about 5 or 6 days following administration, and optionally longer, was similar to that provided in the first 5 hours post-administration. While this surprising and advantageous effect was observed for compositions comprising meloxicam, a similar recovery of efficacy was not observed for composition comprising the same amide-type local anesthetic and 7.5 wt % of a different chemical class of NSAID, the heteroaryl acetic acid, diclofenac (see FIG. 4). Moreover, the degree of efficacy restored and provided by the composition composed of amide-type local anesthetic and enolic-acid NSAID in a delivery vehicle from about 2 days to at least about 5 days following administration was greater than the result expected by the mere addition of the enolic-acid NSAID to the formulation; that is, the amide-type local anesthetic and the enolic-acid NSAID act synergistically rather than additively. See, e.g., the results provided in FIG. 4 discussed below.

Thus, in one embodiment, the Applicants have discovered that the addition of an enolic-acid NSAID to compositions comprising an amide type local anesthetic and a delivery vehicle is effective to (i) modify a short-acting, anesthetic formulation into one effective to provide long-lasting pain relief, over a period of at least about 3-5 days, (ii) provide a degree of pain relief that is greater than expected, based upon the mere additive effect of the drugs, i.e., a synergistic effect, and (iii) provide measurable plasma concentrations of both the amide-type local anesthetic and the NSAID for a period of at least about 5 days following administration, among having other beneficial features.

Accordingly, the systems and compositions described herein generally comprise an amide-type local anesthetic, an enolic-acid NSAID and a delivery vehicle. The long-acting compositions and systems find use, for example, as drug delivery systems or as medical or surgical devices, e.g., for treatment of pain, such as post-operative pain. The composition components are described below, e.g., in Examples 1-8.

In another embodiment, Applicants have discovered that use of a triglyceride solvent in compositions comprising a polyorthoester delivery vehicle and an active agent provides a substantial reduction in viscosity of the composition, relative to a similar composition absent the triglyceride solvent, without altering the release kinetics of the active agent(s) from the composition or altering the pharmokinetic profile of the active agent(s), relative to that of a composition absent the triglyceride solvent. The reduced viscosity of the compositions offers significant clinical advantages in terms of ease of administration via needle delivery at room temperature. Exemplary compositions demonstrating these unexpected findings are described below, e.g, in Examples 9-15.

1. Compositions for Analgesia

In one aspect, compositions comprising an amide-type local anesthetic, an enolic-acid non-steroidal anti-inflammatory drug (NSAID) and a delivery vehicle are provided. In this section, each of the composition components is described.

Amide-Type Local Anesthetic

The composition comprises a local anesthetic of the amide type. Local anesthetics belonging to this class include bupivacaine, levobupivacaine, dibucaine, mepivacaine, procaine, lidocaine, tetracaine, ropivacaine, and the like. These compounds are alkaline-amides possessing pKb values ranging from 5.8 to 6.4. That is, the drugs contain protonizable tertiary amine functions. For example, the pKa values of ropivacaine, lidocaine, and bupivacaine are 8.1, 7.7 and 8.1, respectively. The amide-type drugs are provided in the compositions either in their neutral, base form or as their corresponding acid-addition salts, or as a mixture of both forms.

In one embodiment, the amide type local anesthetic is added to the composition in its free base form. The amide-type anesthetic may be provided as a racemic mixture, i.e., containing equal amounts of the R and S enantiomers, or may be provided as a single enantiomer, or may be provided as an unequal mixture of enantiomers in which one enantiomer is in excess.

In one particular embodiment, the composition comprises bupivacaine as the local anesthetic. In a further embodiment, the composition comprises as the active agent ropivacaine.

In yet one or more additional embodiments, the composition comprises any one or more of the amide-type local anesthetics described above such as, for example, levobupivacaine, dibucaine, mepivacaine, procaine, lidocaine, tetracaine, and the like. In still another embodiment, the amide-type local anesthetic is selected from the group consisting of bupivacaine, ropivacaine, levobupivacaine, dibucaine, mepivacaine, procaine, lidocaine, and tetracaine.

The composition may also comprise in addition to the amide-type local anesthetic and the enolic acid NSAID (described below), one or more additional bioactive agents.

The amide-type local anesthetic is dissolved or dispersed into the composition as provided herein. The concentration of the amide-type local anesthetic in the composition may vary from about 1 wt % to 30 wt %, 1 wt % to 10 wt %, 10 wt % to 20 wt %, 2 wt % to 5 wt %, 10 wt % to 15 wt %, or 15 wt % to 20 wt % and may be 1 wt %, 1.1 wt %, 1.2 wt %, 1.3 wt %, 1.4 wt %, 1.5 wt %, 1.6 wt %, 1.7 wt %, 1.8 wt %, 1.9 wt %, 2 wt %, 2.1 wt %, 2.2 wt %, 2.3 wt %, 2.4 wt %, 2.5 wt %, 2.6 wt %, 2.7 wt %, 2.8 wt %, 2.9 wt %, 3 wt %, 3.1 wt %, 3.2 wt %, 3.3 wt %, 3.4 wt %, 3.5 wt %, 3.6 wt %, 3.7 wt %, 3.8 wt %, 3.9 wt %, 4 wt %, 4.1 wt %, 4.2 wt %, 4.3 wt %, 4.4 wt %, 4.5 wt %, 4.6 wt %, 4.7 wt %, 4.8 wt %, 4.9 wt %, 5 wt %, 5 wt %, 5.1 wt %, 5.2 wt %, 5.3 wt %, 5.4 wt %, 5.5 wt %, 5.6 wt %, 5.7 wt %, 5.8 wt %, 5.9 wt %, 6 wt %, 6.1 wt %, 6.2 wt %, 6.3 wt %, 6.4 wt %, 6.5 wt %, 6.6 wt %, 6.7 wt %, 6.8 wt %, 6.9 wt %, 7 wt %, 7.1 wt %, 7.2 wt %, 7.3 wt %, 7.4 wt %, 7.5 wt %, 7.6 wt %, 7.7 wt %, 7.8 wt %, 7.9 wt %, 8 wt %, 8.1 wt %, 8.2 wt %, 8.3 wt %, 8.4 wt %, 8.5 wt %, 8.6 wt %, 8.7 wt %, 8.8 wt %, 8.9 wt %, 9 wt %, 9.1 wt %, 9.2 wt %, 9.3 wt %, 9.4 wt %, 9.5 wt %, 9.6 wt %, 9.7 wt %, 9.8 wt %, 9.9 wt %, 10 wt %, 11 wt %, 11.1 wt %, 11.2 wt %, 11.3 wt %, 11.4 wt %, 11.5 wt %, 11.6 wt %, 11.7 wt %, 11.8 wt %, 11.9 wt %, 12 wt %, 12.1 wt %, 12.2 wt %, 12.3 wt %, 12.4 wt %, 12.5 wt %, 12.6 wt %, 12.7 wt %, 12.8 wt %, 12.9 wt %, 13 wt %, 13.1 wt %, 13.2 wt %, 13.3 wt %, 13.4 wt %, 13.5 wt %, 13.6 wt %, 13.7 wt %, 13.8 wt %, 13.9 wt %, 14 wt %, 14.1 wt %, 14.2 wt %, 14.3 wt %, 14.4 wt %, 14.5 wt %, 14.6 wt %, 14.7 wt %, 14.8 wt %, 14.9 wt %, 15 wt %, 15 wt %, 15.1 wt %, 15.2 wt %, 15.3 wt %, 15.4 wt %, 5.5 wt %, 15.6 wt %, 15.7 wt %, 15.8 wt %, 15.9 wt %, 16 wt %, 16.1 wt %, 16.2 wt %, 16.3 wt %, 16.4 wt %, 16.5 wt %, 16.6 wt %, 16.7 wt %, 16.8 wt %, 16.9 wt %, 17 wt %, 17.1 wt %, 17.2 wt %, 17.3 wt %, 17.4 wt %, 17.5 wt %, 17.6 wt %, 17.7 wt %, 17.8 wt %, 17.9 wt %, 18 wt %, 18.1 wt %, 18.2 wt %, 18.3 wt %, 18.4 wt %, 18.5 wt %, 18.6 wt %, 18.7 wt %, 18.8 wt %, 18.9 wt %, 19 wt %, 19.1 wt %, 19.2 wt %, 19.3 wt %, 19.4 wt %, 19.5 wt %, 19.6 wt %, 19.7 wt %, 19.8 wt %, 19.9 wt %, 20 wt %, 21 wt %, 22 wt %, 23 wt %, 24 wt %, 25 wt %, 26 wt %, 27 wt %, 28 wt %, 29 wt % and 30 wt %.

In one embodiment, the amide-type local anesthetic is present in the composition at between about 0.01 wt % and about 7.5 wt %. In another embodiment, the amide-type local anesthetic is present in the composition at between about 0.1 wt % and about 7.5 wt %, or between about 0.1 wt % and about 5.5 wt %, or between about 0.25 wt % and about 5.2 wt %, or between about 0.25 wt % and about 5.0 wt %.

Enolic-Acid Non-Steroidal Anti-Inflammatory Drug (NSAID)

The compositions, in some embodiments, provided herein additionally comprise an NSAID (non-steroidal anti-inflammatory drug). NSAIDs contemplated for use in the compositions include acetic acid derivatives, propionic acid derivatives, enolic acid derivatives and fenamic acid derivatives. Representative NSAIDS in these classes include, but are not limited to, the following acetic acid-type NSAIDs: diflunisal, indomethacin, tolmetin, sulindac, etodolac, ketorolac, diclofenac and nabumetone; the following propionic acid-type NSAIDs: ibuprofen, dexibuprofen, naproxen, fenoprofen, ketoprofen, dexketoprofen, flurbiprofen, oxaprozin, and loxoprofen; fenamic acid-type NSAIDs: mefenamic acid, meclofenamic acid, flufenamic acid and tolfenamic acid.

In one embodiment, the NSAID in the composition is an enolic acid-type NSAID. As described herein, the incorporation of an enolic acid NSAID in the compositions is effective to alter the pharmacodynamic profile of the resulting composition, to thereby provide a composition that is generally effective to provide pain relief from about 1 day to at least about 5 days following application, in contrast to the short-acting nature of the composition absent the enolic-acid NSAID. Additional features of the composition are described elsewhere herein.

The NSAID included in the composition, i.e., the enolic-acid NSAID, does not comprise a carboxylic acid function as do most NSAIDs, but is weakly acidic in nature due to the presence of a vinylogous carboxylic acid that can undergo keto-enol tautomerism. Representative enolic-acid NSAIDs suitable for inclusion in the instant compositions include meloxicam, piroxicam, tenoxicam, droxicam, lornoxicam, and isoxicam. In a particular embodiment, the enolic-acid NSAID is meloxicam. One particularly particular composition comprises bupivacaine and meloxicam. Yet another particular composition comprises ropivacaine and meloxicam.

While not being bound in theory, it is believed that the incorporation of the enolic-acid NSAID is effective to reduce the inflammation that occurs as a result of a typical operative procedure, to thereby allow the amide-type anesthetic to provide effective local anesthesia. More specifically, it is believed that the slight drop of pH in tissues that often accompanies inflammation, e.g., in a post-operative patient, may be responsible for the inability of the amino-amide-type anesthetic to provide effective pain relief after about 5 hours or so. Due to the lag time in the inflammatory response, the local anesthetic is able to provide significant, short-term pain relief post-surgery. However, it is contemplated that once inflammation occurs to a degree effective to drop the pH of target tissues to a degree sufficient to prevent the amide-type local anesthetic from exerting its desired pharmacological effect, i.e., by impeding the ability of the anesthetic to be delivered to target nerves, the composition then becomes significantly less effective in its ability to provide effective pain relief. Thus, it is believed that the observed short-term effect of composition absent the NSAID is not strictly due to the inability of the composition to release the local anesthetic, but rather, is due to the inability of the released local anesthetic to exert its intended pharmacological effect. Interestingly, it appears that not all NSAIDs are effective in enhancing the effect of a locally administered amide-type anesthetic. As described in Example 7, an illustrative composition comprising a polyorthoester as a delivery vehicle and bupivacaine and 7.5 wt % diclofenac (having a proton-donating carboxylic acid group) failed to regain its short-term efficacy after about 1 day following application or more, and provided significantly less pain relief over the time frame of 1 to 5 days following application when compared to its early, short-term efficacy up to about 5 hours post-application. This is in distinct contrast to the bupivacaine-meloxicam composition.

The enolic-acid NSAID is dissolved or dispersed into the composition as provided herein. The concentration of the enolic-acid NSAID such as meloxicam may vary in the composition from about 0.01 wt % to 10 wt %, 0.01 wt % to 5 wt %, 0.01 wt % to 3 wt %, 0.01 wt % to 1 wt %, 0.10 wt % to 10 wt %, 0.1 wt % to 5 wt %, 0.1 wt % to 3 wt %, 0.1 wt % to 1 wt %, and may be 0.01 wt %, 0.011 wt %, 0.012 wt %, 0.013 wt %, 0.014 wt %, 0.015 wt %, 0.016 wt %, 0.017 wt %, 0.018 wt %, 0.019 wt %, 0.02 wt %, 0.021 wt %, 0.022 wt %, 0.023 wt %, 0.024 wt %, 0.025 wt %, 0.026 wt %, 0.027 wt %, 0.028 wt %, 0.029 wt %, 0.030 wt %, 0.031 wt %, 0.032 wt %, 0.033 wt %, 0.034 wt %, 0.035 wt %, 0.036 wt %, 0.037 wt %, 0.038 wt %, 0.039 wt %, 0.040 wt %, 0.041 wt %, 0.042 wt %, 0.043 wt %, 0.044 wt %, 0.045 wt %, 0.046 wt %, 0.047 wt %, 0.048 wt %, 0.049 wt %, 0.05 wt %, 0.051 wt %, 0.052 wt %, 0.053 wt %, 0.054 wt %, 0.055 wt %, 0.056 wt %, 0.057 wt %, 0.058 wt %, 0.059 wt %, 0.06 wt %, 0.061 wt %, 0.062 wt %, 0.063 wt %, 0.064 wt %, 0.065 wt %, 0.066 wt %, 0.067 wt %, 0.068 wt %, 0.069 wt %, 0.07 wt %, 0.071 wt %, 0.072 wt %, 0.073 wt %, 0.074 wt %, 0.075 wt %, 0.076 wt %, 0.077 wt %, 0.078 wt %, 0.079 wt %, 0.08 wt %, 0.081 wt %, 0.082 wt %, 0.083 wt %, 0.084 wt %, 0.085 wt %, 0.086 wt %, 0.087 wt %, 0.088 wt %, 0.089 wt %, 0.09 wt %, 0.091 wt %, 0.092 wt %, 0.093 wt %, 0.094 wt %, 0.095 wt %, 0.096 wt %, 0.097 wt %, 0.098 wt %, 0.099 wt %, 0.1 wt %, 0.11 wt %, 0.12 wt %, 0.13 wt %, 0.14 wt %, 0.15 wt %, 0.16 wt %, 0.17 wt %, 0.18 wt %, 0.19 wt %, 0.2 wt %, 0.21 wt %, 0.22 wt %, 0.23 wt %, 0.24 wt %, 0.25 wt %, 0.26 wt %, 0.27 wt %, 0.28 wt %, 0.29 wt %, 0.30 wt %, 0.31 wt %, 0.32 wt %, 0.33 wt %, 0.34 wt %, 0.35 wt %, 0.36 wt %, 0.37 wt %, 0.38 wt %, 0.39 wt %, 0.40 wt %, 0.41 wt %, 0.42 wt %, 0.43 wt %, 0.44 wt %, 0.45 wt %, 0.46 wt %, 0.47 wt %, 0.48 wt %, 0.49 wt %, 0.5 wt %, 0.5.1 wt %, 0.52 wt %, 0.53 wt %, 0.54 wt %, 0.55 wt %, 0.56 wt %, 0.57 wt %, 0.58 wt %, 0.59 wt %, 0.6 wt %, 0.61 wt %, 0.62 wt %, 0.63 wt %, 0.64 wt %, 0.65 wt %, 0.66 wt %, 0.67 wt %, 0.68 wt %, 0.69 wt %, 0.7 wt %, 0.71 wt %, 0.72 wt %, 0.73 wt %, 0.74 wt %, 0.75 wt %, 0.76 wt %, 0.77 wt %, 0.78 wt %, 0.79 wt %, 0.8 wt %, 0.81 wt %, 0.82 wt %, 0.83 wt %, 0.84 wt %, 0.85 wt %, 0.86 wt %, 0.87 wt %, 0.88 wt %, 0.89 wt %, 0.9 wt %, 0.91 wt %, 0.92 wt %, 0.93 wt %, 0.94 wt %, 0.95 wt %, 0.96 wt %, 0.97 wt %, 0.98 wt %, 0.99 wt %, 1.0 wt %, 1.01 wt %, 1.02 wt %, 1.03 wt %, 1.04 wt %, 1.05 wt %, 1.06 wt %, 1.07 wt %, 1.08 wt %, 1.09 wt %, 1.1 wt %, 1.11 wt %, 1.12 wt %, 1.13 wt %, 1.14 wt %, 1.15 wt %, 1.16 wt %, 1.17 wt %, 1.18 wt %, 1.19 wt %, 1.2 wt %, 1.21 wt %, 1.22 wt %, 1.23 wt %, 1.24 wt %, 1.25 wt %, 1.26 wt %, 1.27 wt %, 1.28 wt %, 1.29 wt %, 1.30 wt %, 1.31 wt %, 1.32 wt %, 1.33 wt %, 1.34 wt %, 1.35 wt %, 1.36 wt %, 1.37 wt %, 1.38 wt %, 1.39 wt %, 1.40 wt %, 1.41 wt %, 1.42 wt %, 1.43 wt %, 1.44 wt %, 1.45 wt %, 1.46 wt %, 1.47 wt %, 1.48 wt %, 1.49 wt %, 1.5 wt %, 1.5.1 wt %, 1.52 wt %, 1.53 wt %, 1.54 wt %, 1.55 wt %, 1.56 wt %, 1.57 wt %, 1.58 wt %, 1.59 wt %, 1.6 wt %, 1.61 wt %, 1.62 wt %, 1.63 wt %, 1.64 wt %, 1.65 wt %, 1.66 wt %, 1.67 wt %, 1.68 wt %, 1.69 wt %, 1.7 wt %, 1.71 wt %, 1.72 wt %, 1.73 wt %, 1.74 wt %, 1.75 wt %, 1.76 wt %, 1.77 wt %, 1.78 wt %, 1.79 wt %, 1.8 wt %, 1.81 wt %, 1.82 wt %, 1.83 wt %, 1.84 wt %, 1.85 wt %, 1.86 wt %, 1.87 wt %, 1.88 wt %, 1.89 wt %, 1.9 wt %, 1.91 wt %, 1.92 wt %, 1.93 wt %, 1.94 wt %, 1.95 wt %, 1.96 wt %, 1.97 wt %, 1.98 wt %, 1.99 wt %, 2.00 wt %, 2.01 wt %, 2.02 wt %, 2.03 wt %, 2.04 wt %, 2.05 wt %, 2.06 wt %, 2.07 wt %, 2.08 wt %, 2.09 wt %, 2.1 wt %, 2.11 wt %, 2.12 wt %, 2.13 wt %, 2.14 wt %, 2.15 wt %, 2.16 wt %, 2.17 wt %, 2.18 wt %, 2.19 wt %, 2.20 wt %, 2.21 wt %, 2.22 wt %, 2.23 wt %, 2.24 wt %, 2.25 wt %, 2.26 wt %, 2.27 wt %, 2.28 wt %, 2.29 wt %, 2.30 wt %, 2.31 wt %, 2.32 wt %, 2.33 wt %, 2.34 wt %, 2.35 wt %, 2.36 wt %, 2.37 wt %, 2.38 wt %, 2.39 wt %, 2.40 wt %, 2.41 wt %, 2.42 wt %, 2.43 wt %, 2.44 wt %, 2.45 wt %, 2.46 wt %, 2.47 wt %, 2.48 wt %, 2.49 wt %, 2.5 wt %, 2.5.1 wt %, 2.52 wt %, 2.53 wt %, 2.54 wt %, 2.55 wt %, 2.56 wt %, 2.57 wt %, 2.58 wt %, 2.59 wt %, 2.6 wt %, 2.61 wt %, 2.62 wt %, 2.63 wt %, 2.64 wt %, 2.65 wt %, 2.66 wt %, 2.67 wt %, 2.68 wt %, 2.69 wt %, 2.7 wt %, 2.71 wt %, 2.72 wt %, 2.73 wt %, 2.74 wt %, 2.75 wt %, 2.76 wt %, 2.77 wt %, 2.78 wt %, 2.79 wt %, 2.8 wt %, 2.81 wt %, 2.82 wt %, 2.83 wt %, 2.84 wt %, 2.85 wt %, 2.86 wt %, 2.87 wt %, 2.88 wt %, 2.89 wt %, 2.9 wt %, 2.91 wt %, 2.92 wt %, 2.93 wt %, 2.94 wt %, 2.95 wt %, 2.96 wt %, 2.97 wt %, 2.98 wt %, 2.99 wt %, 3.0 wt %, 3.01 wt %, 3.02 wt %, 3.03 wt %, 3.04 wt %, 3.05 wt %, 3.06 wt %, 3.07 wt %, 3.08 wt %, 3.09 wt %, 3.1 wt %, 3.11 wt %, 3.12 wt %, 3.13 wt %, 3.14 wt %, 3.15 wt %, 3.16 wt %, 3.17 wt %, 3.18 wt %, 3.19 wt %, 3.20 wt %, 3.21 wt %, 3.22 wt %, 3.23 wt %, 3.24 wt %, 3.25 wt %, 3.26 wt %, 3.27 wt %, 3.28 wt %, 3.29 wt %, 3.30 wt %, 3.31 wt %, 3.32 wt %, 3.33 wt %, 3.34 wt %, 3.35 wt %, 3.36 wt %, 3.37 wt %, 3.38 wt %, 3.39 wt %, 3.40 wt %, 3.41 wt %, 3.42 wt %, 3.43 wt %, 3.44 wt %, 3.45 wt %, 3.46 wt %, 3.47 wt %, 3.48 wt %, 3.49 wt %, 3.5 wt %, 3.5.1 wt %, 3.52 wt %, 3.53 wt %, 3.54 wt %, 3.55 wt %, 3.56 wt %, 3.57 wt %, 3.58 wt %, 3.59 wt %, 3.6 wt %, 3.61 wt %, 3.62 wt %, 3.63 wt %, 3.64 wt %, 3.65 wt %, 3.66 wt %, 3.67 wt %, 3.68 wt %, 3.69 wt %, 3.7 wt %, 3.71 wt %, 3.72 wt %, 3.73 wt %, 3.74 wt %, 3.75 wt %, 3.76 wt %, 3.77 wt %, 3.78 wt %, 3.79 wt %, 3.8 wt %, 3.81 wt %, 3.82 wt %, 3.83 wt %, 3.84 wt %, 3.85 wt %, 3.86 wt %, 3.87 wt %, 3.88 wt %, 3.89 wt %, 3.9 wt %, 3.91 wt %, 3.92 wt %, 3.93 wt %, 3.94 wt %, 3.95 wt %, 3.96 wt %, 3.97 wt %, 3.98 wt %, 3.99 wt %, 4.0 wt %, 4.25 wt %, 4.5 wt %, 4.75 wt %, 5.0 wt %, 5.25 wt %, 5.5 wt %, 5.75 wt %, 6.0 wt %, 6.25 wt %, 6.5 wt %, 6.75 wt %, 7.0 wt %, 7.25 wt %, 7.5 wt %, 7.75 wt %, 8.0 wt %, 8.25 wt %, 8.5 wt %, 8.75 wt %, 9.0 wt %, 9.25 wt %, 9.5 wt %, 9.75 wt %, or 10.0 wt %.

In one embodiment, the composition comprises an enolic-acid NSAID in an amount above about 0.01 wt % of the composition, above about 0.025 wt %, about 0.05 wt %, above about 0.1 wt % of the composition, or above about 0.25 wt %, or between about 0.01-10 wt %, or between about 0.01-7.5 wt %, or between about 0.01-5.0 wt %, or between about 0.01-3.5 wt %.

Exemplary Delivery Vehicles

The composition additionally comprises a delivery vehicle. In one embodiment, the delivery vehicle is a sustained-release vehicle, and exemplary vehicles include polymeric formulations, liposomes, microspheres, implantable device or non-polymeric formulations. Examples of these vehicles will now be described.

Liposomes

Liposomes are small vesicles composed of lipids arranged in spherical bilayers. Liposomes are usually classified as small unilamellar vesicles (SUV), large unilamellar vesicles (LUV), multi-lamellar vesicles (MLV) or multivesicular liposomes (MVL). SUVs and LUVs, by definition, have only one bilayer, whereas MLVs contain many concentric bilayers (see, e.g., Stryer, Biochemistry, 2d Edition, W.H. Freeman & Co., p. 213 (1981)). MVLs were first reported by Kim et al. (Biochim, Biophys. Acta, 728:339-348, 1983) and contain multiple, non-concentric aqueous chambers per particle (See, U.S. Pat. Nos. 6,132,766 and 8,182,835, incorporated herein by reference in their entirety).

Liposomes suitable for use in the composition of the present invention include those composed primarily of vesicle-forming lipids. Vesicle-forming lipids can form spontaneously into bilayer vesicles in water, as exemplified by the phospholipids. The liposomes can also include other lipids incorporated into the lipid bilayers, e.g., cholesterol, with the hydrophobic moiety in contact with the interior, hydrophobic region of the bilayer membrane, and the head group moiety oriented toward the exterior, polar surface of the bilayer membrane.

The vesicle-forming lipids can have two hydrocarbon chains, typically acyl chains, and a head group, either polar or nonpolar. There are a variety of synthetic vesicle-forming lipids and naturally-occurring vesicle-forming lipids, including the phospholipids, such as phosphalidylcholine, phosphatidylethanolamine, phosphatidic acid, phosphatidylinositol, and sphingomyelin, where the two hydrocarbon chains are typically between about 14-22 carbon atoms in length, and have varying degrees of unsaturation. The above-described lipids and phospholipids whose acyl chains have varying degrees of saturation can be obtained commercially or prepared according to published methods. Other suitable lipids include glycolipids and sterols, such as cholesterol.

In one embodiment, the vesicle-forming lipid is selected to achieve a specified degree of fluidity or rigidity, to control the stability of the liposome in serum and to control the rate of release of the entrapped agent in the liposome. Liposomes may be prepared by a variety of techniques (see, e.g., Szoka, F., Jr., et al., Ann. Rev. Biophys. Bioeng. 9:467 (1980); U.S. Pat. No. 5,631,018). It will be appreciated that lipid-based delivery vehicles other than liposomes are contemplated, such as micelles and emulsions.

In one embodiment, the amide-type local anesthetic and the enolic-acid NSAID are entrapped in an aqueous space of the liposome or in a lipid layer of the liposome.

Microspheres/Microparticles/Microcapsules

In another embodiment, the delivery vehicle is a microspheres, microparticles or microcapsules. Microspheres in the form of spherical polymer matrices with interconnected pores in which an active agent is incorporated are described, for example, in U.S. Pat. No. 4,818,542. Microparticles comprised of one or more polymers in which the active agents are incorporated or associated can be fabricated from biodegradable or non-biodegradable polymers that are suitable for in vivo use, such as poly(vinylpyrrolidone) and poly(acrylamide). The microspheres or microparticles can be administered as part of a formulation that forms a depot in situ or as part of an implant. The active agents are released from the microspheres or microparticles in a controlled fashion, to provide the desired therapeutic efficacy. In one embodiment, the sustained-release delivery vehicle is a microsphere comprised of a bioerodible or biodegradable polymer. In another embodiment, the amide-type local anesthetic and the enolic-acid NSAID are entrapped in the microsphere.

Implantable Devices

Implantable devices with a reservoir in which the active agents are contained and controllably-released are known in the medical arts. In one embodiment, an osmotic, mechanical, or electromechanical device is provided for implantation and sustained release of the active agents. Examples of implantable devices are set forth in U.S. Pat. Nos. 7,655,254; 8,603,051; and 8,603,076 and US Publication No. 2003/0032947.

Non-Polymeric Formulations

The delivery vehicle can also take the form of a non-polymeric, pharmaceutically acceptable carrier. For example, the non-polymeric formulation can comprise sucrose acetate isobutyrate as a non-polymeric, pharmaceutically acceptable carrier and an optional solvent, such as benzyl alcohol. The non-polymeric formulation can be a liquid. This liquid, non-polymeric formulation provides sustained local anesthesia to a subject after administration for a period of about 24-36 hours, 36-48 hours, 48-60 hours, 60-72 hours, 3-4 days or 3-5 days. In one embodiment, the delivery vehicle is comprised of between about 50-80 wt % sucrose acetate isobutyrate and between about 5-25 wt % benzyl alcohol, alternatively between 55-75 wt % sucrose acetate isobutyrate and between about 15-25 wt % benzyl alcohol, with the remainder to 100 wt % being the active agents. Exemplary non-polymeric formulations of this type are described in EP 1809329, which is incorporated herein by reference in its entirety.

In some embodiments, the liquid non-polymeric carrier is a liquid carrier material having a viscosity of about less than 50,000 mPa-s at 37° C., measured using a viscometer. Alternatively, the carrier has a viscosity of less than about 10,000 mPa-s when measured at 37° C. using a viscometer. In another embodiment, the liquid non-polymeric carrier is a liquid carrier material having a viscosity of about less than 5,000 mPa-s at 37° C. In yet another embodiment, the liquid non-polymeric carrier is a liquid carrier material having a viscosity of about less than 2,500 mPa-s at 37° C.

In another embodiment, the non-polymeric formulation is an aqueous solution.

Polymeric Formulations

Exemplary polymeric formulations as the sustained-release delivery vehicle include those comprised of bioerodible or biodegradable polymers. The vehicle when comprised of a bioerodible or biodegradable polymer can be a solid or a semi-solid vehicle. Bioerodible and/or biodegradable polymers are known in the art, and include but are not limited to polylactides, polyglycolides, poly(lactic-co-glycolic acid) copolymers, polycaprolactones, poly-3-hydroxybutyrate, and polyorthoesters. Semisolid polymers exist either in a glassy or viscous liquid state. Semisolid polymers typically display a glass transition temperature (Tg) below room temperature. Below the Tg, semisolid polymers can be considered to exist in a glassy state, while above the Tg, the polyorthoester can be considered to exist in a liquid state. Semisolid polyorthoester polymers are not thermoplastic polymers.

In one embodiment, a bioerodible or biodegradable polymer is selected to provide a certain rate of degradation or erosion to achieve a desired release rate of the enolic acid-type NSAID and the amide- or anilide type anesthetic. The delivery vehicle and active agents can be formulated to provide a semi-solid or solid composition. By way of example, in one embodiment, a semi-solid delivery vehicle comprised of a polyorthoester is provided, and some examples are set forth herein. In another embodiment, the polymeric delivery vehicle forms an implant or depot in situ.

In another embodiment, a solid delivery vehicle comprised of a biodegradable or bioerodible polymer is provided, where the solid vehicle is in the form of a rod or disk. Rods and disks are suitable for implantation into a patient, and the biodegradable or bioerodible polymer in which the active agents are incorporated can formulated to tailor the release of active agent. For example, the rod or disk can be formulated from different polymers with different rates of biodegradability or polymers of differing molecular weights can be used, as well as additives or excipients can be added to active agent-polymer matrix to tailor the rate of agent release. The rod or disk can also comprise materials commonly used in sutures and/or capable of being used in sutures, including the biodegradable polymers noted above as well as polyglactin and copolymers of glycolide with trimethylene carbonate (TMC) (polyglyconate).

In one embodiment, the delivery vehicle is comprised of a polyorthoester.

Polyorthoesters useful for the compositions provided herein are generally composed of alternating residues resulting from reaction of a diketene acetal and a diol, where each adjacent pair of diketene acetal derived residues is separated by the residue of a reacted diol. The polyorthoester may comprise α-hydroxy acid-containing subunits, i.e., subunits derived from an α-hydroxy acid or a cyclic diester thereof, such as subunits comprising glycolide, lactide, or combinations thereof, i.e., poly(lactide-co-glycolide), including all ratios of lactide to glycolide, e.g., 75:25, 65:35, 50:50, etc. Such subunits are also referred to as latent acid subunits; these latent acid subunits also fall within the more general "diol" classification as used herein, due to their terminal hydroxyl groups. Polyorthoesters can be prepared as described, for example, in U.S. Pat. Nos. 4,549,010 and 5,968,543. Exemplary polyorthoesters suitable for use in the compositions provided herein are described in U.S. Pat. No. 8,252,304.

The mole percentage of α-hydroxy acid containing subunits, $R^1$, generally ranges from 0 to 20 mol % of the total diol components ($R^1$ and $R^3$ as provided below). In one or more embodiments, the mole percentage of α-hydroxy acid containing subunits in the polyorthoester formulation is at least about 0.01 mole percent. Exemplary percentages of α-hydroxy acid containing subunits in the polymer are from about 0 to about 50 mole percent, or from about 0 to about 25 mole percent, or from about 0.05 to about 30 mole percent, or from about 0.1 to about 25 mole percent. For example, in one embodiment, the percentage of α-hydroxy acid containing subunits in the polymer is from about 0 to about 50 mole percent. In another embodiment, the percentage of α-hydroxy acid containing subunits in the polymer is from about 0 to about 25 mole percent. In yet another particular embodiment, the percentage of α-hydroxy acid containing subunits in the polymer is from about 0.05 to about 30 mole percent. In yet another embodiment, the percentage of α-hydroxy acid containing subunits in the polymer is from about 0.1 to about 25 mole percent. As an illustration, the percentage of α-hydroxy acid containing subunits may be 0, 1, 2, 3, 4, 5, 6, 7, 8, 9, 10, 11, 12, 13, 14, 15, 16, 17, 18, 19, 20, 21, 22, 23, 24, 24, 26, 27, 28, 29 or 30 mole percent, including any and all ranges lying therein, formed by combination of any one lower mole percentage number with any higher mole percentage number.

More particularly, a poly(orthoester) for use in the compositions and delivery systems provided herein is described by the following formula:

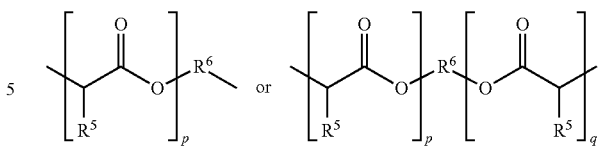

where: $R^*$ is a $C_{1-4}$ alkyl (e.g., C1, C2, C3 or C4 alkyl), n is an integer ranging from 5 to 400, and A in each subunit is $R^1$ or $R^3$. That is, in any monomer unit

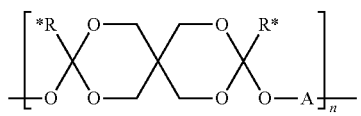

of the polymer of Formula I, A may be either $R^1$ or $R^3$.

In a particular embodiment, $R^*$ is ethyl (i.e., C2 alkyl). A subunit in accordance with formula I, wherein $R^*$ is ethyl, corresponds to a subunit resulting from reaction of a diol as provided herein with 3,9-di(ethylidene)-2,4,8,10-tetraoxaspiro[5.5]undecane (DETOSU), a diketene acetal having the structure:

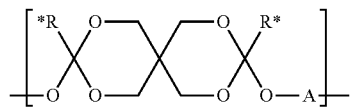

In reference to Formula I, as described previously, A may correspond to $R^1$. $R^1$ is

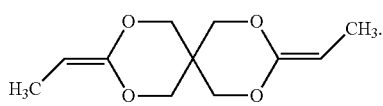

where p and q are each independently integers that range from between about 1 to 20 (e.g., are each independently selected from 1, 2, 3, 4, 5, 6, 7, 8, 9, 10, 11, 12, 13, 14, 15, 16, 17, 18, 19, and 20), each $R^5$ is independently hydrogen or $C_{1-4}$ alkyl (e.g., is H, or C1, C2, C3, or C4 alkyl); and $R^6$ is:

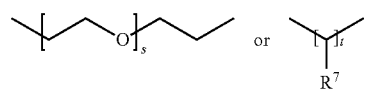

where s is an integer from 0 to 10 (e.g., is selected from, 0, 1, 2, 3, 4, 5, 6, 7, 8, 9, 10); t is an integer from 2 to 30; and $R^7$ is hydrogen or $C_{1-4}$ alkyl (e.g., is H or C1, C2, C3, or C4 alkyl). In one or more particular embodiments, $R^7$ is H. The $R^1$ subunits are α-hydroxy acid-containing subunits, i.e., subunits derived from an α-hydroxy acid or a cyclic diester thereof.

In reference to Formula I, A may also correspond to $R^3$, where $R^3$ is:

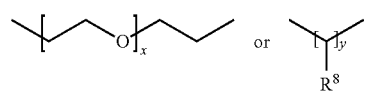

and x is an integer ranging from 1 to 100, and is, in certain particular instances, selected from 1, 2, 3, 4, and 5; y is an integer in a range from 2 to 30; and $R^8$ is hydrogen or $C_{1-4}$ alkyl (C1, C2, C3 or C4 alkyl).

In a particular embodiment, $R^8$ is H.

In some embodiments, the poly(orthoester) is one in which A is $R^1$ or $R^3$, where $R^1$ is

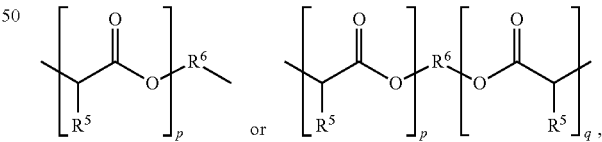

where p and q are each independently integers that range from between about 1 and 20, where the average number of p or the average number of the sum of p and q (p+q) is between about 1 and 7 (e.g., 1, 2, 3, 4, 5, 6, 7) when $R^1$ is present in the poly(orthoester) polymer; x and s are each independently an integer ranging from 0 to 10; and t and y are each independently an integer ranging from 2 to 30. In one or more particular embodiments, $R^5$ is H.

Additional particular poly(orthoesters) are those in which A is $R^1$ or $R^3$, where $R^1$ is

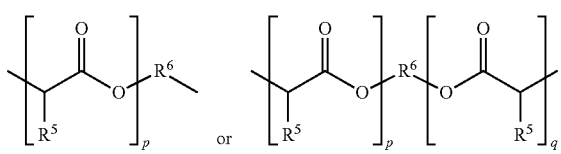

and p and q are each independently integers that vary from between about 1 and 20, or between about 1 and 15, or between about 1 and 10, where the average number of p or the average number of the sum of p and q (i.e., p+q) is between about 1 and 7 when R1 is present in the poly (orthoester) polymer. Additionally, particular ranges of x and s (in reference to the particular embodiment above or in reference to any polyorthoester as provided herein) are those in which each is independently an integer ranging from 0 to 7 or from 1 to 5. Similarly, particular ranges for t and y are those in which each independently varies from 2 to 10.

Particular polyorthoesters are those in which $R^5$ is hydrogen or methyl.

In certain particular embodiments, s and x are each independently selected from 1, 2, 3, 4, 5, 6, 7 and 8. In some particular embodiments, s is 2. In some other particular embodiments, x is 2.

An exemplary polyorthoester comprises alternating residues of 3,9-diethyl-3,9-2,4,8,10-tetraoxaspiro[5.5]undecane-3,9-diyl and A:

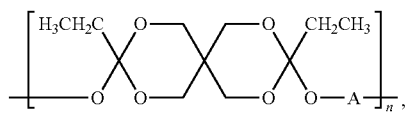

where A is as described above.

Polyorthoesters such as those described herein can be prepared by reacting an illustrative diketene acetal, 3,9-di (ethylidene)-2,4,8,10-tetraoxaspiro[5.5]undecane (DETOSU),

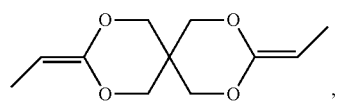

with one or more diols as described above, such as HO—$R^1$—OH or HO—$R^3$—OH. Illustrative diols include oligoethylene glycols such as triethylene glycol (TEG), oligoethylene glycols modified at one or both termini with an α-hydroxy acid such as an oligoethylene glycol diglycolide or an oligoethylene glycol dilactide, organic diols having a hydrocarbyl core of from 2 to 30 carbon atoms such as 1,6-hexanediol, 1,10-decanediol, cis/trans 1,4-cyclohexane dimethanol, para-menthane-3,8-diol, 1,4-butanediol, 1,5-pentanediol, 1,7-heptanediol, 1,8-octanediol, 1,10-decanediol, 1,12-dodecanediol, and cyclic equivalents thereof, where the hydroxyl groups can be at any two positions within the cycloalkyl or alkylene ring. An organic diol can possess from 2 to 20 carbon atoms. The organic diol can be linear, branched or cyclic, and may also be saturated or unsaturated. Generally, unsaturated diols will possess from 1-3 elements of unsaturation. A particular poly(orthoester) will contain from about from 10 to 50 total mole percent of subunits derived from one or more organic diols having a hydrocarbyl core.

Diols such as HO—$R^1$—OH are prepared as described in U.S. Pat. No. 5,968,543 and in Heller et al., *J. Polymer Sci., Polymer Letters Ed.* 18:293-297 (1980). For example, a diol of the formula HO—$R^1$-0H comprising a polyester moiety can be prepared by reacting a diol of the formula HO—$R^3$—OH with between 0.5 and 10 molar equivalents of a cyclic diester of an α-hydroxy acid such as lactide or glycolide, and allowing the reaction to proceed at 100-200° C. for about 12 hours to about 48 hours. Suitable solvents for the reaction include organic solvents such as dimethylacetamide, dimethyl sulfoxide, dimethylformamide, acetonitrile, pyrrolidone, tetrahydrofuran, and methylbutyl ether. Although the diol product is generally referred to herein as a discrete and simplified entity, e.g., TEG diglycolide (and diol reaction products such as TEG diglycolide), it will be understood by those of skill in the art that due to the reactive nature of the reactants, e.g., ring opening of the glycolide, the diol is actually a complex mixture resulting from the reaction, such that the term, TEG diglycolide (or any other term referring a similar product), generally refers to the average or overall nature of the product.

A particular polyorthoester is prepared by reacting 3,9-di (ethylidene)-2,4,8,10-tetraoxaspiro[5.5]undecane (DETOSU) with one or more reactive diols. Generally, the polyorthoester is prepared by reacting DETOSU with two or more reactive diols under anhydrous conditions. A particular polyorthoester is prepared by reacting DETOSU with triethylene glycol and triethylene glycol diglycolide as described in U.S. Pat. No. 8,252,305. A particular polyorthoester prepared from DETOSU-triethylene glycol-triethylene glycol diglycolide possesses the following molar ratios of components: 90:80:20, although the relative ratios of components can be suitably varied as described above.

A polyorthoester formed by the reaction of DETOSU with TEG and TEG diglycolide can generally be described as possessing the following subunits, where $R^1$ corresponds to the diolate portion derived from triethylene glycol diglycolide (formed by reaction of glycolide with TEG) and $R^3$ corresponds to the diolate portion derived from triethylene glycol:

where A is $R^1$, and $R^1$ is

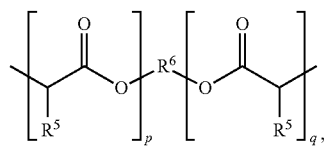

where $R^5$ is H and $R^6$ is

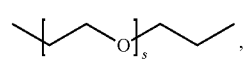

the resulting component of the polyorthoester is:

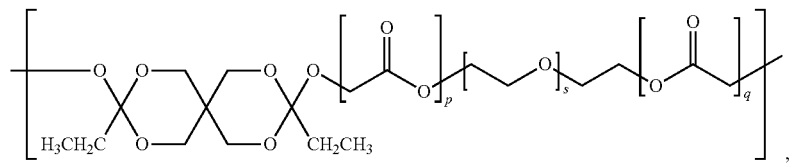

where the sum of p and q is, on average, 2 and s is 2; and when A is $R^3$, and $R^3$ is

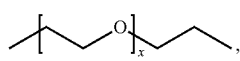

where x is 2, the resulting subunit or component of the polyorthoester is:

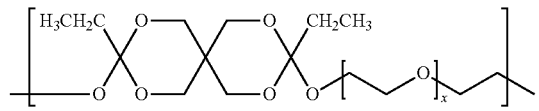

Structures corresponding to polyorthoesters prepared from the various α-hydroxy acid-containing subunits and additional diols described herein can be readily envisioned.

Exemplary polyorthoesters possess a weight average molecular weight of about 1000 Da to about 200,000 Da, for example from about 2,500 Da to about 100,000 Da or from about 3,500 Da to about 20,000 Da or from about 4,000 Da to about 10,000 Da or from about 5,000 Da to about 8,000 Da. Illustrative molecular weights, in Da, are 2500, 5000, 5500, 6000, 6500, 7000, 7500, 8000, 8500, 9000, 9500, 10,000, 20,000, 30,000, 40,000, 50,000, 60,000, 70,000, 80,000, 90,000, 100,000, 120,000, 150,000, 175,000 and 200,000, and ranges therein, wherein exemplary ranges include those formed by combining any one lower molecular weight as described above with any one higher molecular weight as provided above, relative to the selected lower molecular weight.

In one particular embodiment related to the polyorthoester in the delivery system, the polyorthoester has a molecular weight ranging from about 2,500 daltons to 10,000 daltons.

In one embodiment, the poly(orthoesters) described in this section are semi-solids both at room temperature and at temperatures above room temperature. In one embodiment, polyorthoesters containing 80 to 100 mole % $R^3$, where $R^3$ is

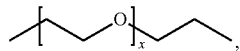

where x is 2, are semisolid polymers at both room temperature and at temperatures above room temperature. Semisolid polymers exist either in a glassy or viscous liquid state. Semisolid polymers typically display a glass transition temperature (Tg) below room temperature. Below the Tg, semi-solid polymers can be considered to exist in a glassy state, while above the Tg, the polyorthoester can be considered to exist in a liquid state. Semisolid polyorthoester polymers are not thermoplastic polymers.

Generally, polyorthoesters in accordance with any one of the following formulae, Formula I, Formula II, Formula III or Formula IV, are suitable for use in the compositions and/or delivery vehicles provided herein:

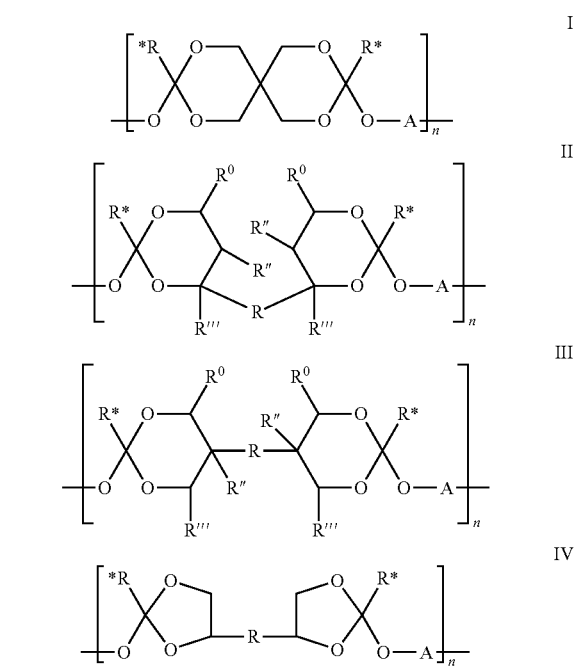

In reference to formulas I-IV,
R is a bond, $—(CH_2)_a—$, or $—(CH_2)_b—O—(CH_2)_c—$; where a is an integer from 1 to 12 (e.g., selected from 1, 2, 3, 4, 5, 6, 7, 8, 9, 10, 11, and 12), and b and c are independently integers from 1 to 5 (e.g., selected from 1, 2, 3, 4, and 5);
R* is a $C_{1-4}$ alkyl;
R°, R" and R'" are each independently H or $C_{1-4}$ alkyl;
n is an integer of at least 5; and
A is a diol.

For example, the compositions and delivery systems described herein may be comprised of a polyorthoester of Formula I, Formula II, Formula III or Formula IV, where: R is a bond, $—(CH_2)_a—$, or $—(CH_2)_b—O—(CH_2)_c—$; where a is an integer of 1 to 12, and b and c are independently integers of 1 to 5;
R* is a $C_{1-4}$ alkyl;
R°, R" and R'" are each independently H or $C_{1-4}$ alkyl;
n is an integer of at least 5; and
A is $R^1$, $R^2$, $R^3$, or $R^4$, where
$R^1$ is an α-hydroxy acid containing subunit as described in the preceding paragraphs;
$R^5$ is hydrogen or $C_{1-4}$ alkyl (e.g., methyl, ethyl, propyl, butyl, isopropyl, isobutyl, sec-butyl); and $R^6$ is selected from the group consisting of:

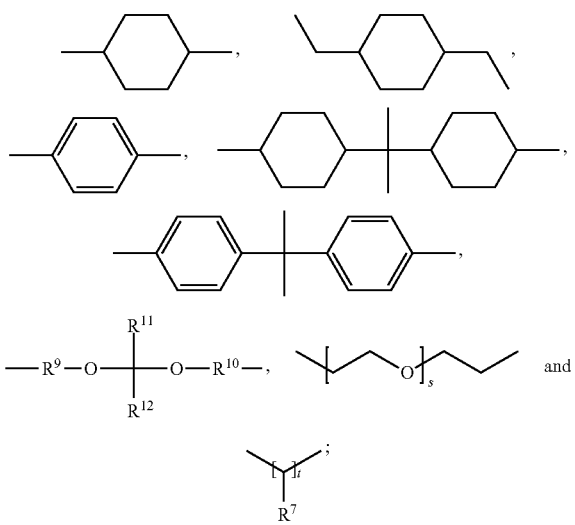

where:

s is an integer ranging from 0 to 10;

t is an integer ranging from 2 to 30; and $R^7$ is hydrogen or $C_{1-4}$ alkyl;

$R^2$ is:

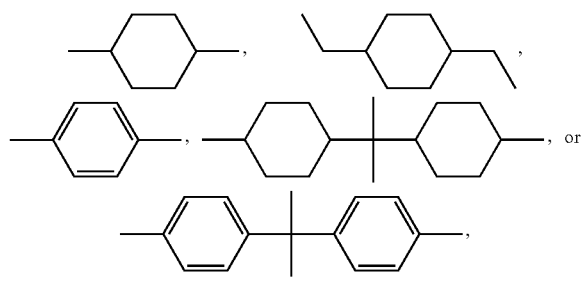

$R^3$ is:

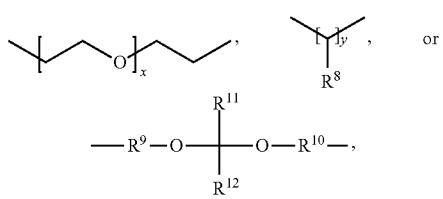

where:

x is an integer ranging from 0 to 200;

y is an integer ranging from 2 to 30;

$R^8$ is hydrogen or $C_{1-4}$ alkyl;

$R^9$ and $R^{10}$ are independently $C_{1-12}$ alkylene;

$R^{11}$ is hydrogen or $C_{1-6}$ alkyl and $R^{12}$ is $C_{1-6}$ alkyl; or $R^{11}$ and $R^{12}$ together are $C_{3-10}$ alkylene; and $R^4$ is the residue of a diol containing at least one functional group independently selected from an amide, an imide, a urea, and a urethane (carbmate) group.

In certain instances, the polyorthoester is one according to any one of Formulae I-IV in which A is $R^1$, $R^3$, or $R^4$, where $R^3$ is selected from:

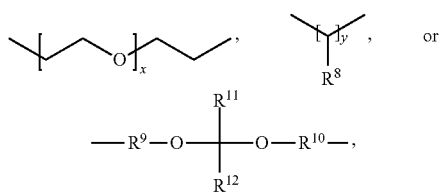

where:

x is an integer of 0 to 100;

y is an integer of 2 to 30;

$R^8$ is hydrogen or $C_{1-4}$ alkyl;

$R^9$ and $R^{10}$ are independently $C_{1-12}$ alkylene;

$R^{11}$ is hydrogen or $C_{1-6}$ alkyl and $R^{12}$ is $C_{1-6}$ alkyl; or $R^{11}$ and $R^{12}$ together are $C_{3-10}$ alkylene;

$R^4$ is a residual of a diol containing at least one functional group independently selected from amide, imide, urea and urethane groups; and $R^5$ is hydrogen or $C_{1-4}$ alkyl.

In one particular embodiment of the polyorthoester, the fraction of the A units that are of the formula $R^1$ is between 0 and 20 mole percent.

One exemplary polyorthoester is described by formula I, II, III or IV, where:

none of the units have A equal to $R^2$;

$R^3$ is:

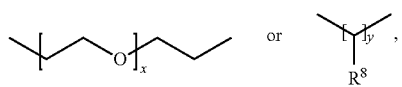

where:

x is an integer of 1 to 100;

y is an integer of 2 to 30; and $R^6$ is:

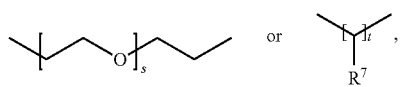

where:

s is an integer of 1 to 10;

t is an integer of 2 to 30; and $R^5$, $R^7$, and $R^8$ are independently hydrogen or methyl.

An additional representative polyorthoester of Formula I, II, III or IV, is one in which $R^3$ and $R^6$ are both —($CH_2$—$CH_2$—O$)_2$—($CH_2$—$CH_2$)—; $R^5$ is methyl; and where p and q are each independently selected from 1, 2, 3, 4, 5, 6, 7, 8, 9, 10, 11, 12, 13, 14, 15, 16, 17, 18, 19, and 20.

In another embodiment of a polyorthoester of Formula I, II, III or IV, $R^3$ and $R^6$ are both —($CH_2$—$CH_2$—O$)_9$—($CH_2$—$CH_2$)—; $R^5$ is methyl; and p or the sum of p and q is on average 2.

In another variation, the polyorthoester is of Formula I, II, III or IV, R is —($CH_2$)$_b$—O—($CH_2$)$_c$—; where b and c are both 2; $R^*$ is a $C_2$ alkyl.

Additional representative polyorthoesters of Formula I, II, III or IV, are those in which $R^5$ is hydrogen or methyl; $R^6$ is

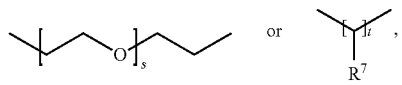

where s is an integer from 1 to 10, or in some embodiments s is selected from 1, 2, 3, or 4; t is an integer from 2 to 30, particularly selected from 2, 3, 4, 5, 6, 7, 8, 9 and 10; $R^7$ is hydrogen or methyl; and $R^3$ is

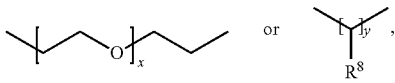

where x is an integer from 1 to 10, or in some embodiments is selected from 1, 2, 3, or 4; y is an integer from 2 to 30, particularly selected from 2, 3, 4, 5, 6, 7, 8, 9 and 10; $R^8$ is hydrogen or methyl; $R^4$ is selected from a residue of an aliphatic diol having from 2-20 carbon atoms (e.g., selected from 2, 3, 4, 5, 6, 7, 8, 9, 10, 11, 12, 13, 14, 15, 16, 17, 18, 19, and 20 carbon atoms), and in some embodiments $R^4$ has from 2 to 10 carbon atoms, interrupted by one or two amide, imide, urea, or urethane groups. In some cases, the proportion of subunits in the polyorthoester in which A is $R^1$ is from about 0.01-50 mole percent. In certain instances, the proportion of subunits in the polyorthoester in which A is $R^1$ is from about 0 to about 30 mole percent, or from about 0.1 to 25 mole percent. Illustrative mole percentages include 10, 15, 20 and 25 mole percent of subunits in the polyorthoester in which A is $R^1$. In one embodiment, the mole percent is 20. Additionally, in one or more embodiments, the proportion of subunits in which A is $R^2$ is less than about 20 percent, less than about 10 percent, or less than about 5 percent, and the proportion of subunits in which A is $R^4$ is less than 20 percent, less than about 10 percent or less than 5 percent.

The polyorthoester, as shown in Formula I, Formula II, Formula III and Formula IV, in certain embodiments, is one of alternating residues of a diketene acetal and a diol, with each adjacent pair of diketene acetal residues being separated by the residue of one polyol, such as a diol.

Methods of manufacturing the polyorthoesters are well known in the art, and are described, e.g., in U.S. Pat. Nos. 6,613,355 and 8,252,304.

Optional Solvents and Excipients

The composition may additionally comprise one or more pharmaceutically acceptable excipients, and some examples are now set forth.

In the embodiment wherein the delivery vehicle is a polymeric formulation, and in particular where the polymer is a polyorthoester, the delivery vehicle may optionally comprise an organic acid, such as that described in co-owned U.S. Patent Application No. 61/982,300, filed Apr. 21, 2014, incorporated herein by reference in its entirety. The organic acid facilitates release of the active agent, such as an amide-type local anesthetic, from the vehicle or composition, in particular, during the early stages of delivery (e.g., days 1-3 post-administration). Generally, the organic acid is a carboxylic acid. Most suitable are organic acids having a molecular weight less than about 300 daltons. Representative organic acids include, e.g., fumaric or maleic acid, ethanoic acid, propanoic acid, butanoic acid, pentanoic acid, hexanoic acid, heptanoic acid, benzoic acid, salicylic acid and acetyl salicylic acid, oxalic acid, malonic acid, succinic acid, glutaric acid, adipic acid, pimelic acid, and so forth. The delivery vehicle may comprise from about 0-80 mole percent of a mono-carboxylic acid, or from about 0-40 mole percent of a di-carboxylic acid, or from about 0 to 25 a tri-carboxylic acid based upon the concentration of basic active agent, for example, bupivacaine base. The amount of the organic acid comprised in the vehicle will depend, at least in part, upon the identity of the particular active agent, the amount of active agent contained in the vehicle, the particular polyorthoester, amount thereof, and desired delivery profile.

As discovered by the Applicants, for a given organic acid, vehicles comprising a greater amount of the organic acid exhibit a faster release rate which is typically most pronounced during the first 1-3 days following administration.

In another embodiment, the delivery vehicle in the form of a semi-solid polyorthoester polymeric formulation may also contain one or more liquid excipients. The excipient can be a pharmaceutically-acceptable polyorthoester compatible liquid excipient. Such excipients are liquid at room temperature and are readily miscible with polyorthoesters. Exemplary polyorthoester compatible liquid excipients include both protic and aprotic solvents. Protic liquid excipients include polyethylene glycol having a molecular weight between about 200 Da and 4,000 Da, or a polyethylene glycol derivative or co-polymer having a molecular weight between about 200 Da and 4,000 Da, e.g., an end-capped PEG such as monomethoxypolyethylene glycol, or a mono-, di- or triglyceride of a C2-C19 aliphatic carboxylic acid or a mixture of such acids, and alkoxylated tetrahydrofurfuryl alcohols. Additional suitable liquid excipients include C1-C4 alkyl ethers of alkoxylated tetrahydrofurfuryl alcohols, and C2-C19 aliphatic carboxylic acid esters, or the like. A particular excipient for semi-solid vehicles is monomethoxy-PEG, having a molecular weight selected from 400, 450, 500, 550, 600 and 650 Da.

Additional liquid excipients include aprotic solvents. Aprotic solvents suitable for use, as well as exemplary polyorthoester vehicles comprising an aprotic solvent are described in U.S. Patent Application Publication No. 2014/0275046, which is incorporated herein by reference in its entirety. Examples of hydrophilic biocompatible, aprotic organic solvents include, for example, amides such as N-methyl-2-pyrrolidone (NMP), 2-pyrrolidone, N-ethyl-2-pyrrolidone, N-cycylohexyl-2-pyrrolidone, dimethyl acetamide, and dimethyl formamide; esters of monobasic acids such as methyl lactate, ethyl lactate, and methyl acetate; sulfoxides such as dimethyl sulfoxide and decylmethylsulfoxide; lactones such as e-caprolactone and butyrolactone; ketones such as acetone and methyl ethyl ketone; and ethers such as dimethyl isosorbide and tetrahydrofuran.

An exemplary semi-solid composition comprises a polyorthoester, a liquid excipient such as NMP or DMSO, at least one active agent such as an amide-type local anesthetic such as bupivacaine or ropivacaine, and an enolic-acid NSAID such as meloxicam and optionally an organic acid additive such as maleic acid. The relative concentrations of the components of the semi-solid composition will vary depending upon the amount of the amide-type local anesthetic(s), enolic-acid NSAID, polyorthoester, polyorthoester-compatible liquid excipient, and organic acid additive, if present. The weight percent of the polyorthoester compatible liquid excipient can range from about 10-50 weight percent, or from about 10-40 weight percent, or from 10-30 weight percent, or from 10-25 weight percent. Exemplary amounts of the polyorthoester-compatible liquid excipient are about 10, 12, 15, 20, 25, 30, 35, 40, 45 or 50 weight percent.

In another embodiment, the compositions described herein and in particular the semi-solid composition comprising a polyorthoester, a liquid excipient such as NMP or DMSO, at least one active agent such as an amide-type local anesthetic such as bupivacaine or ropivacaine, and an enolic-acid NSAID such as meloxicam and optionally an organic acid additive, additionally comprises a viscosity reducing triglyceride solvent, such as those set forth in section 2 below and in the amounts set forth in section 2 below.

The delivery vehicle in the form of a semi-solid polymeric formulation can be prepared by mixing or blending the active agents, the polymer, such as the polyorthoester, an optional polymeric/polyorthoester-compatible liquid excipient, and any other additional additives or excipients as desired. The mixing or blending can be performed by any suitable method, generally at a temperature less than about 50° C., e.g., at room temperature, although in certain instances, depending upon the nature of the materials, mixing or blending may be carried out at higher temperatures, e.g., from about 25 to 100° C. The mixing or blending is generally carried out in the absence of additional solvents, to obtain a homogeneous, flowable and non-tacky vehicle at room temperature.

The polymeric-compatible liquid excipient is typically added to the compositions in an amount ranging from about 10 percent to about 70 percent by weight, relative to the total weight of the composition. The liquid excipient may be present in the composition in an amount ranging from about 20 percent to about 50 percent by weight. In other embodiments, the liquid excipient is present in the composition in an amount ranging from about 10-60 wt %, 15-60 wt %, 15-50 wt %, 20-60 wt %, 25-50 wt %, 30-70 wt %, 30-60 wt %, 30-50 wt %, 35-70 wt %, 35-60 wt % or 35-50 wt %.

The rate of release of the active agent (e.g., drug) can be controlled by adjusting the composition and amount of the polymer and/or by the selection and quantity of the optional additives/excipients. The chemical structure of the polymer (i.e., the type of monomer used or the ratio of monomers for copolymers or terpolymers, the end groups on the polymer chains, and the molecular weight of the polymer) will determine the hydrophilicity or lipophilicity of the polymer material as well as contribute to the degradation time of the polymer depot. More hydrophilic polymers (e.g., polyorthoesters wherein the diol monomer is hydrophilic, e.g., triethylene glycol, tetraethylene glycol, or polyethylene glycol and the like) are used in applications where faster release rates and shorter durations of release are needed. The composition includes the delivery vehicle and the active agents in an amount effective to provide the desired therapeutic effect over the release period.

While the singular form is used to describe the polyorthoester and other composition components in this application, it is understood that more than one polyorthoester and/or more than one amide-type local anesthetic or enolic-acid NSAID selected from the groups described above may be used in the delivery system. In some embodiments of the herein described methods and compositions, the compositions further comprise one or more additional excipients. In one embodiment, a particular excipient is one that does not influence the release of the active agents from the composition.

It is also understood that while not required, other pharmaceutically acceptable inert agents such as coloring agents and preservatives may also be incorporated into the composition.

Aqueous Compositions Comprising a Caine and Enolic-Acid NSAID

As described herein, it was discovered that administering a combination of an amide-type local anesthetic and an enolic-acid non-steroidal anti-inflammatory drug provides a surprisingly effective level and duration of pain relief in a subject. Based upon the disclosures and guidance provided herein, a person having ordinary skill in the art would understand that the combination of an amide-type local anesthetic and an enolic-acid non-steroidal anti-inflammatory drug would also be more effective than an equal amount of the an amide-type local anesthetic or the non-steroidal anti-inflammatory drug administered alone. Accordingly, also disclosed, are aqueous solutions comprising an amide-type local anesthetic and an enolic-acid non-steroidal anti-inflammatory drug. In a particular embodiment, the enolic-acid NSAID in the aqueous composition is meloxicam. In a more particular embodiment, the aqueous composition comprises meloxicam and bupivacaine.

Amide-type local anesthetics which are suitable for the aqueous combination are commercially available, for example, as injectable solutions and include but are not limited to lidocaine, mepivacaine, bupivacaine, and etidocaine. Pharmaceutically acceptable solutions of meloxicam are disclosed, for example, in U.S. Pat. No. 8,920,820. Accordingly, a pharmaceutically acceptable solution of, for example, meloxicam, can be mixed with a solution of the amide-type local anesthetic prior to administration to a subject. For example, the mixing can be done less than an hour prior to administration or within 2 hours, 4 hours, 6 hours, 8 hours, 10 hours, 12 hours, 14 hours, 16 hours, 18 hours, 20 hours, 22 hours or 24 hours prior to administration. The mixture of the amide-type local anesthetic with the enolic-acid NSAID provides a pain relief which is more effective than the same amount of either the amide-type local anesthetic or the enolic-acid NSAID alone. Greater efficacy in providing pain relief of such a combination formulation can be measured, for example, using the Von Frey assay (such as that described in Example 8 below), wherein pain tolerance of a subject will be greater when administered a combination of meloxicam and the amide-type local anesthetic than when administered either active agent alone.

Accordingly, in one embodiment, an aqueous pharmaceutical composition comprising a therapeutically effective amount of meloxicam and a therapeutically effective amount of an amide-type local anesthetic is contemplated. In one embodiment, administration of the composition to a subject provides pain relief to the subject for a period of about 4 days to about 6 days after administration.

In another embodiment, an aqueous solution comprising a therapeutically effective amount of meloxicam is provided, wherein the solution is suitable for adding to a pharmaceutical solution comprising a therapeutically effective amount of an amide-type local anesthetic to generate a mixed solution which is suitable for administering to a subject in need thereof. In one embodiment, administration of the mixed solution to the subject provides pain relief to the subject for a period of about 4 hours to about 12 hours after the administration, alternatively for a period of about 4-24 hours, or 2-4 hours, or 2-6 hours, or 3-5 hours.

In one embodiment, the mixed solution is for use in a method for treating a subject in pain, wherein the method comprises mixing a pharmaceutical solution of meloxicam with a pharmaceutical solution of an amide-type local anesthetic to prepare a mixed solution, and administering the mixed solution to the subject within 24 hours of preparing the mixed solution. The method may also comprise prophylactically treating a subject for pain.

Compositions were prepared and tested in support of the present compositions and methods of use, now described with reference to Examples 1-8. Each of the illustrative compositions described in Examples 1-8 comprises a polyorthoester (POE) of Formula I comprised of 80% triethylene glycol (TEG) and 20% TEG-glycolide (comprising on average 2 glycolides per subunit, i.e., TEG-diglycolide). See, e.g., U.S. Pat. No. 8,252,305, Example 1(d). Compositions containing between 45% to 80% polyorthoester of Formula I, between 20% and 45% of an aprotic solvent, 5% ropivacaine, and 3.6% meloxicam were prepared as described in Example 1. The composition identified in Example 1 as 8026-01-01 was comprised of 61.5 wt % polyorthoester of Formula I, 29.7 wt % of the aprotic solvent NMP, 5.2 wt % ropivacaine base and 3.6% meloxicam. Release rates of ropivacaine and meloxicam were measured in vitro, according to the in vitro test described in Example 2, where a known amount of the composition was placed in a known amount of phosphate buffered saline in a vial. The vial containing the saline and polymeric composition was incubated at 37° C. without agitation, and aliquots of the saline were removed and fixed time intervals. The concentration of each drug was measured in the aliquots. The cumulative drug release from the polymeric depot composition is shown in Table 2-1 of Example 2 and shows that 100% release of both drugs was attained by 72 hours (3 days).

Accordingly, in one embodiment, a composition comprised of a polyorthoester, an amide-type anesthetic and an enolic-acid NSAID is contemplated, where the anesthetic and NSAID are released in vitro from the composition over a period of between about 1-3 days, or over a period of at least about 2 days, or over a period of at least about 3 days.

In another study, described in Example 3, compositions containing between approximately 62-63% polyorthoester of Formula I, between approximately 15-20% of an aprotic solvent, between 10% and 15% bupivacaine base, and 6% to 7.5% diclofenac were prepared.

In another study, described in Example 4, compositions containing between approximately 55% to 80% polyorthoester of Formula I, between approximately 15% and 35% of an aprotic solvent, between about 5-15 wt % bupivacaine, and between about 0.05-3.5 wt % meloxicam were prepared and the in vitro release rates of bupivacaine and meloxicam was measured. The test for measuring in vitro release rates is described in Example 5, and Tables 5-1 and -5-2 in the example summarize the cumulative percent release of each drug from the compositions. The compositions comprising between 55-65 wt % POE and 16-32 wt % of an aprotic solvent provided an extended period of release of bupivacaine with between 37-75 percent of the drug released after 168 hours in vitro. Compositions comprising 70-80 wt % POE, 15 wt % of an aprotic solvent, and 0.5-1.2 wt % of an organic acid (maleic acid) provided a faster rate of drug release, with substantially all drug (e.g., over about 80%, 85% or 90% of the bupivacaine load) released in about 120 hours. This study shows how the addition of optional excipients, such as the organic acid, can tailor the period of drug release in the compositions.

Figure 1B:
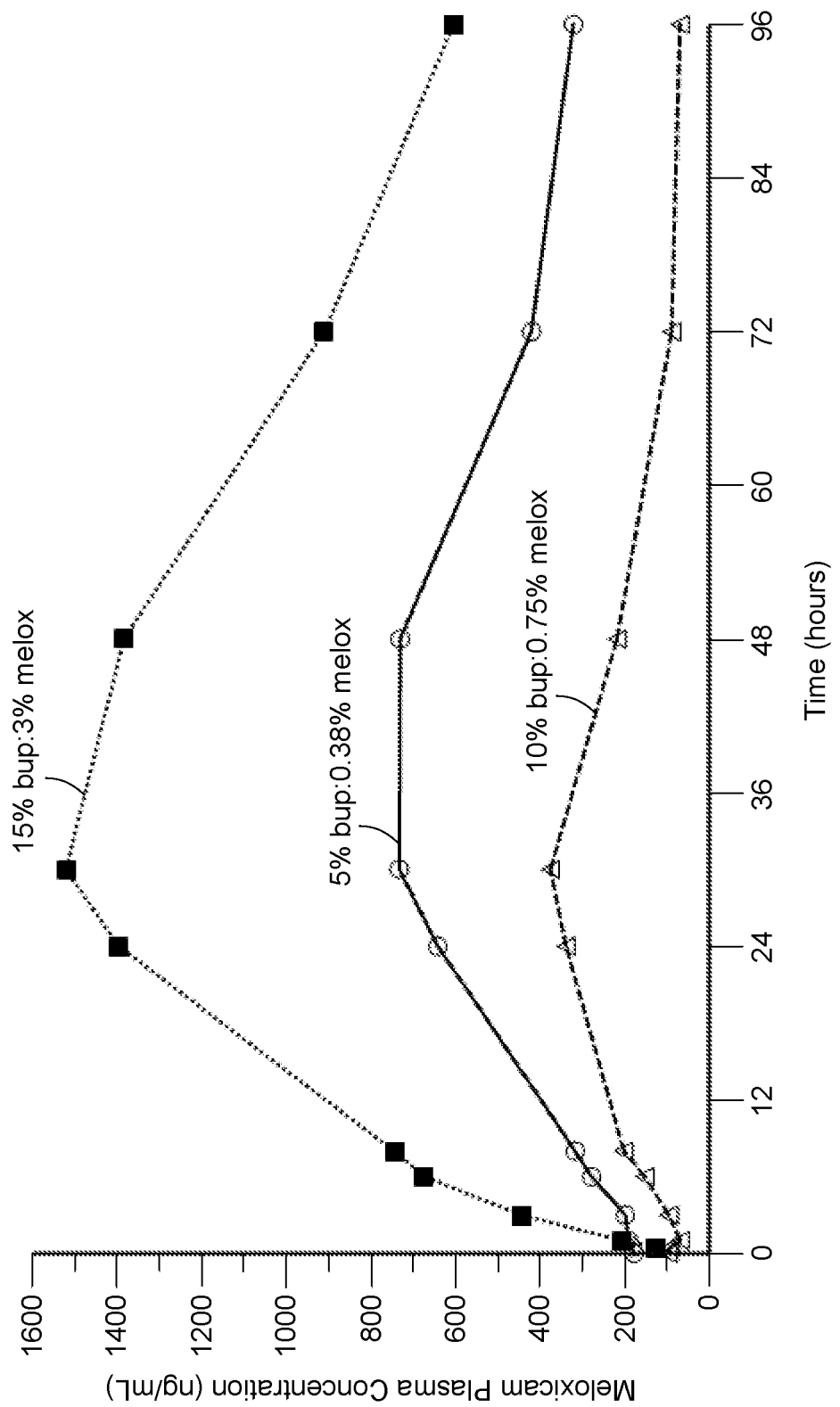

Several of the compositions prepared in Example 4 were tested in vivo to measure the pharmacokinetics of bupivacaine and meloxicam. The compositions identified in Table 4-1 (Example 4) as 8026-04-03, 8026-04-04 and 8026-04-05 were injected with 4 mL of a composition, and plasma concentration of the drugs was determined from blood samples taken for up to 7 days after administration (see Example 6). The data from the study is shown in FIGS. 1A-1B, where plasma levels of bupivacaine (FIG. 1A) and of meloxicam (FIG. 1B) are plotted at each time point, for the three compositions—15 wt % bupivacaine/3 wt % meloxicam (closed squares; composition no. 8026-04-03); 10 wt % bupivacaine/0.75 wt % meloxicam (open circles; composition no. 8026-04-04); and 5 wt % bupivacaine/0.38 wt % meloxicam (open triangles; composition no. 8026-04-05). The data indicates that the compositions provide measurable plasma concentrations of bupivacaine and meloxicam over a period of at least about 4 days (96 hours) or at least about 3 days, following administration.

Another in vivo pharmacokinetic study was conducted in dogs, as described in Example 7. The composition comprised of 79% polyorthoester, 0.6 wt % maleic acid, 15 wt % NMP, 5% bupivacaine and 0.15 wt % meloxicam (composition identification no. 8026-04-07, Example 4) was administered in two separate injections of approximately 0.5 mL each. Plasma samples were collected from each dog and were analyzed for bupivacaine and meloxicam. The data from the study is shown in FIGS. 2A and 2B.

Figure 2A:
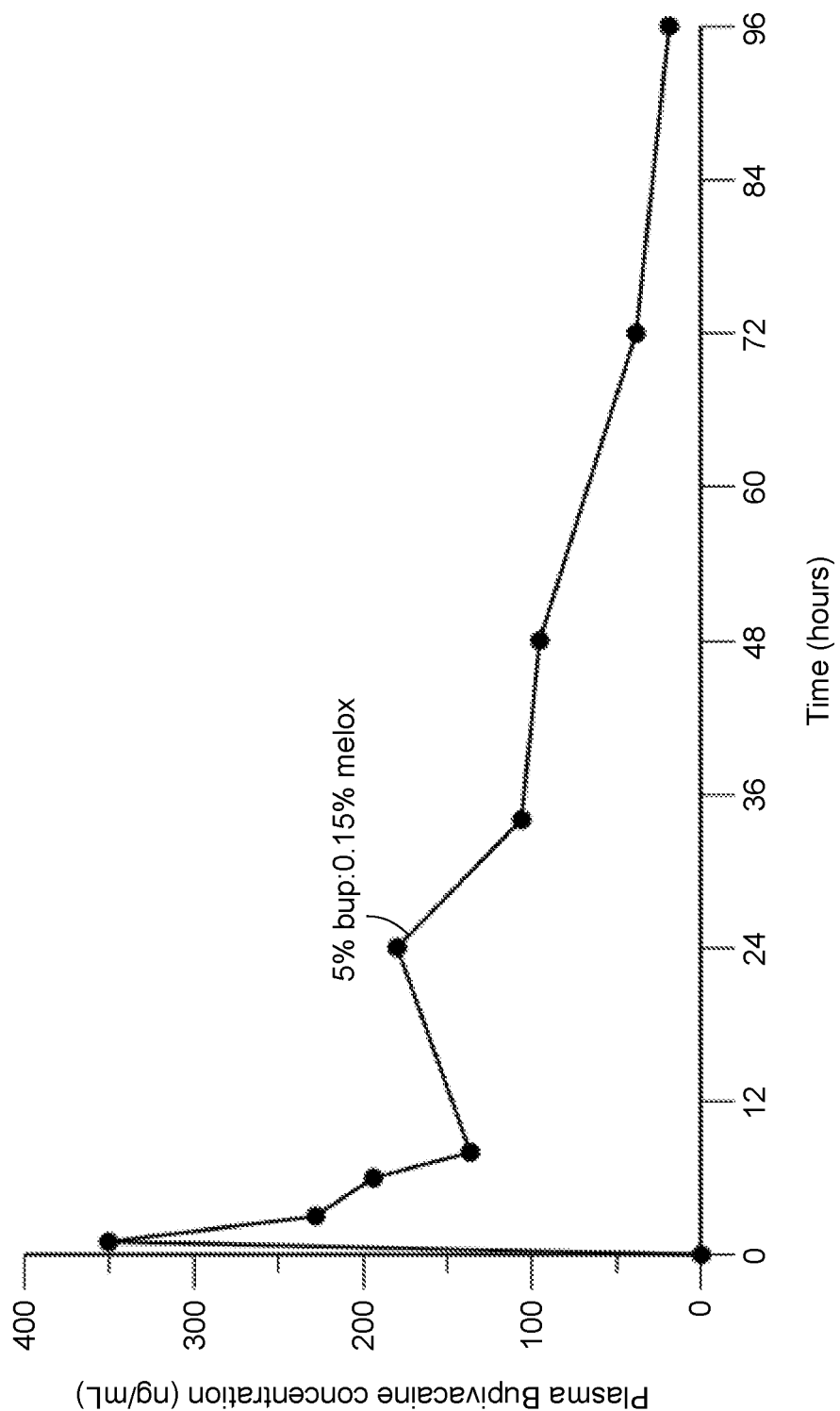
FIGS. 2A-2B are graphs of plasma concentration of bupivacaine (FIG. 2A) and of meloxicam (FIG. 2B), in ng/mL, as a function of time, in hours, after administration in vivo to a dog of a composition (no. 8026-04-07) comprised of a polyorthoester delivery vehicle and 5 wt % bupivacaine and 0.15 wt % meloxicam.
Figure 2B:
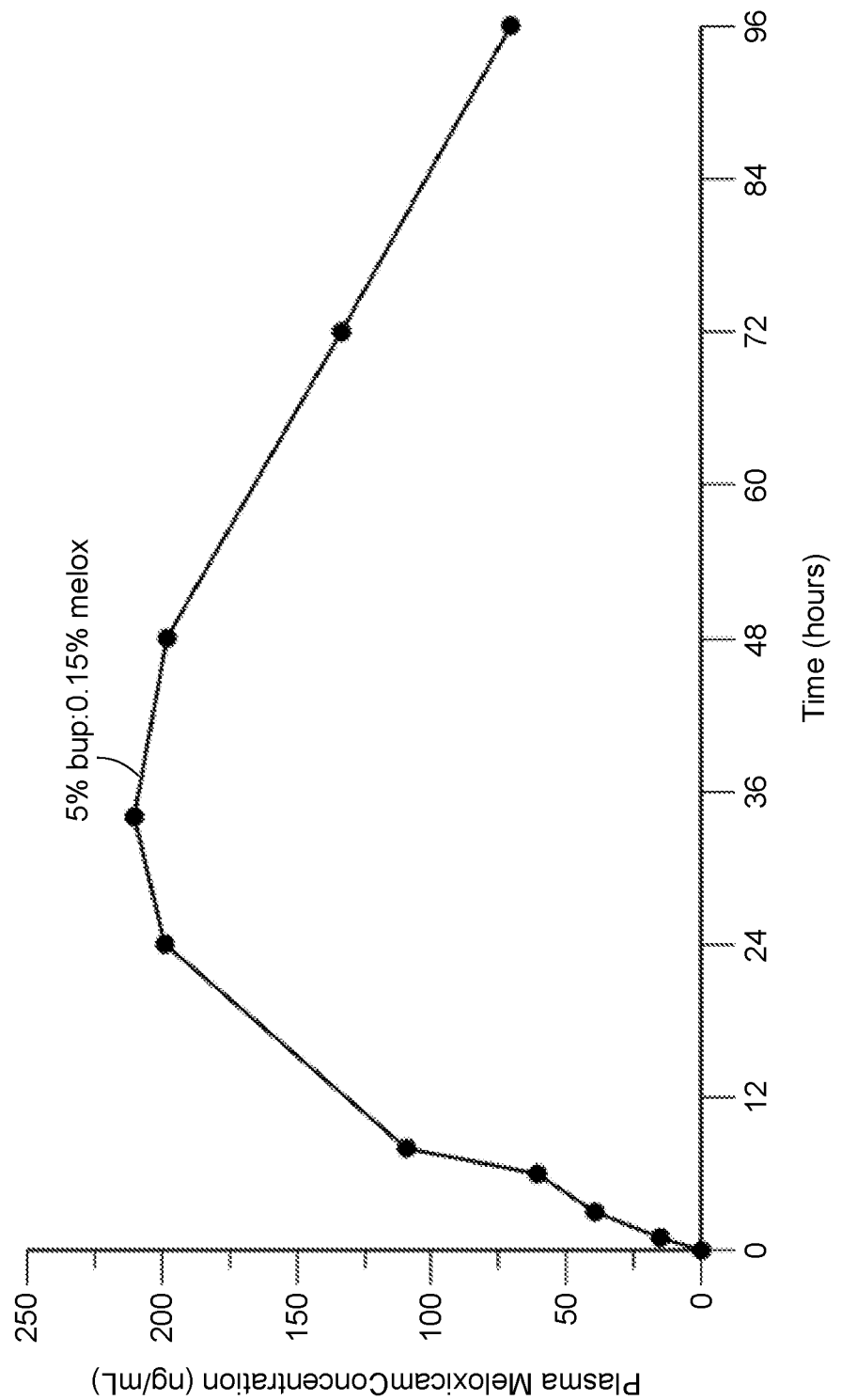

FIGS. 2A-2B are graphs of plasma concentration of bupivacaine (FIG. 2A) and of meloxicam (FIG. 2B), in ng/mL, as a function of time, in hours, after administration in vivo to a dog of a composition (no. 8026-04-07) comprised of a polyorthoester delivery vehicle and 5 wt % bupivacaine and 0.15 wt % meloxicam The composition provides measurable plasma concentrations of bupivacaine and meloxicam over a period of at least 4 days (96 hours) or at least about 3 days, following administration.

Example 8 describes several studies conducted to evaluate the pharmacodynamics of the bupivacaine-meloxicam compositions. Using a post-operative (POP) pain porcine model system, where a 7 cm long skin and fascia incision was made in the left flank under general anesthesia to pigs, the test composition or control article was applied to the wound. The skin incision was then closed using sterile sutures. Postoperative pain was assessed using the Von Frey methodology, as described in Example 8. In a first study (Example 8A), extended release polymer composition containing 15% bupivacaine was compared to an extended release polymer composition containing 5% ropivacaine. The method of administration to the surgical site was varied to evaluate whether this resulted in any difference in pharmacodynamics. The methods tested were to either instill the composition directly onto the surface of the wound area or inject the composition subcutaneously into the lateral margins of the wound. Table 8-1 details the test groups and method of administration.

Figure 3:
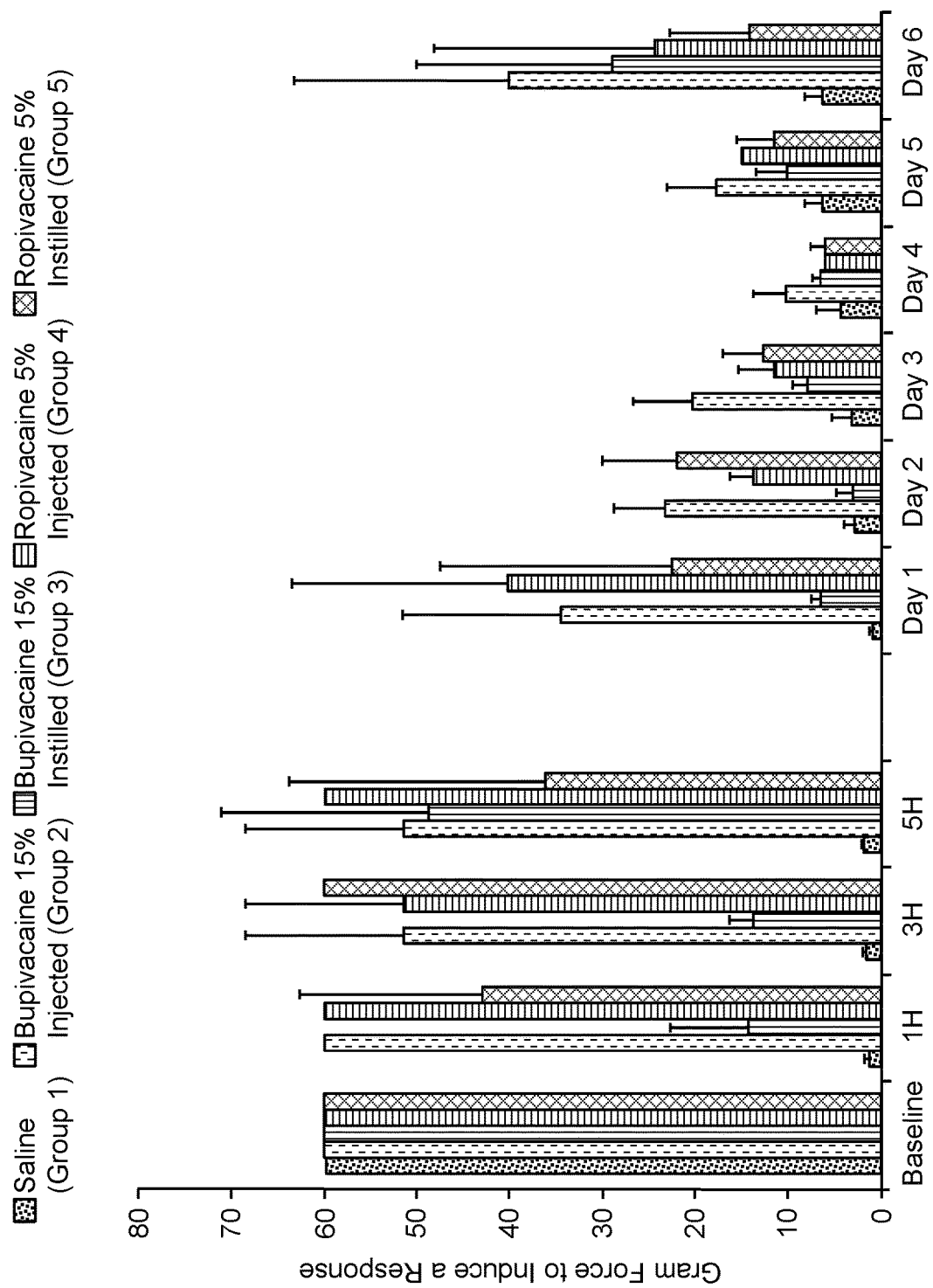
FIG. 3 is a bar graph of withdrawal force, in gram force, as a function of time, in hours and days, after administration in vivo to pigs of compositions comprised of a polyorthoester delivery vehicle and either (i) 15 wt % bupivacaine administered by injection (vertical dashes fill) or by instillation (vertical line fill) or (ii) 5 wt % ropivacaine administered by injection (horizontal line fill) or instillation (diamond crosshatch fill), and bars with dotted fill represent the response for the control group treated with saline.

The pharmacodynamic response, measured by the von Frey test, is shown in FIG. 3. Withdrawal force, in gram force, is shown as a function of time, in hours and days, after administration in vivo for each of the following compositions: compositions comprised of a polyorthoester delivery vehicle and either (i) 15 wt % bupivacaine administered by injection (vertical dashes fill; Group 2) or by instillation (vertical line fill; Group 3) or (ii) 5 wt % ropivacaine administered by injection (horizontal line fill; Group 4) or instillation (diamond crosshatch fill; Group 5); bars with dotted fill represent the response for the control group treated with saline (Group 1). Subcutaneous injection of compositions comprising ropivacaine or bupivacaine both offered a sustained effect following a single administration prior to wound closure. Application of the composition onto the wound surface was less effective than injection for the 15% bupivacaine composition; however a corresponding difference between modes of administration was not observed with the 5% ropivacaine composition. Comparing Groups 2 and 4, there was a significant increase in force required to provoke withdrawal on Days 0 and 2 through 5 in the pigs administered either composition by wound injection compared to the vehicle controls. There was little difference in response between bupivacaine and ropivacaine compositions and an increase in sensitivity (lower force to provoke a withdrawal) was observed in all drug treatment groups on Days 2-4 with some increase in the force required to provoke a withdrawal in pigs that received drug treatment (Groups 2-5) on Day 6. It was hypothesized that inflammation-mediated failure of the local anesthetic was the reason for the diminished effectiveness on Days 2-4 and recovery on Day 6 as inflammation subsided.

Another pharmacodynamics study was conducted (Example 8B) to compare the efficacy of extended release formulations containing a local anesthetic to formulations containing a local anesthetic in combination with an NSAID. The nociceptive activity of five different formulations summarized in Table 8-2 of Example 8B was evaluated in the pig POP model. Extended release formulations containing ropivacaine (slower release and faster release, Groups 2 and 3 respectively) were compared to extended release formulations containing bupivacaine and the NSAIDs diclofenac and meloxicam, Groups 4 and 5 respectively. A dose volume of 2 mL for vehicle or test article was injected subcutaneously into the lateral margins of the incision and the incision closed with sutures. Assessment of nociception by von Frey method at baseline, 1, 3, and 5 hours, and days 1 through 6 after surgery.

Figure 4:
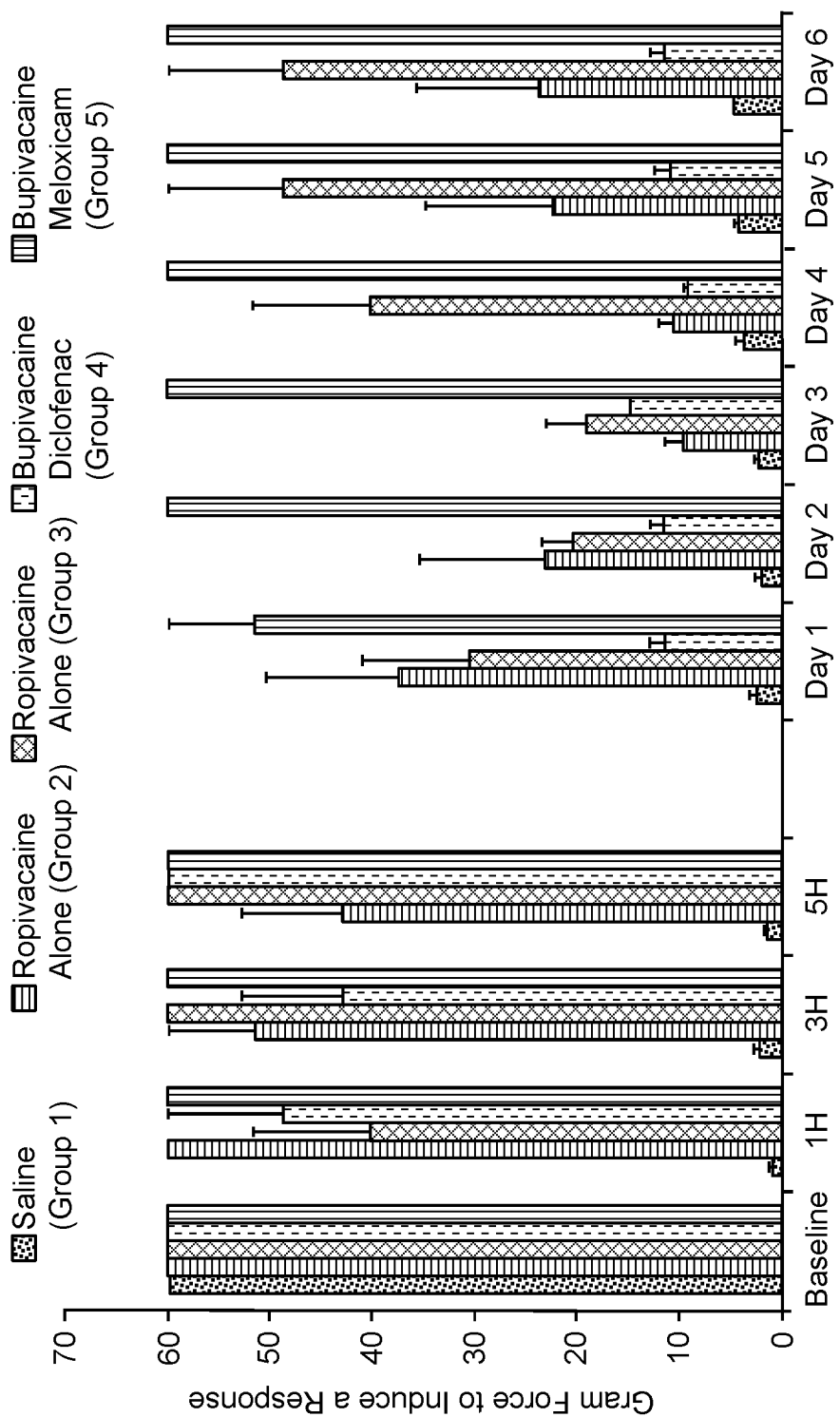
FIG. 4 is a bar graph of withdrawal force, in gram force, as a function of time, in hours and days, after administration by subcutaneous injection to a wound incision in vivo in pigs of compositions comprised of a polyorthoester delivery vehicle and (i) 5 wt % ropivacaine with 0.6% maleic acid (horizontal line fill), (ii) 5 wt % ropivacaine with 0.2% maleic acid (diamond crosshatch fill), (iii) 15 wt % bupivacaine and 7.5 wt % diclofenac (vertical dashes fill), or (iv) 15 wt % bupivacaine and 3.5 wt % meloxicam (vertical line fill); bars with dotted fill represent the response for the control group treated with saline.

The results are shown in FIG. 4, where withdrawal force, in gram force, is shown as a function of time, in hours and days, after administration. The compositions are denoted in FIG. 4 as follows: compositions comprised of a polyorthoester delivery vehicle and (i) 5 wt % ropivacaine with 0.6% maleic acid (horizontal line fill; Group 2), (ii) 5 wt % ropivacaine with 0.2% maleic acid (diamond crosshatch fill; Group 3), (iii) 15 wt % bupivacaine and 7.5 wt % diclofenac (vertical dashes fill; Group 4), or (iv) 15 wt % bupivacaine and 3.5 wt % meloxicam (vertical line fill; Group 5); and bars with dotted fill represent the response for the control group treated with saline (Group 1).

The results indicate that, with the exception of the control, all of the compositions evaluated in the model were effective in the short-term for treatment/management of pain, e.g., in the first 5 hours post-incision. The extended release polymer composition containing ropivacaine as the only active agent (Group 3) was as effective in the first 5 hours after administration as the extended release polymer composition comprising bupivacaine in combination with meloxicam and bupivacaine combined with diclofenac. At the 5 hour time point, the composition comprising ropivacaine alone tested in Group 1, but with a higher amount of maleic acid than the composition tested in Group 2, was less effective in its relief of pain, as can be seen in the reduced withdrawal force recorded in comparison with the other three compositions. This is likely due to the higher content of maleic acid in the composition, thereby leading to a faster release rate of the active agent (see, e.g., U.S. Patent Application No. 61/982, 300, filed Apr. 21, 2014). A notable difference in the compositions is observed at the longer time points, e.g., over days 1-6. Over days 1-3, compositions containing ropivacaine alone (in reference to the active agent), as well as the bupivacaine/diclofenac composition, exhibited diminishing analgesia, as shown by a trend in reduced withdrawal force. In contrast, the composition comprising the combination of bupivacaine and meloxicam was significantly more effective than the other three compositions. The analgesia achieved by the composition comprising the combination of bupivacaine and meloxicam remained essentially unchanged over the course of the entire study and the measured withdrawal force exhibited for this composition was, with the exception of day 1, the maximum measured force. While late in the study, the compositions containing ropivacaine alone (Groups 2 and 3) appeared to regain their analgesic effect, as demonstrated by the increased withdrawal force observed over days 4-6, neither was as effective or as consistent in its pain reduction as the bupivacaine/meloxicam composition, which maintained its analgesic activity over days 1-6. In contrast to the bupivacaine/meloxicam composition, the bupivacaine composition containing a different NSAID, diclofenac, continued to diminish in its ability to provide pain relief over time, as illustrated by a trend in decreasing withdrawal force from about 5 hours to about 6 days.

Thus, the two compositions containing different NSAIDs exhibited different pain relief profiles in the post-operative pain model employed. The data unexpectedly shows that incorporation of an enolic-acid NSAID (such as meloxicam) into the composition allowed the local "caine"-type anesthetic to better function and provide analgesia. The pain response profile for the bupivacaine/meloxicam combination illustrates good short term efficacy, over about the first 1-10 hours or so post-surgery, followed by a small drop in efficacy on day 1, and a subsequent rapid recovery such that by about day 2, the composition is again effective in providing maximal pain relief from day 2 to at least day 6 as evidenced by the plateau in withdrawal force observed. The combination is notably superior over the other compositions tested, and in the present study, provides surprisingly enhanced pain relief, especially in comparison to the bupivacaine/diclofenac composition.

Another pharmcodynamic study was conducted to evaluate five different formulations containing different concentrations of the two active ingredients, bupivacaine and meloxicam. As described in Example 8C, the formulation summarized in Table 8-3 were administered either by 1) subcutaneous injection around the wound margins or 2) by direct application to the wound surface created by the incision or 3) injected into the tissues on either side of the wound. The results showed that all bupivacaine/meloxicam compositions demonstrated good analgesia through day 6 post-administration (data not shown) consistent with the previous study (Example 8B). The data also suggested that a bupivacaine concentration of greater than about 5 wt % in the composition offers no additional analgesia. A dose response for meloxicam was not observed. Thus, in one embodiment, compositions comprising an amide-type local anesthetic is between about 0.01-7.5 wt %, alternatively between about 0.1-6 wt %, alternatively between about 0.5-5 wt %.

Example 8D describes another study conducted to evaluate the in vivo response provided by compositions containing 5 wt % bupivacaine with varying concentrations of meloxicam ranging from 0.08 to 0.3 wt %. Table 8-4 summarizes the compositions and test groups. The compositions were administered to pigs as subcutaneous injections into both sides of the incision, and analgesia was evaluated using the von Frey test.

Figure 5A:
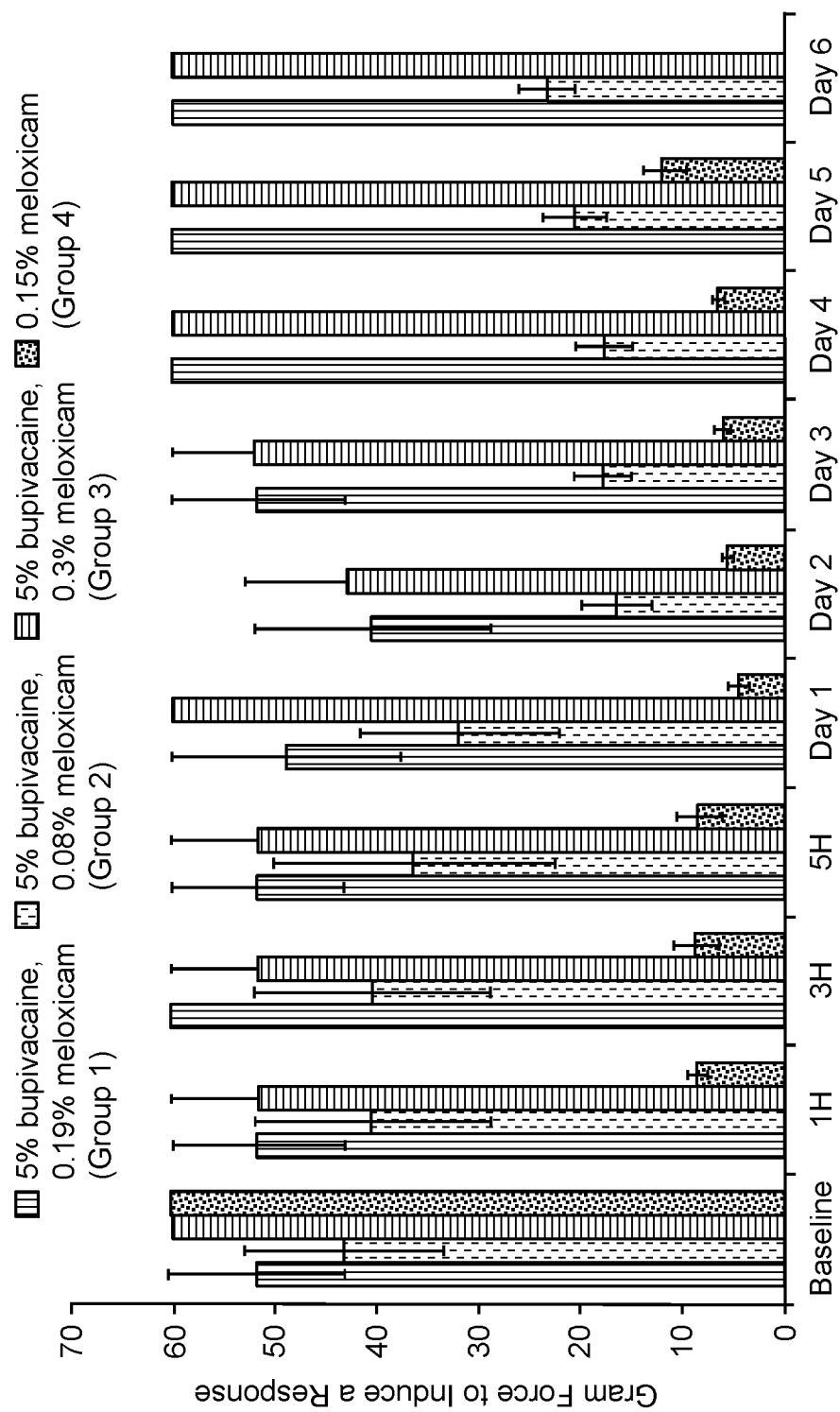
FIGS. 5A-5B are bar graphs of withdrawal force, in gram force, as a function of time, in hours and days, after administration by subcutaneous injection to a wound incision in vivo in pigs of compositions comprised of a polyorthoester delivery vehicle and 5 wt % bupivacaine in combination with meloxicam at 0.08 wt % (vertical dash fill), 0.19 wt % meloxicam (vertical line fill), and 0.3 wt % meloxicam (horizontal line fill), a composition comprised of a polyorthoester delivery vehicle and 0.15 wt % meloxicam alone (dotted fill) (FIG. 5A) and compositions comprised of a polyorthoester delivery vehicle and 5 wt % ropivacaine in combination with 0.38 wt % meloxicam (diamond crosshatch fill) or with 5 wt % ropivacaine alone (no fill; open bars) (FIG. 5B)
Figure 5B:
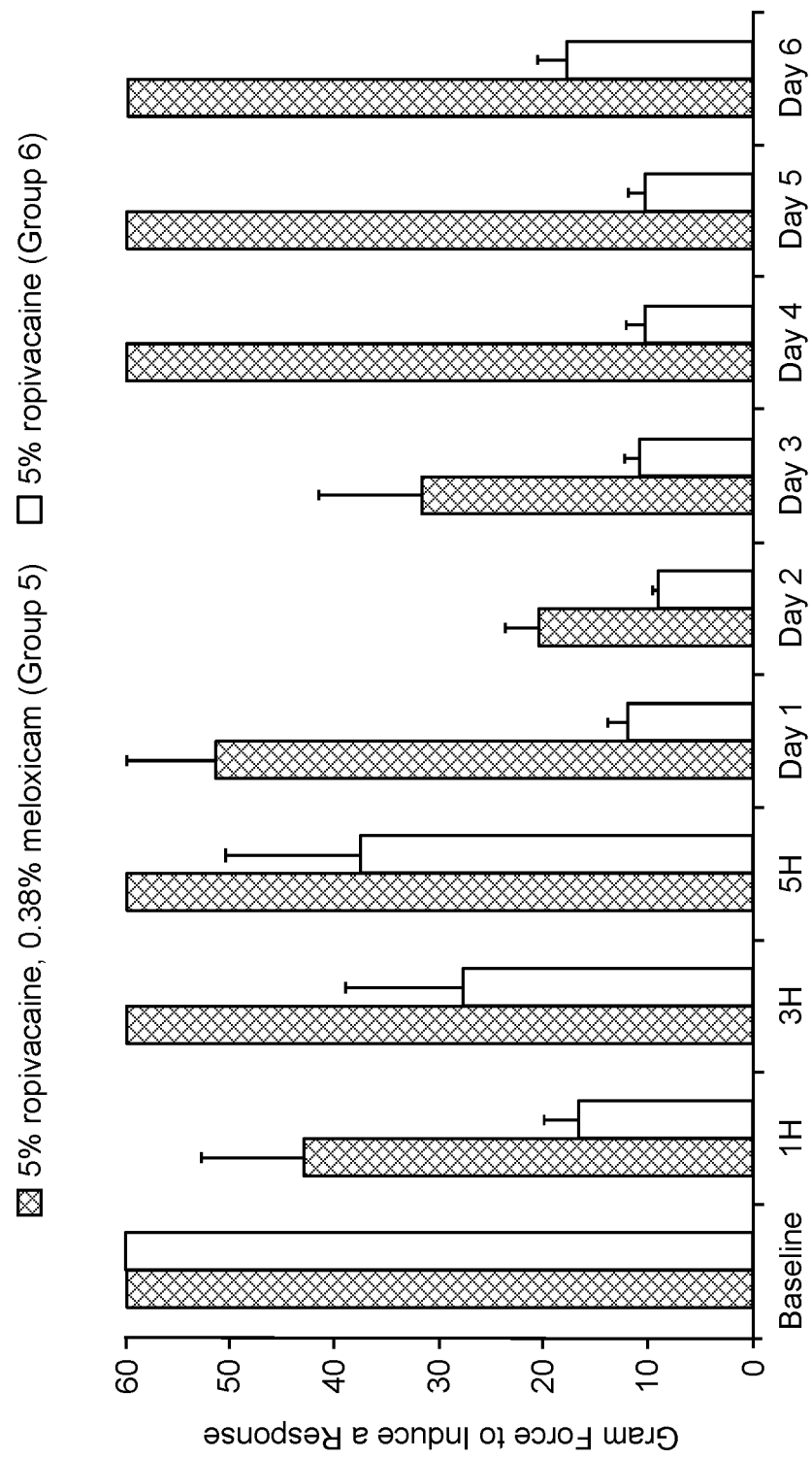

Results are shown in FIGS. 5A-5B, where withdrawal force, in gram force, is shown as a function of time, in hours and days, after administration. The test compositions are denoted in FIGS. 5A-5B as follows: comprised of a polyorthoester delivery vehicle and 5 wt % bupivacaine in combination with meloxicam at 0.08 wt % (vertical dash fill; Group 2), 0.19 wt % meloxicam (vertical line fill; Group 1), and 0.3 wt % meloxicam (horizontal line fill; Group 3), a composition comprised of a polyorthoester delivery vehicle and 0.15 wt % meloxicam alone (dotted fil: Group 4) (FIG. 5A) and compositions comprised of a polyorthoester delivery vehicle and 5 wt % ropivacaine in combination with 0.38 wt % meloxicam (diamond crosshatch fill; Group 5) or with 5 wt % ropivacaine alone (no fill; open bars; Group 6). A variable degrees of anti-nociception were obtained across the 6-day post-surgery observations for Groups 1, 2 and 3 with diminishing analgesia observed in the Group 2 composition containing 0.08% meloxicam. The Group 4 composition of meloxicam alone showed essentially no analgesic effect. The formulations containing ropivacaine with and without meloxicam demonstrated the same trend as seen with bupivacaine formulations (see FIG. 5B). Meloxicam had a positive anti-nociceptive contribution to the effect beyond the effect seen with the local anesthetic alone. The data also suggests that between about 0.01-5 wt % amide-type local anesthetic in combination with at least about 0.1 wt % or 0.15 wt % of an enolic-acid NSAID provides a synergistic effect in analgesia.

Accordingly, as evidenced by the data in FIG. 4 and FIGS. 5A-5B, in one embodiment, the compositions are administered for the management of pain, for the treatment of pain, or for prophylactic treatment of pain, to a person in need. Administration provides, as measured in an in vivo model for post-operative pain, a decrease in pain relief after administering, where the decrease in pain relief is for a period measured from about one (1) hour and about 3-8 hours or about 3-24 hours after administering and is relative to the pain relief measured at times less than one hour after administration (e.g., at baseline with regard to FIG. 4). The period of decreased pain relief is followed by a period of increased or increasing pain relief, where this period is from between about 1-3 days or about 1-4 days or about 1-5 days after administering. The increased or increasing pain relief during the period of increased pain relief is with respect to the pain relief measured during the period of decreased pain relief. In one embodiment, the pain relief during the period of decreased pain relief and/or during the period of increased pain relief is an average of the values measured in the in vivo model for post-operative pain during the relevant period. In another embodiment, the pain relief during the period of increased pain relief is considered an increased pain relief if the pain relief measured in the in vivo model for post-operative pain is greater on day 2 than on day 1 (24 hours) after administration. In another embodiment, the pain relief during the period of increased pain relief is considered an increased pain relief if the pain relief measured in the in vivo model for post-operative pain is greater on day 3 than on day 1 (24 hours) after administration. In another embodiment, the pain relief during the period of increased pain relief is considered an increased pain relief if the pain relief measured at any time point in the period using an in vivo model for post-operative pain is within about 10% of the pain relief at any time point measured in the in vivo model for post-operative pain at times less than 1 hour after administration (e.g., baseline).

In another embodiment, the composition provides pain relief (as measured in an in vivo model for post-operative pain) over a period of between about 2-5 days following administration that is at least, on average, about 50% of the average pain relief provided by the composition 1-5 hours post-administration. The average pain relief during a time period, e.g., during a time period of 1-5 hours post-administration, in one embodiment, is the average of the pain relief scores or values collected during the time period. In one embodiment, average refers to the arithmetic mean, where the average pain relief is obtained by calculating the sum of the pain relief scores or values during a time period and dividing that sum by the number of summed values or scores.

2. Compositions Comprising a Viscosity Reducing Triglyceride Solvent

With respect to the compositions described herein which comprise a biodegradable polyorthoester polymer as the delivery vehicle, these compositions find use, for example, as drug delivery systems or as medical or surgical devices. For such uses, the composition is typically administered by injection into the body with standard syringes and small gauge needles. Thus, it is desirable to provide a composition with a viscosity that is readily dispensed from syringes and small gauge needles yet has the release kinetics of active agent required for therapy. As is known in the art, for example in U.S. Patent Publication No. US2014/0275145, which is incorporated herein by reference in its entirety, the selection of an aprotic polar solvent or solvents in the system may be used to modulate the release profile of an active agent from the polymeric composition. These compositions comprising a polar aprotic solvent and a polyorthoester have viscosities of less than about 10,000 mPa-s at 37° C., and a drug release profile that depends on the solvent choice and amount. Provided herein are compositions with a viscosity suitable for administration via a needle to a subject in need, with a drug release profile similar to a composition with a higher viscosity. As will be illustrated, these compositions find use in applications that require injection through long narrow gauge needles, as in use as a nerve block, or in forming depots in situ for long-term delivery of active agents, such as granisetron for managing nausea.

As can be appreciated, the viscosity of a composition is temperature dependent. For example, a composition with a viscosity of 10,000 mPa-s measured at 37° C. will have a higher viscosity measured at 25° C.; and for the polyorthoester compositions described herein, the viscosity at 25° C. is often from about 7 to 10 fold higher than the viscosity at 37° C. Because the compositions are generally stored at room temperature and administered at room temperature (20-25° C.) it is desirable to have compositions wherein the viscosity is such that the composition can be readily administered at 25° C. through a needle. This embodiment of the invention provides such a composition.

It was found that a triglyceride solvent can be added to compositions comprising a polyorthoester and a polar aprotic solvent to provide a 10, 20, 30 or 40-fold reduction in composition viscosity when measured at 25° C. with a viscometer (relative to viscosity of a similar composition lacking the triglyceride solvent measured at 25° C. with a viscometer) without significantly altering the drug release kinetic as reflected in the in vitro release profile or in the pharmacokinetic profile of the composition. Such is not the case with polar aprotic solvents, where the amount of solvent in a composition will have a measurable impact on the drug release kinetics. That is, by way of example, an initial composition containing a certain concentration of a polar aprotic solvent will demonstrate specific drug release kinetics. Increasing the concentration of that polar aprotic solvent by adding more of that polar aprotic solvent to the initial composition will typically result in a new composition with altered drug release kinetics relative to the initial composition. Surprisingly, this is not the case when a triglyceride viscosity reducing agent is added to compositions containing polar aprotic solvents. Beneficially, the viscosity of a composition may be reduced by a factor of 10, 12, 15, 20, 30 or 40 by the addition of a triglyceride viscosity reducing agent to a composition comprising a polyorthoester and a polar aprotic solvent with minimal alteration of the drug release profile as compared to a similar composition lacking the triglyceride viscosity reducing agent. The triglyceride viscosity reducing agent is one having three fatty acid groups wherein each fatty acid group independently has between 1-7 carbon atoms, and is referred to in some cases as a 'short chain triglyceride.' In some embodiments, the delivery system has a viscosity of less than about 10,000 mPa-s, 5,000 mPa-s, or 2,500 mPa-s, when measured at 25° C. using a viscometer.

Exemplary triglyceride viscosity reducing agents include but are not limited to triacetin (1,2,3-triacetoxypropane, 1,2,3-triacetylglycerol, glycerol triacetate, or glyceryl triacetate); tripropionin (glyceryl tripropionate or 1,2,3-tripropylglycerol); or tributyrin (1,2,3-tributyrylglycerol, or glycerol tributyrate). These triglyceride viscosity reducing agents have three fatty acid chains, wherein each fatty acid chain independently has between 1-7 carbons, and is thus a relatively 'short chain' fatty acid ester. It is understood that combinations of short chain esters are also acceptable, for example glycerol diacetate monopropionate and the like.

The aprotic solvent is a solvent with a dipole moment of greater than about 2 debye (D) ($6.67 \times 10^{-30}$ coulomb meter), or greater than about 2.2 D ($7.34 \times 10^{-30}$ coulomb meter), or greater than about 2.4 D ($8.05 \times 10^{-30}$ coulomb meter). In one embodiment, the aprotic solvent is a solvent with a dipole moment of greater than about 2 D, or greater than about 2.2 D, or greater than about 2.4 D and is water miscible. In another embodiment, the aprotic solvent is a solvent with a dipole moment of greater than about 2 D, or greater than about 2.2 D, or greater than about 2.4 D and is poorly miscible in water. In one embodiment, a solvent is miscible with water if it forms a homogeneous solution with water in all proportions at room temperature (20-25° C.). A solvent is partially miscible if it forms a homogeneous solution with water in some proportions at room temperature (20-25° C.). A solvent is poorly miscible if it does not form a homogeneous solution with water (20-25° C.). Examples of aprotic solvents suitable for use in the delivery systems are described, for example, in U.S. Pat. Pub. No. 2014/0275046 (incorporated herein by reference in its entirety), however, exemplary aprotic solvents may encompass amides, ethers, ketones, or sulfoxides. Exemplary amides include 2-pyrrolidone, dimethyl formamide, N-methyl-2-pyrrolidone and dimethyl acetamide. Exemplary ethers include dimethyl isosorbide and tetrahydrofuran. Exemplary ketones include acetone and methyl ethyl ketone. Exemplary sulfoxides include dimethyl sulfoxide and decylmethylsulfoxide. Additional polar aprotic solvents suitable for use in these low viscosity delivery systems include lactones such as ester-caprolactone and butyrolactone and esters such as an alcohol, propylene carbonate (4-methyl-1,3-diololan-2-one).

In such a delivery system which comprises a polyorthoester, such as that described herein as Formula I, II, III or IV, a polar aprotic solvent and a triglyceride viscosity reducing agent, the polyorthoester is miscible within the solvent comprising the triglyceride viscosity reducing agent and polar aprotic solvent. Accordingly, the composition can be prepared to form a single phase into which a therapeutically active agent is dispersed or solubilized for efficient delivery.

In a particular embodiment, the delivery system comprises a polyorthoester described herein as Formula I, the short chain triglyceride viscosity reducing agent triacetin, and a polar aprotic solvent which is dimethylsulfoxide (DMSO), N-methyl pyrrolidone (NMP) or dimethyl acetamide (DMAC).

Pharmaceutical delivery systems comprising the polyorthoester, triglyceride viscosity reducing agent and polar aprotic solvent can be used as delivery systems for administration of any therapeutically active agent to provide delivery of the agent over a desired period of time. The therapeutic agent is one which can be dispersed or solubilized in the single phase which is formed by the combination of the polyorthoester, short chain triglyceride viscosity reducing agent and polar aprotic solvent.

Methods for making the delivery systems described above may be achieved by a process as described in Examples 10 and 14. In one embodiment, an active agent is dissolved in an aprotic solvent. The dissolution may be performed at an elevated temperature such as from about 60-80° C. or at about 80° C. Separately, appropriate amounts of polyorthoester polymer and short chain triglyceride viscosity reducing agent are combined and mixed thoroughly. The polyorthoester polymer and short chain triglyceride viscosity reducing agent can be combined and/or mixed at an elevated temperature of between about 60-80° C. or between about 65-75° C. or at about 70° C. The solution containing the active agent is then combined with the appropriate amount of the blend of polymer and short chain triglyceride and mixed until homogeneous. It has been observed that the presence of the triglyceride viscosity reducing agent can reduce the viscosity of the delivery system by about 10 to 40-fold as compared to the delivery system in the absence of the triglyceride viscosity reducing agent. Such delivery systems are referred to herein as "low viscosity delivery systems." The low viscosity delivery systems provide the duration and level of relief (e.g., relief from nausea or relief from pain) similar to that observed after administration of a similar composition formulated without the triglyceride viscosity reducing agent.

Low viscosity delivery systems can be formulated with appropriate amounts of the polyorthoester, solvent comprising a short chain triglyceride viscosity reducing agent and polar aprotic solvent. For example, a low viscosity delivery system may be formulated to contain 40% to 75%, 40% to 60%, 45% to 55%, 65 to 75%, or about 40%, 45%, 50%, 55%, 60%, 65%, 70%, or 75% by weight of the polyorthoester. The polar aprotic solvent in the delivery system may be present in a weight percent ranging from about 3% to 25%, 3% to 10%, 5% to 7.5%, 10% to 25%, 15% to 20%, or about 3%, 5%, 7.5%, 10%, 12%, 15%, 20%, or 25%. The solvent comprising the short chain triglyceride viscosity reducing agent is in the composition at a weight percent of about 5% to 45%, 30% to 45%, 35% to 40%, 5% to 25%, 10% to 20%, or about 5%, 10%, 15%, 20%, 25%, 30%, 35% or 40%.

The low viscosity delivery system can contain more than one active agent. In some embodiments, the one or more active agents must be soluble in the solvent comprising the short chain triglyceride viscosity reducing agent, in the polar aprotic solvent or in a mixture of the two solvents. The active agent(s) is dispersed in or solubilized in the delivery system containing the polyorthoester. The total weight percent of active agent in the low viscosity delivery system can vary, for example, from about 0.1% to 5%, 0.1% to 10%, 0.1% to 5%, 2.5% to 7.5%, 3% to 5%, or at about 0.1%, 0.25%, 0.5%, 1.0%, 2.5%, 5%, 7.5% or 10% by weight.

Studies conducted in support of this aspect of the invention as set forth in Examples 9-13, now to be described. In each of these examples, compositions using a delivery vehicle comprised of a polyorthoester (POE) of Formula I comprising 80% triethylene glycol (TEG) and 20% TEG-glycolide (comprising on average 2 glycolides per subunit, i.e., TEG-diglycolide) was used. See, e.g., U.S. Pat. No. 8,252,305, Example 1(d).

In a first study, described in Example 9, a composition prepared as described in Example 4 (composition identification no. 8026-04-07) was prepared and a similar composition with 30% triacetin (glycerol triacetate) as a model triglyceride viscosity reducing agent was prepared. The viscosity of the composition with the triglyceride viscosity reducing agent was measured using a viscometer at 25° C. and was at 7,115 mPa-s.

Figure 6A:
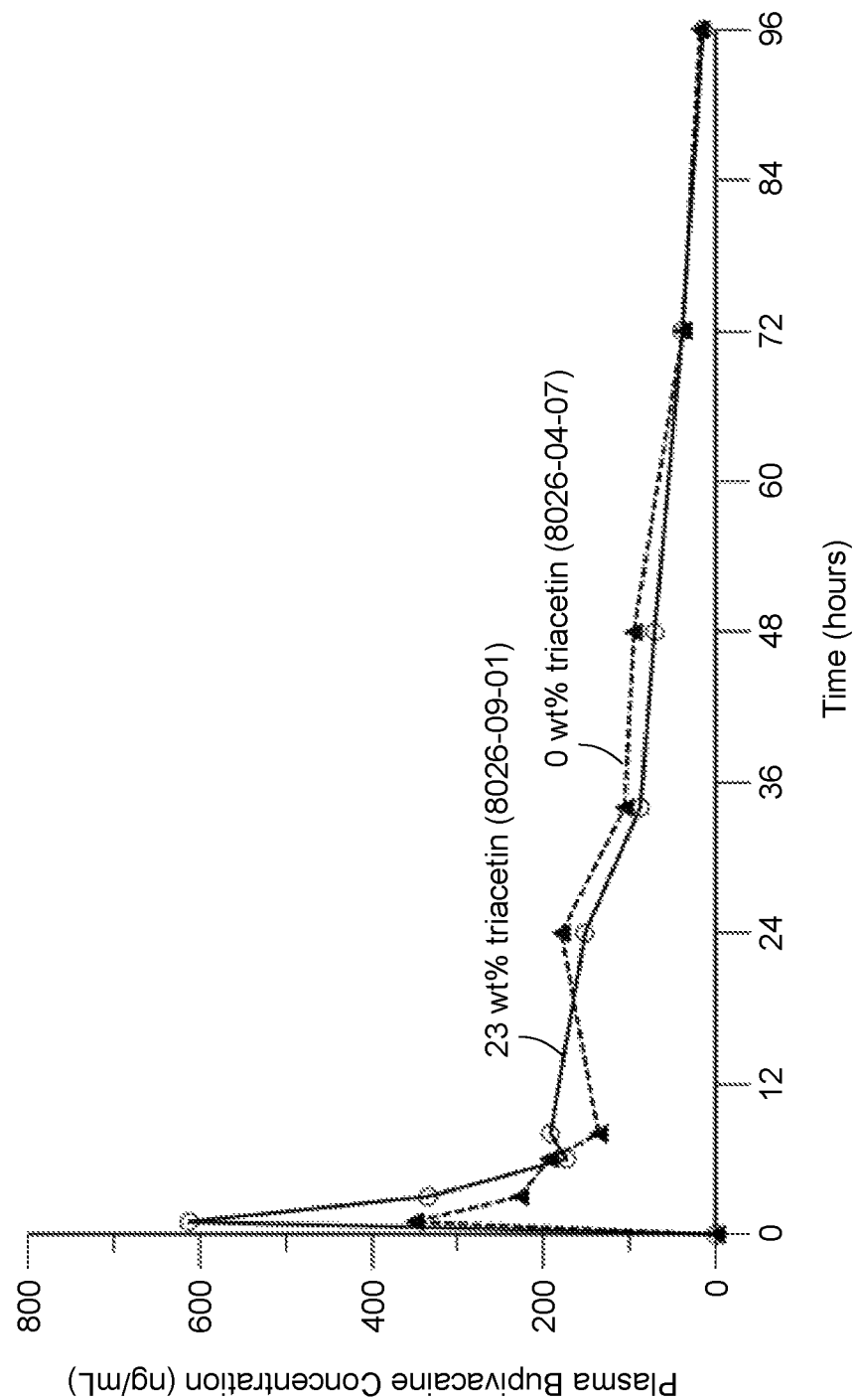
FIGS. 6A-6B are graphs of plasma concentration of bupivacaine (FIG. 6A) and of meloxicam (FIG. 6B), in ng/mL, as a function of time, in hours, after administration in vivo of exemplary compositions comprised of a polyorthoester delivery vehicle comprising triacetin (open circles) or no triacetin (triangles) with bupivacaine and meloxicam.
Figure 6B:
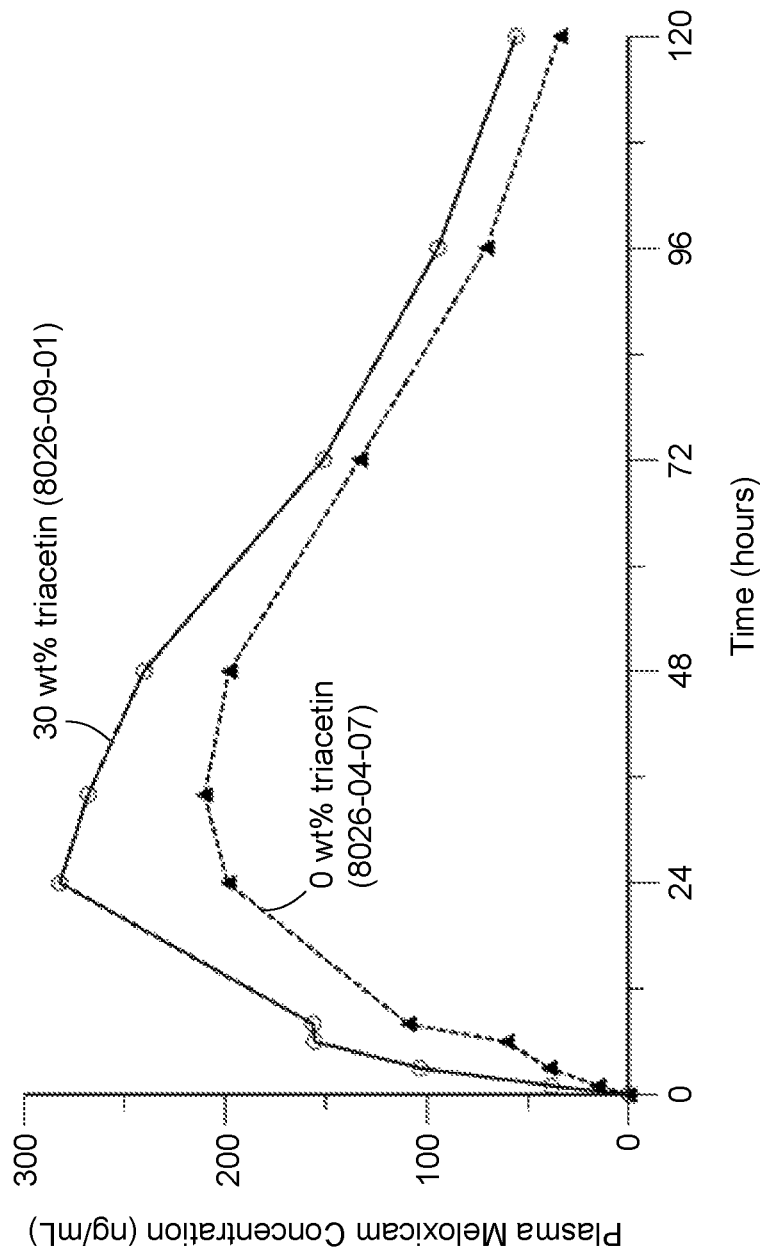

The composition with the triglyceride viscosity reducing agent was compared to the composition with no triglyceride viscosity reducing agent in a canine pharmacokinetic study, as described in Example 10. Dogs received two separate injections of a test composition, and blood samples were collected from each dog at the predetermined time points. The blood samples were subsequently analyzed for bupivacaine and meloxicam plasma concentrations. The data is shown in FIGS. 6A-6B. The data indicates that the compositions provide very similar plasma PK profiles with only a small increase in Cmax for the composition comprising a triglyceride viscosity reducing agent (open circles) in relation to the composition lacking the triglyceride viscosity reducing agent (triangles).

FIGS. 6A and 6B are graphs demonstrating very similar plasma concentration curves for bupivacaine and meloxicam, respectively, for two illustrative compositions described in Example 9. The illustrative compositions: 8026-04-07 (5.0 wt % bupivacaine, 0.15 wt % meloxicam, 79.3 wt % polyorthoester, 0.6 wt % maleic acid and 15% N-methyl pyrrolidone [aprotic solvent]) and 8026-09-01 (3.84 wt % bupivacaine, 0.11 wt % meloxicam, 60.96 wt % polyorthoester, 0.46 wt % maleic acid, 23.08 wt % triacetin, and 11.5 wt % N-methyl pyrrolidone [aprotic solvent]). In these particular compositions, the viscosity of the undiluted composition (8026-04-07) is approximately 70,000 mPa-s at 25° C. while the viscosity of the triacetin containing composition is approximately 7,000 mPa-s at 25° C. The plasma concentration curves for bupivacaine and meloxicam indicate that, with the exception of a slightly higher Cmax, the plasma concentrations curves for the triacetin diluted composition, 8026-09-01, is nearly identical to the plasma concentration curves for the undiluted composition, 8026-04-07. While these investigations demonstrate that compositions can be formulated with triacetin to yield compositions with reduced viscosity with only modest changes in the drug release kinetics, it is recognized compositions can be further optimized with respect to viscosity and drug release kinetics by further adjustments to the composition, such as by modulation of the concentration of polar aprotic solvent, triacetin or other components of the composition.

In another study, described in Example 10, delivery systems comprising a combination of an amide-type local anesthetic and an enolic-acid NSAID with a triglyceride viscosity reducing agent were prepared. The compositions are summarized in Table 10-1 in Example 10. The viscosity of the compositions was measured (according to the procedure in the Methods section of the Examples), and is shown in Table 10-1. The addition of triglyceride viscosity reducing agent to the compositions decreased the viscosity at least 10-fold, at least 20-fold, or at least 40-fold, or more, as compared to compositions lacking the triglyceride viscosity reducing agent.

The in vitro release of bupivacaine and meloxicam from the compositions of Table 10-1 was measured in the test described in Example 11. Tables 11-1 and 11-2 in Example 11 shows the cumulative percent release of bupivacaine and meloxicam, respectively, from the compositions. The compositions provided an in vitro release of both drugs over an extended time period of 3 days or more.

Figure 7A:
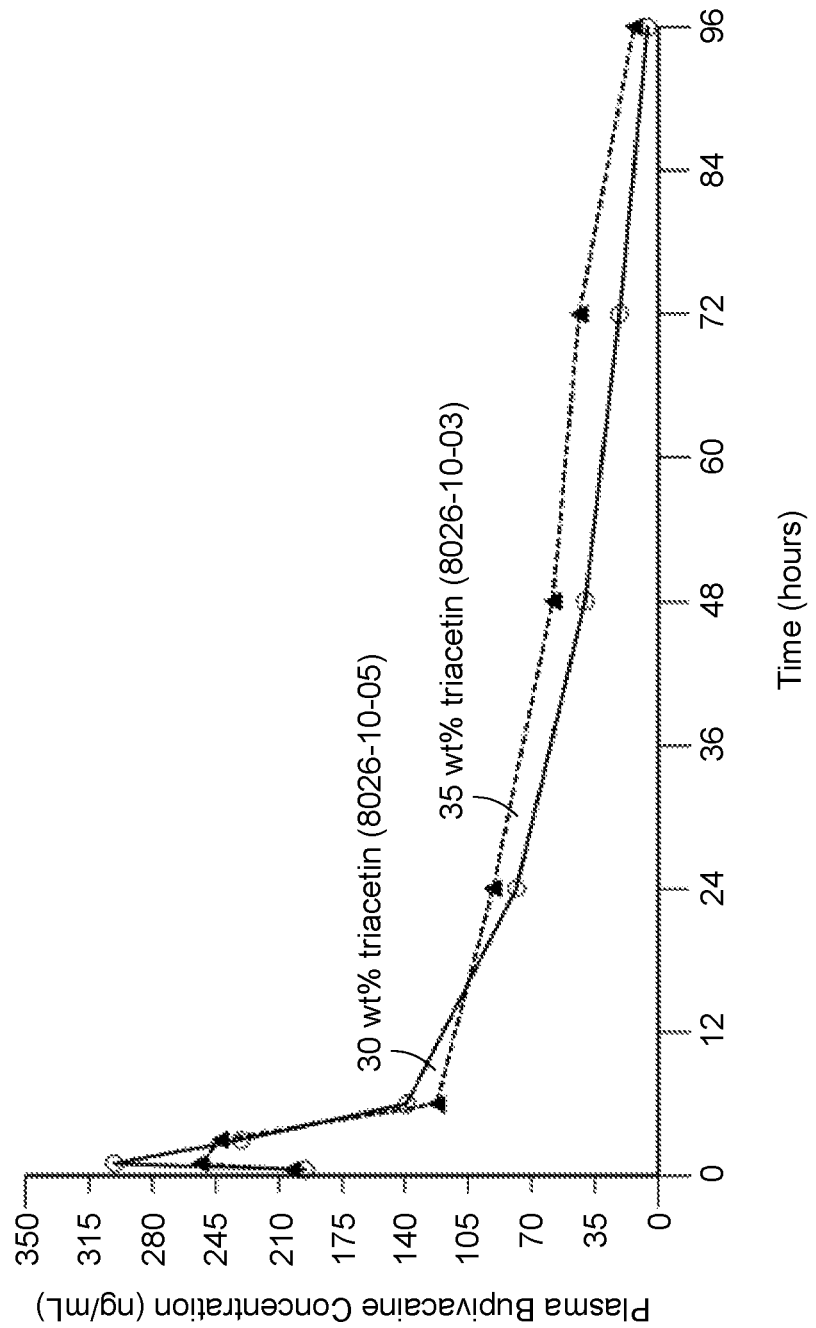
FIGS. 7A-7B are graphs of plasma concentration of bupivacaine (FIG. 7A) and of meloxicam (FIG. 7B), in ng/mL, as a function of time, in hours, after administration in vivo to dogs of exemplary compositions comprised of bupivacaine and meloxicam in a polyorthoester delivery vehicle comprising 30 wt % triacetin (open circles, composition no. 8026-10-05) or 35 wt % triacetin (triangles, composition no. 8026-10-03)
Figure 7B:
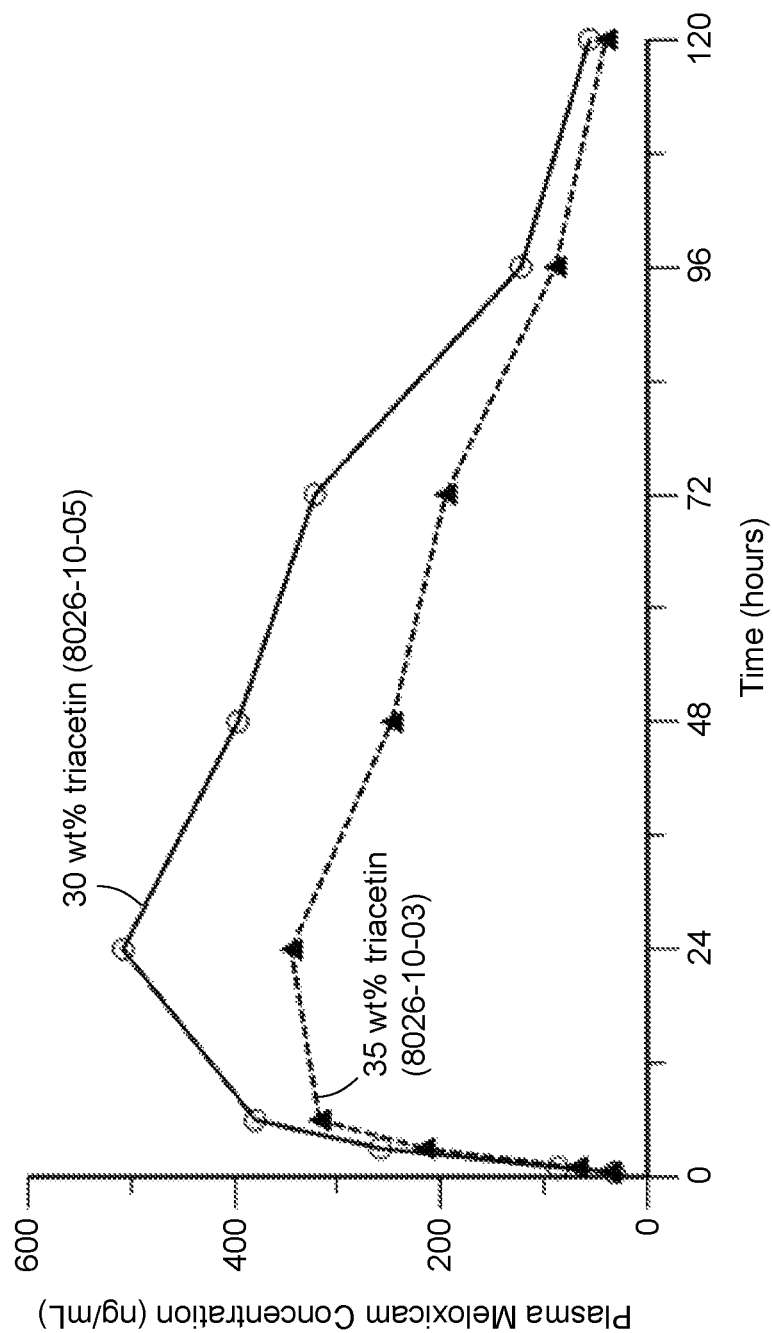

An in vivo pharmacokinetic study was conducted to evaluate the release of drug from delivery systems comprising bupivacaine and meloxicam and a triglyceride viscosity reducing agent. As described in Example 12, dogs were treated with 2 mLs of the composition identification nos. 8026-10-03 and 8026-10-05 (Example 10, Table 10-1) in two separate injections. Blood samples were taken and the plasma analyzed for bupivacaine and meloxicam concentrations. The data from the study is shown in FIGS. 7A-7B. The compositions provided measurable plasma concentrations of bupivacaine (FIG. 7A) and meloxicam (FIG. 7B) over a period of at least 96 hours following administration, where the composition with 35 wt % triacetin (8026-10-03) is indicated by the triangles and the composition with 30 wt % triacetin (8026-10-05) is represented by the open circles.

The reduced viscosity of the compositions comprising a triglyceride viscosity reducing agent and no significant alteration of kinetic release of drug from the composition, relative to a similar composition lacking the triglyceride viscosity reducing agent, provides an opportunity for use of the compositions in clinical settings where the composition is injected via needle, as in a nerve block. Accordingly, a study was conducted to evaluate use of the compositions as a nerve block. As described in Example 13, four grams of each composition set forth in Table 13-1 were injected into each of 4 animals and administered so as to be near the sciatic nerve in one flank of the pig. To assess the degree of nerve block, Von Frey filaments (Ugo Basile) were applied at the dorsal source surface of the foot as described in Example 13. The results of the Von Frey assay are presented in FIG. 8.

Figure 8:
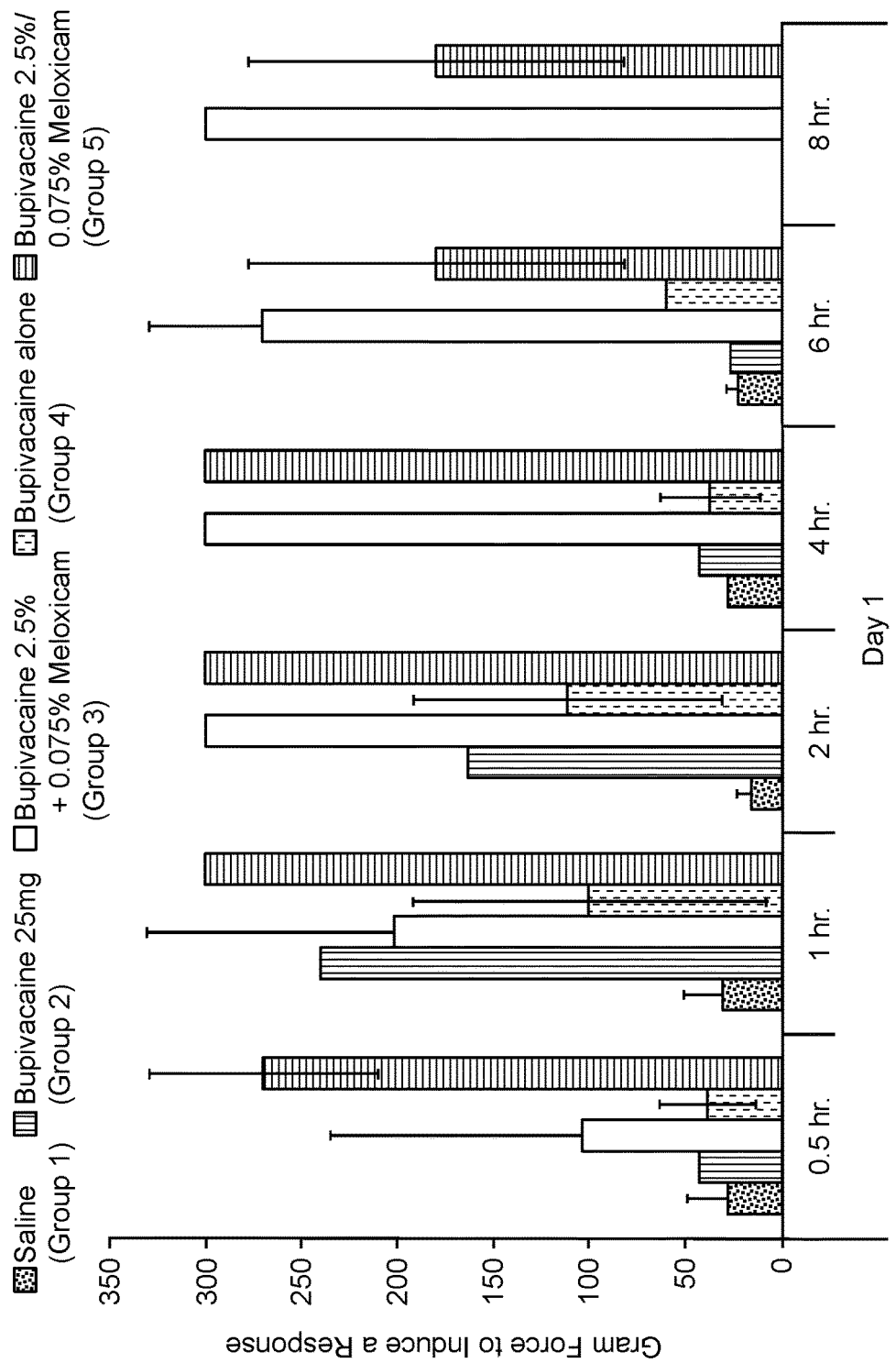
FIG. 8 is a bar graph of withdrawal force, in gram force, as a function of time, in hours and days, after administration in vivo to pigs of compositions comprised of a polyorthoester delivery vehicle, 2.5 wt % bupivacaine alone (Group 4, 8026-13-01, vertical dashes fill) or 2.5 wt % bupivacaine, 0.075 wt % meloxicam and 0.15% maleic acid (Group 3, 8026-10-01, no fill, open bars) or 0.10 wt % maleic acid (Group 5, 8026-10-02, horizontal line fill), or a buffered solution of 0.5 wt % bupivacaine (vertical line fill, Group 2); bars with dotted fill represent the response for the control group treated with saline.

FIG. 8 is a bar graph of withdrawal force, in gram force, as a function of time, in hours and days, after administration in vivo to pigs of compositions comprised of a polyorthoester delivery vehicle, 2.5 wt % bupivacaine alone (Group 4, 8026-13-01, vertical dashes fill) or 2.5 wt % bupivacaine, 0.075 wt % meloxicam and 0.15% maleic acid (Group 3, 8026-10-01, no fill, open bars) or 0.10 wt % maleic acid (Group 5, 8026-10-02, horizontal line fill), or a buffered solution of 0.5 wt % bupivacaine (vertical line fill, Group 2); bars with dotted fill represent the response for the control group treated with saline. The data shows that animals administered a composition comprising both bupivacaine and meloxicam had a higher threshold for responding to pressure. The efficacy of the combination compositions containing both bupivacaine and meloxicam were longer lasting and provided deeper anesthesia than did a similar composition containing bupivacaine but without meloxicam.

The data in FIG. 8 shows the effectiveness of several compositions as a nerve block using the in vivo porcine model. The lower viscosity polymer delivery compositions comprising bupivacaine and meloxicam, when administered as a nerve block, maintained the advantage of the bupivacaine and meloxicam combination to provide longer lasting and deeper anesthesia as compared to bupivacaine in the absence of meloxicam. The polyorthoester compositions having low viscosities, such as a viscosity between 2000 mPa-s and 4000 mPa-s, measured at 25 C using a viscometer, were surprisingly effective as a nerve block. One might expect the lower viscosity to result in a drug release rate too rapid for effective extended release, but the data show otherwise.

It will be appreciated that the use of a triglyceride viscosity reducing agent can be utilized in a polyorthoester delivery system for a variety of therapeutic agents. An illustrative example is provided in Example 14, where a delivery system comprising a polyorthoester polymer, a short chain triglyceride viscosity reducing agent, and a polar aprotic solvent and an anti-emetic therapeutic agent was prepared. In one embodiment, the anti-emetic is used to treat emesis induced by a chemotherapeutic agent, by radiation-induced nausea and vomiting, and/or by post-operative induced nausea and vomiting in a patient. The treatment includes administering to the patient the composition comprising an anti-emetic, such as a 5-HT3 antagonist, where the composition is designed to yield a rate of release for effective anti-emetic therapy. In an exemplary embodiment, the anti-emetic is granisetron. The delivery system can be administered, e.g., intravenously. As seen in the data presented in Table 14-1 of Example 14, the addition of the triglyceride viscosity reducing agent triacetin to the compositions decreased the viscosity between about 5-fold and 90-fold as compared to compositions lacking a triglyceride viscosity reducing agent. The reduction in viscosity, when viscosity is measured at 25° C. using a viscometer (see the Method set forth below), in one embodiment, is at least about 5 fold, at least about 7-fold, at least about 20 fold, at least about 30 fold, at least about 40 fold, at least about 50 fold, at least about 60-fold, at least about 70-fold, at least about 80-fold or at least about 90-fold. The addition of a triglyceride viscosity reducing agent to the compositions decreased the viscosity, when measured at 37° C. using a viscometer, by at least about 5 fold or by at least about 10-fold, or by at least about 20-fold, or by at least about 30-fold.

The in vitro release of granisetron from the compositions of Example 14 was determined as described in Example 15. Cumulative drug release is summarized in Table 15-1 of Example 15 and shows that release of the drug is comparable with the drug release profile across compositions with and without varying triacetin concentrations. There was an increase in the in vitro release rate when the concentration of polar aprotic solvent was increased. Decreasing the viscosity by increasing the amount of polar aprotic solvent increased the drug release by about 2-fold. However, the same increase in triacetin concentration did not cause the same increase in rate of release. Additionally, the compositions provided release of granisetron for at least about 3 days or at least about 4 days. The addition of a triglyceride viscosity reducing agent to reduce viscosity of the compositions did not alter the in vitro release of granisetron relative to a similar composition lacking the a triglyceride viscosity reducing agent. This is seen in the data of Table 15-1 by comparing composition number 8026-14-03, with no triacetin, and 8026-14-04, with 10% triacetin. Release of granisetron from the triacetin composition (which had a nearly 20-fold lower viscosity at 25° C.) was within 10% of the granisetron cumulative release provided by a similar composition lacking the triacetin. Similarly, a comparison of 8026-14-01 (with no triacetin) and 8026-14-02 (with 10 wt % triacetin) reveals that the triacetin-containing composition with a 7-fold lower viscosity at 25° C. released granisetron at a rate within about 15% of the release provided by the composition with no triacetin at the 24 hour, 72 hour and 96 hour time points. Accordingly, in one embodiment, compositions with a triglyceride viscosity reducing agent have a viscosity that is at least about 5-fold or 10-fold (or more, as noted above) when viscosity is measured at 25° C. using a viscometer, and a release of active agent that is within about 20%, 15% or 10% of the release of agent from a similar composition lacking the triglyceride viscosity reducing agent at least one time point, at least two time points or at least three time points during a 96 hour period.

The reduced viscosity compositions as described above are suitable for administering to a subject in need thereof. For example, a low viscosity composition containing a therapeutically effective amount of the one or more active agents can be administered subcutaneously, intradermally or intramuscularly to a subject in need of the active agent(s), or applied topically or instilled into tissue or, e.g., a wound (surgical or otherwise).

The low viscosity compositions and systems comprising a triglyceride viscosity reducing agent such as triacetin, as disclosed herein, are administered to a subject (e.g., patient) in need of treatment for or prevention of a condition, in an effective amount of the flowable composition described herein. These low viscosity compositions provide the advantages of liquid delivery systems for active agents with the delivery profile of viscous polymer or solid polymer delivery systems. The present low viscosity compositions comprising a triglyceride viscosity reducing agent such as triacetin also enable the use of smaller gauge needles compared to other liquid polymer systems. The use of biodegradable polymers in the present compositions comprising a triglyceride viscosity reducing agent, such as triacetin, also allows the rate of release of an active agent and degradation of the flowable composition to be varied over a wide range in contrast to the non-polymeric flowable compositions.

Each composition as disclosed herein comprising a polymer such as a polyorthoester can be characterized in terms of release of the active agent(s) dissolved or dispersed within it. For example, release of one or more drugs from the composition can be determined by placing a small amount of each polymer formulation (e.g., 50 to 500 mg) into a volume of buffer (e.g., 150 mL phosphate buffered saline in an appropriate container). The sample is then incubated at, for example, 25° C., 37° C. or 50° C., with or without agitation. At intervals of time, e.g., every 6 hours, 12 hours, or 24 hours, aliquots of the buffer solution are removed and analyzed for the presence of active agent. Analysis can be performed by, for example, high performance liquid chromatography.

B. Methods of Treatment

The compositions provided can be used, for example, in managing pain in a patient. Accordingly, methods of ameliorating pain, managing pain, treating pain and/or providing local anesthesia to a patient in need thereof are provided. In another embodiment, a method for the prophylactic treatment of pain is provided, such as in the situation of managing or treating post-operative pain. In other embodiments, provided is a method for extending the pain-relief profile of a polyorthoester composition comprising an the amide- or anilide-type local anesthetic by incorporating therein, an efficacy-enhancing amount of an enolic-acid NSAID such as meloxicam, to thereby provide a composition capable of providing effective pain relief for a period of time that is extended over that of the same composition absent the NSAID. In particular, the composition comprising a combination of an amide-type anesthetic and an enolic-acid NSAID is effective to provide pain relief from about 1 day to at least about 2 days or at least about 3 days or at least about 4 days or at least about 5 days following administration, i.e., is a long-acting composition for pain relief, rather than a short-acting composition. In other embodiments, the composition provides relief of pain for a period of up to about 4 days or up to about 5 days.

In yet an additional aspect, provided is a method for altering the analgesic or pain relief effect of a polyorthoester composition comprising an the amide-type local anesthetic by incorporating therein, an efficacy-enhancing amount of an enolic-acid NSAID, to thereby provide a composition having an analgesic or pain relief effect for at least 5 hours that optionally exhibits a decrease in the analgesic or pain relief effect, e.g., as demonstrated in an in-vivo model for post-operative pain, e.g., from about 5-24 hours following administration, see, e.g., Example 8, followed by a period in which the composition maintains or regains its analgesic or pain relief effect, from about 1 day to 2 days, days post-administration, such that the composition exhibits a long-term the analgesic or pain relief effect from about 2 days to about 5 days post-administration, and optionally beyond, that is at least about 75% or at least about 50% of its average analgesic or pain relief effect exhibited from about 1-5 hours post-administration.

The composition is effective, in one embodiment, to provide measurable plasma concentrations of the amide- or anilide-type local anesthetic type local anesthetic and/or the enolic-acid NSAID for a period of up to 5 days following administration.

In a particular embodiment, the composition is effective to release a significant portion of both the amide- or anilide type local anesthetic and the NSAID from the composition, such that 80% by weight or more of both drugs are released over a period of about 5 days or up to at least about 5 days. In one embodiment, both drugs are released for a period of between at least about 1 day to up to about 5 days, and in another embodiment for a period of between about 1-5 days or from about 2-3 days, or for at least about 3 days. Although in some cases the amide- or anilide type local anesthetic may be released from the composition in approximately the same amount and over approximately the same time frame as essentially the same composition further comprising an NSAID, such as, for example, meloxicam, the incorporation and release of the NSAID from the composition is effective to enhance the efficacy of the local-type anesthetic by an amount that exceeds that expected from the incorporation of the NSAID-type drug, such that the effect of the NSAID on the composition is synergistic rather than additive in nature.

In another aspect, provided is a method of treatment, the method comprising dispensing from a needle a composition comprising an amide- or anilide type local anesthetic combined with an NSAID, such as an enolic-acid NSAID, and a polyorthoester, to thereby achieve a controlled release of both the local anesthetic and the NSAID from the composition, wherein 80% by weight or more of both drugs are released over a period of about 5 days.

In another embodiment, the compositions provided herein are for use in a method of providing local anesthesia to a patient in need thereof. The treatment includes administering to a patient a composition as set forth herein, e.g., comprising an amide or anilide-type local anesthetic, an NSAID, and a delivery vehicle, where in some embodiments, the delivery vehicle is a polyorthoester and the NSAID is an enolic-acid NSAID. The method provides rates of release of both the anesthetic and the NSAID, as well as accompanying pharmacokinetic profiles of each effective for reducing or preventing pain over an extended period following application. Local administration can be, e.g., near a nerve, into the epidural space, intrathecal, or directly to a surgical site or to a surgical wound or a non-surgical wound (e.g., instillation, subcutaneous injection or intradermal injection to a wound area). Subcutaneous injection to a wound, in some embodiments, is achieved via local infiltration analgesia (LIA). LIA is an analgesic technique that has gained popularity since it was first brought to widespread attention by Kerr and Kohan in 2008. The technique involves the infiltration of a large volume dilute solution of a long-acting local anesthetic agent, often with adjuvants (e.g., epinephrine, ketorolac, an opioid), throughout the wound at the time of surgery.

In one embodiment, the extended period is for at least about 5 days. In another embodiment, the extended period is for up to about 5 days. In still another embodiment, the extended period from about 1 day to at least about 5 days or from about 1 day to up to about 5 days. In yet another embodiment, the extended period is for about 3 days.

In the methods, in one embodiment, about 80% by weight or more of both drugs are released over a period of about 5 days. The composition, in one embodiment, is effective to provide significant pain relief for at least about 5 days following application.

A method for providing pain relief to a patient in need thereof is provided, where the method comprises providing a composition as described herein, and instructing that the composition be administered to the patient to provide pain relief for an extended period. In one embodiment, the extended period is for at least about 5 days. In another embodiment, the extended period is for up to about 5 days. In still another embodiment, the extended period from about 1 day to at least about 5 days or from about 1 day to up to about 5 days. In yet another embodiment, the extended period is for about 3 days.

The compositions and delivery systems provided herein may also be used for managing, reducing or treating acute or chronic pain. The compositions may also be used for the prophylactic treatment of acute or chronic pain. Acute pain can be associated with, for example, surgery, broken bones, dental work, burns or cuts or labor and childbirth. Chronic pain can be associated with, for example, headache, low back pain, cancer pain, arthritis pain, neurogenic pain and psychogenic pain.

In terms of administration for any of the methods described herein, the compositions may be injected, instilled, or applied with standard syringes and needles (e.g., about 16 gauge), or may be applied with, e.g., a spray applicator. The compositions may be injected subcutaneously, intradermally or intramuscularly. The compositions may be applied to a wound topically or subcutaneously. The compositions may also be applied perineurally, as described in more detail below. The compositions may be applied using various methods known in the art, including by syringe, injectable or tube dispenser.

In one aspect, the compositions described herein which comprise an amide-type local anesthetic and an NSAID are contemplated for administration as a peripheral nerve block. In particular, the compositions described above that comprise a triglyceride viscosity reducing agent are contemplated for use as a nerve block. A peripheral nerve block involves the introduction of an agent near or in a peripheral nerve for the reduction of pain or to provide numbness. Types of peripheral nerve blocks include but are not limited to motor, sensory, differential, and autonomic blocks, and additionally, include but are not limited to brachial plexus (axillary, interscalene, supraclavicular, infraclavicular), individual upper extremity nerve blocks (median, radial, ulnar, musculocutaneous, axillary), sciatic, ankle, metatarsal, oral, femoral, popliteal fossa, saphenous, distal, digital, deep peroneal, superficial peroneal, tibial, sural, and saphenous blocks.

In this aspect, injection to a location adjacent to a nerve or nerve plexus requires a composition having a relatively low viscosity (e.g., a viscosity of less than about 5000 mPa-s, 4000 mPa-s, 3000 mPa-s, 2000 mPa-s, or 1000 c mPa-s, or between about 250 mPa-s to 5000 mPa-s, 250 mPa-s to 3000 mPa-s, 500 mPa-s to 5000 mPa-s, 500 mPa-s to 3000 mPa-s, 1000 mPa-s to 3000 mPa-s, 1000 mPa-s to 4000 mPa-s, 1000 mPa-s to 5000 mPa-s, 2000 mPa-s to 4000 mPa-s, 1500 mPa-s to 2500 mPa-s, 2500 mPa-s to 3500 mPa-s, 3500 mPa-s to 4500 mPa-s, 2750 mPa-s to 3000 mPa-s, 3000 mPa-s to 3750 mPa-s, or 3750 mPa-s to 4000 mPa-s when measured at room temperature (about 25° C.). One means for reducing the viscosity of a formulation is to prepare the composition using about 40 wt % to 60 wt %, 45 wt % to 55 wt %, 50 wt % to 60 wt %, or 50 wt % to 55 wt % of polyorthoester, such as Formula I, about 2% to 10%, 3% to 10%, 2% to 5%, 3% to 5%, 2% to 4%, 3% to 4%, or 3% to 8% of a polar aprotic solvent, and about 25 wt % to 45 wt %, 30 wt % to 45 wt %, 35 wt % to 45 wt %, or 35 wt % to 40 wt % of triacetin. The polar aprotic solvent which may be used includes but is not limited to DMSO and NMP. The composition further includes an amide-type local anesthetic and an amide-type local anesthetic and a non-steroidal anti-inflammatory drug (NSAID) at a total wt % of about 1 wt % to 12 wt %, or of about 2 wt % to 7 wt %. For example, the composition can include 1.25 wt % to 10 wt % bupivacaine and 0.075 wt % to 1.5 wt % meloxicam. To prepare the composition for administration as a nerve block, the appropriate amount of amide- or amino-anilide-type local anesthetic is dissolved into a polar aprotic solvent and mixed until dissolved. In one embodiment, the anesthetic is dissolved in the aprotic solvent at a temperature between about 60° C. to 85° C. or at about 70° C. An organic acid, for example, maleic acid, is then added and dissolved, followed by addition of the NSAID, for example, meloxicam. The appropriate amounts of polymer and triacetin are mixed separately and heated (e.g., at between about 60° C. to 80° C. or at 70° C.) and thoroughly mixed. The solution containing the NSAID and anesthetic is then combined with the desired amount of polymer and triacetin blend, and then mixed at an elevated temperature until homogeneous.

Addition of the triacetin to the composition comprising the amide-type local anesthetic and NSAID (e.g., bupivacaine and meloxicam) is shown herein (see, e.g., Example 9 and Example 13) to reduce the viscosity of the composition, thereby making it more suitable for a nerve block injection. Studies to measure blood levels of active agent released by a nerve block formulation show minimal effects of triacetin on the pharmacokinetic profile of the drug delivery composition. In other words, an unexpected benefit arose from formulating a reduced-viscosity composition which can be injected as a nerve block, and despite its reduced viscosity, provides sustained release of the active agents and corresponding sustained pain relief. In a particular embodiment, the anesthetic is bupivacaine and the NSAID is meloxicam.

EXAMPLES

The following examples are illustrative in nature and are in no way intended to be limiting.

Methods:

Viscosity measurements were performed using a Brookfield Viscometer DV-II Pro with a CPA-44PSYZ cup and measured at 25° C. and or 37° C. Viscosity measurements of formulations with less than 8,000 cP (mPa·s) were measured at 25° C. using a CPA-40Z spindle and the system was verified using 1,000 mPa·s silicone oil Brookfield Viscosity Standard. Viscosity measurements for formulations above 8,000 cP (mPa·s) were evaluated using a CPA-52Z spindle and standardized using the 30,000 mPa·s silicone oil Brookfield Viscosity Standard.

Materials:

Each of the illustrative compositions described in Examples 1-13 comprises a polyorthoester (POE) of Formula I, comprising 80% triethylene glycol (TEG) and 20% TEG-glycolide (comprising on average 2 glycolides per subunit, i.e., TEG-diglycolide). See, e.g., U.S. Pat. No. 8,252,305, Example 1(d).

Example 1

Composition Comprising Ropivacaine and a Non-Steroidal Anti-Inflammatory Drug

A composition containing the polyorthoester of Formula I, an aprotic solvent, ropivacaine, and meloxicam was prepared with the amount of each component set forth in Table 1-1 below. The composition was prepared by dissolving the NSAID into the aprotic solvent at approximately 80° C. and then adding the ropivacaine with heating until dissolved, to form a drug solution. The drug solution was mixed with the polyorthoester at an elevated temperature, until homogeneous.

TABLE 1-1

| Composition ID | Solvent ID | Ropivacaine Base % | Meloxicam % | % Polyorthoesters | % Solvent |
|---|---|---|---|---|---|
| 8026-01-01 | NMP | 5.2% | 3.6% | 61.5% | 29.7% |

*NMP = N-methylpyrrolidone; POE = polyorthoester

Example 2

In Vitro Release of Ropivacaine and Meloxicam from a Polyorthoester Composition

The release of ropivacaine and meloxicam from the composition in Example 1 was determined by placing 50 mg of the polymer composition from Example 1 into a vial filled with 150 mL of phosphate buffered saline (PBS). The vial was then incubated at 37° C. without agitation. At 24 hour intervals, 1 mL samples of the PBS were taken from the vial without agitation of the solution. Each sample was analyzed by HPLC to determine the concentration of ropivacaine and meloxicam. The cumulative drug release as a function of time from the 50 mg depot was determined. Results are shown in Table 2-1 below.

TABLE 2-1

In Vitro Release of Ropivacaine and Meloxicam

| | | Cumulative Percent Drug Released for Composition | | |
|---|---|---|---|---|
| Composition # | Drug | 24 hrs | 48 hrs | 72 hrs |
| 8026-01-01 | Ropivacaine | 52.8 | 88.5 | 100.0 |
| 8026-01-01 | Meloxicam | 39.0 | 85.3 | 100.0 |

Example 3

Delivery Systems Comprising Bupivacaine and Diclofenac

Compositions containing between approximately 62-63% polyorthoester of Formula I, between approximately 15-20% of an aprotic solvent, between 10% and 15% bupivacaine base, and 6% to 7.5% diclofenac were prepared. The compositions were prepared by first dissolving an appropriate amount of diclofenac into an appropriate amount of aprotic solvent at approximately 80° C. and then dissolving bupivacaine into the solution. The drug solution was then mixed with an appropriate amount of polymer at an elevated temperature, until homogeneous. Exemplary compositions are presented in Table 3-1.

TABLE 3-1

| Composition ID | Solvent ID | Wt % Bupivacaine | Wt % Diclofenac | Wt % POE | Wt % Solvent |
|---|---|---|---|---|---|
| 8026-03-01 | NMP | 10.2% | 6.06% | 63.52% | 20.22% |
| 8026-03-02 | NMP | 15.0% | 7.5% | 62.0% | 15.5% |

*NMP = N-methylpyrrolidone; POE = polyorthoester

Example 4

Delivery Systems Comprising Bupivacaine and Meloxicam

Compositions containing between approximately 55% to 67% polyorthoester of Formula I, between approximately 16% and 32% of an aprotic solvent, 9.9% to 15% bupivacaine, and 1.5% to 3.4% meloxicam were prepared. The compositions were prepared by first dissolving the appropriate amount of NSAID into an aprotic solvent at approximately 80° C. and then adding the appropriate amount of bupivacaine and heating until dissolved. The drug solutions were then mixed with the appropriate amount of polymer at an elevated temperature, until homogenous. Exemplary compositions are presented in Table 4-1.

TABLE 4-1

| Composition ID | Solvent ID | Wt % Bupivacaine | Wt % Meloxicam | Maleic Acid | Wt % POE | Wt % Solvent |
|---|---|---|---|---|---|---|
| 8026-04-01 | NMP | 9.9% | 3.4% | 0% | 54.6% | 32.1% |
| 8026-04-02 | NMP | 15.0% | 1.5% | 0% | 66.6% | 16.9% |
| 8026-04-03 | NMP | 15.0% | 3.0% | 0% | 65.6% | 16.4% |
| 8026-04-04 | NMP | 10.0% | 0.75% | 1.2% | 73.05% | 15% |
| 8026-04-05 | NMP | 5.0% | 0.38% | 0.6% | 79.02% | 15% |
| 8026-04-06 | NMP | 5.0% | 0.30% | 0.6% | 79.10% | 15% |
| 8026-04-07 | NMP | 5.0% | 0.15% | 0.6% | 79.25% | 15% |
| 8026-04-08 | NMP | 5.0% | 0.08% | 0.6% | 79.32% | 15% |

Example 5

In Vitro Release of Bupivacaine and Meloxicam from Exemplary Compositions

The release of bupivacaine and meloxicam from the compositions described in Example 4 was determined by placing approximately 50 mg to 200 mg of the polymer composition into a vial containing 150 mL of phosphate buffered saline. The vials were incubated at 37° C. with continuous rotation at 60 rpm. At 24 hour intervals, 1 mL samples were taken from the vials without any additional agitation of the solution. Each sample was analyzed by HPLC to determine the concentration of bupivacaine and the concentration of meloxicam. The cumulative drug release from the depot was then calculated. The data is shown in Tables 5-1 and 5-2 and indicate release of both drugs over an extended time period of 3 days or more.

TABLE 5-1

In Vitro Release of Bupivacaine

Cumulative Percent Bupivacaine Released for Compositions

| Composition # | 24 hrs | 48 hrs | 72 hrs | 96 hrs | 120 hrs | 144 hrs | 168 hrs |
|---|---|---|---|---|---|---|---|
| 8026-04-01 | 8.81% | 28.28% | — | — | 66.12% | — | 75.06% |
| 8026-04-02 | 14.56% | 24.91% | 35.04% | 43.77% | 48.46% | 59.76% | 66.35% |
| 8026-04-03 | 10.60% | 19.69% | 27.08% | 33.09% | 37.89% | 42.32% | 36.72% |
| 8026-04-04 | 41.89% | 66.92% | 83.06% | 92.86% | 97.69% | — | — |
| 8026-04-05 | 42.25% | 69.83% | 91.51% | 96.48% | 89.42% | — | — |
| 8026-04-06 | 18.29% | 46.38% | 72.52% | 93.36% | 96.95% | — | — |
| 8026-04-07 | 40.19% | 62.61% | 84.35% | 97.70% | 100.32% | 100.63% | 100.91% |
| 8026-04-08 | 22.76% | 48.85% | 65.53% | 81.66% | 97.07% | — | — |

TABLE 5-2

In Vitro Release of Meloxicam

Cumulative Percent Meloxicam Released for Compositions

| Composition # | 24 hrs | 48 hrs | 72 hrs | 96 hrs | 120 hrs | 144 hrs | 168 hrs |
|---|---|---|---|---|---|---|---|
| 8026-04-01 | 16.98% | 24.48% | — | — | 66.12% | — | 72.54% |
| 8026-04-02 | 7.62% | 11.43% | 17.65% | 31.15% | 34.35% | 38.65% | 34.06% |
| 8026-04-03 | 11.71% | 19.37% | 24.83% | 26.11% | 27.25% | 28.06% | 28.21% |
| 8026-04-04 | 10.97% | 54.94% | 81.11% | 96.13% | 100.18% | — | — |
| 8026-04-05 | 27.05% | 67.45% | 93.62% | 95.15% | 96.14% | — | — |
| 8026-04-06 | 18.23% | 70.17% | 69.21% | 99.60% | 104.01% | — | — |
| 8026-04-07 | 13.36% | 40.20% | 69.94% | 93.12% | 100.39% | 100.98% | 100.80% |
| 8026-04-08 | 41.50% | 74.65% | 93.51% | 98.15% | 99.03% | — | — |

Example 6

In Vivo Administration of Bupivacaine—Meloxicam Compositions

In vivo pharmacokinetic studies were conducted as follows. Sheep weighing between 60 and 100 kg received 4 mL of a composition prepared as described in Example 4: composition no. 8026-04-03 (Study 1, n=6), 8026-04-04 (Study 2, n=3) or 8026-04-05 (Study 2, n=3). Plasma samples were collected from each sheep at the following time points: t=0 (immediately prior to drug administration), 0.5, 1, 3, 6, and 8, 24, and 30 hours post-administration and then daily for days 3-7 (48 through 168 hours). The plasma samples were subsequently analyzed by LC/MS/MS for bupivacaine and meloxicam.

The data from the study is shown in FIGS. 1A-1B, where plasma levels of bupivacaine (FIG. 1A) and of meloxicam (FIG. 1B) are plotted at each time point, for the three compositions—15 wt % bupivacaine/3 wt % meloxicam (closed squares); 10 wt % bupivacaine/0.75 wt % meloxicam (open circles); and 5 wt % bupivacaine/0.38 wt % meloxicam (open triangles). The data indicates that the compositions provide measurable plasma concentrations of bupivacaine and meloxicam over a period of at least 96 hours following administration.

Example 7

In Vivo Administration of Bupivacaine—Meloxicam Compositions

An in vivo pharmacokinetic study was conducted as follows. Beagles (n=5) weighing approximately 10 kg received 1 mL of Composition ID No. 8026-04-07 (Example 4) in two separate injections of approximately 0.5 mL each. Plasma samples were collected from each dog at the following time points: t=0 (immediately prior to drug administration), 0.5, 1, 3, 6, 24, and daily up to day 5 (120 hrs). The plasma samples were subsequently analyzed by LC/MS/MS for bupivacaine and meloxicam.

The data from the study are illustrated in FIGS. 2A-2B and indicate that the compositions provide measurable plasma concentrations of bupivacaine and meloxicam over a period of at least 96 hours following administration.

Example 8

In Vivo Pharmacodynamics of Bupivacaine—Meloxicam Compositions

Various compositions were evaluated for their capacity to reduce post-surgical incisional (post-operative or POP) pain in a porcine model system. In this model, a 7 cm long skin and fascia incision was made in the left flank under general anesthesia. Test composition or control article was applied to the wound. The skin incision was then closed using sterile sutures. All studies described below evaluated 4 pigs per group.

Post-operative pain was assessed using the Von Frey methodology. Von Frey filaments (Ugo Basile) were applied at approximately ~0.5 cm proximal to the incision line to the surface of the flank skin. Filaments of increasing diameter (thicker fibers equate to a higher gram force while thinner fibers equate to a lower gram force) were applied until the animal withdrew from the stimuli (the act of moving away from the stimuli). Each filament was applied 3-5 times. If withdrawal was not achieved, a thicker filament was applied. The maximum force filament was 60 g. If a withdrawal was achieved, a thinner filament was applied. By alternating the filament thickness, the gram force required to achieve withdrawal reaction was determined and recorded. The greater the force that was applied, the more effective the analgesia.

Example 8A

Study 1 evaluated compositions containing bupivacaine or ropivacaine absent an enolic-acid NSAID. An extended release polymer composition containing 15% bupivacaine was compared to an extended release polymer composition containing 5% ropivacaine. The compositions were prepared following the procedure described in Example 1. Following creation of an incision (n=4 pigs/group), each test composition was administered by instilling directly onto the surface of the wound area or by injecting subcutaneously into the lateral margins of the wound. The doses were 2 mL of saline (Group 1), 2 mL of 15% bupivacaine composition (Groups 2 and 3), and 1.8 mL of 5% ropivacaine composition (Groups 4 and 5). Table 8-1 summaries the test groups and compositions. Analgesia was evaluated by response in the von Frey test, as described above. The baseline (pre-surgery) withdrawal score for the von Frey test was 60 g.

TABLE 8-1

Composition of Vehicle Control and Test Articles (Study 1)

| Group | Method of Administration | Dose Volume | API (%) | Vehicle Composition POE % | NMP % |
|---|---|---|---|---|---|
| 1 | Subcutaneous Injection Around Wound | 2.0 | Saline Control | | |
| 2 | Subcutaneous Injection Around Wound | 2.0 | Bupivacaine (15%) | 55% | 30% |
| 3 | Laid onto Wound Surface | 2.0 | | | |
| 4 | Subcutaneous Injection Around Wound | 1.8 | Ropivacaine (5%) | 71% | 24% |
| 5 | Laid onto Wound Surface | 1.8 | | | |

The von Frey response for the animals in each test group is shown in FIG. 3, where withdrawal force, in gram force is shown as a function of time, in hours and days, after administration in vivo to pigs. The test compositions are denoted as follows: (i) 15 wt % bupivacaine administered by injection (vertical dashes fill) or by instillation (vertical line fill) or (ii) 5 wt % ropivacaine administered by injection (horizontal line fill) or instillation (diamond crosshatch fill); and bars with dotted fill represent the response for the control group treated with saline.

Example 8B

A second study (Study 2) was performed to compare extended release formulations containing a local amide-type anesthetic to formulations containing local anesthetics in combination with non-steroidal anti-inflammatory drugs. The nociceptive activity of five different formulations was evaluated in the pig POP model. The compositions are presented in Table 8-2. Extended release formulations containing ropivacaine (slower release and faster release, Groups 2 and 3 respectively) were compared to extended release formulations containing bupivacaine and the NSAIDs diclofenac and meloxicam, Groups 4 and 5 respectively. A dose volume of 2 mL for vehicle or test article was injected subcutaneously into the lateral margins of the incision and the incision closed with sutures. Assessment of nociception by von Frey method at baseline, 1, 3, and 5 hours, and days 1 through 6 after surgery as was described above.

TABLE 8-2

Comparative Compositions used in Study 2

| Group | API (%) | Maleic Acid Wt % | Vehicle Composition POE wt % | NMP wt % |
|---|---|---|---|---|
| 1 | Saline Control | | | |
| 2 | Ropivacaine (5.0) | N/A | 0.6% | 75.5% | 18.9% |
| 3 | Ropivacaine (5.0) | N/A | 0.2% | 71.1% | 23.7% |
| 4 | Bupivacaine (15.0) | Diclofenac (7.5) | 0 | 57.5% | 20% |
| 5 | Bupivacaine (15.0) | Meloxicam (3.5) | 0 | 61.5% | 20% |

Results of Study 2 are shown in FIG. 4, where withdrawal force, in gram force is shown as a function of time, in hours and days, after administration by subcutaneous injection to a wound incision in vivo in pigs, where the test compositions are denoted as follows: (i) 5 wt % ropivacaine with 0.6% maleic acid (horizontal line fill), (ii) 5 wt % ropivacaine with 0.2% maleic acid (diamond crosshatch fill), (iii) 15 wt % bupivacaine and 7.5 wt % diclofenac (vertical dashes fill), or (iv) 15 wt % bupivacaine and 3.5 wt % meloxicam (vertical line fill); and bars with dotted fill represent the response for the control group treated with saline.

Example 8C

A third study, Study 3, was conducted to evaluate five different formulations containing different concentrations of the two active ingredients, bupivacaine and meloxicam. As in the previous studies, 2 mL of each formulation was administered either by 1) subcutaneous injection around the wound margins (8 injections; 4/side) or 2) by direct application to the wound surface created by the incision or 3) injected into the tissues on either side of the wound. The parameters evaluated and the timing for the assessment were the same as in Study 2. Table 8-3 presents the compositions tested.

TABLE 8-3

Composition Tested (Study 3)

| Group | API Bupivacaine (%) | Meloxicam (%) | Vehicle Composition POE (%) | NMP (%) | Maleic Acid |
|---|---|---|---|---|---|
| Group 1 | 10.0 | 0.75 | 74.25 | 15 | 1.2 |
| Group 2 | 10.0 | 0.38 | 73.42 | 15 | 1.2 |
| Group 3 | 5.0 | 0.75 | 78.65 | 15 | 0.6 |
| Group 4 | 15.0 | 1.50 | 66.7 | 15 | 1.8 |
| Group 5 | 5.0 | 0.38 | 79.02 | 15 | 0.6 |

The results showed that all bupivacaine/meloxicam compositions demonstrated good analgesia through Day 6 consistent with the previous study (data not shown). There was no significant benefit to bupivacaine concentrations greater than 5%. A dose response for meloxicam was not observed.

Example 8D

Compositions containing 5% bupivacaine with varying concentrations of meloxicam ranging from 0.08 to 0.4% were tested, along with a composition containing meloxicam alone (i.e., containing no local anesthetic). For the meloxicam-only composition, meloxicam was dissolved in a water/t-butyl alcohol mixture and the pH was adjusted to 11. The solution was then lyophilized. The appropriate amount of lyophilized meloxicam was dissolved in an aprotic solvent, DMSO, at approximately 80° C. The resultant drug solution was then mixed with the appropriate amount of polymer at an elevated temperature until homogeneous. Additionally, compositions containing 5% ropivacaine with and without meloxicam were also evaluated to determine if the synergistic effect of meloxicam and bupivacaine extended to other local anesthetics.

The compositions tested and group assignments are presented in Table 8-4. All test compositions were administered to pigs as subcutaneous injections into both sides of the incision (8 injections; 4/side) at a total dose of 2 mL. The parameters evaluated and the timing for the assessment were the same as in Study 2.

TABLE 8-4

Composition of Vehicle Control and Test Articles

| Group | API Bupivacaine (%) | Ropivacaine (%) | Meloxicam (%) | Vehicle Composition POE (%) | NMP (%) | Maleic Acid (%) |
|---|---|---|---|---|---|---|
| 1 | 5.0 | — | 0.19 | 79.21 | 15.0 | 0.60 |
| 2 | 5.0 | — | 0.08 | 79.32 | 15.0 | 0.60 |
| 3 | 5.0 | — | 0.30 | 79.10 | 15.0 | 0.60 |
| 4 | — | — | 0.16 | 84.84 | 15 | — |
| 5 | — | 5.0 | 0.38 | 72.45 | 22.0 | 0.17 |
| 6 | — | 5.0 | — | 72.75 | 22.0 | 0.25 |

Results are shown in FIGS. 5A-5B, where withdrawal force, in gram force, is shown as a function of time, in hours and days, after administration of the test formulations, denoted as follows: compositions comprised of a polyorthoester delivery vehicle and 5 wt % bupivacaine in combination with meloxicam at 0.08 wt % (vertical dash fill), 0.19 wt % meloxicam (vertical line fill), and 0.3 wt % meloxicam (horizontal line fill), a composition comprised of a polyorthoester delivery vehicle and 0.15 wt % meloxicam alone (dotted fill) (FIG. 5A) and compositions comprised of a polyorthoester delivery vehicle and 5 wt % ropivacaine in combination with 0.38 wt % meloxicam (diamond crosshatch fill) or with 5 wt % ropivacaine alone (no fill; open bars).

Example 9

Polymer Compositions Comprising Bupivacaine and Meloxicam and a Viscosity Reducing Triglyceride The composition identified as 8026-04-07 in Example 4 was prepared to include 30% triacetin (glycerol triacetate) and assigned identification no. 8026-09-01. Viscosity of the triacetin-containing composition was measured as set forth in the Methods section above and was 7,115 mPa-s at 25° C. Viscosity of a similar composition with no triacetin was approximately 75,000 mPa-s at 25° C. when measured as set forth in the Methods section above.

TABLE 9-1

| Composition ID | Wt % NMP | Wt % Triacetin | Wt % Bupivacaine | Wt % Meloxicam | Maleic Acid | Wt % Polyorthoester |
|---|---|---|---|---|---|---|
| 8026-04-07 | 15% | N/A | 5.0% | 0.15% | 0.6% | 79.25% |
| 8026-09-01 | 11.57% | 23.05 | 3.86 | 0.12 | 0.46 | 60.94 |

The composition with the triglyceride viscosity reducing agent was compared to the composition with no triglyceride viscosity reducing agent in a canine pharmacokinetic study. The in vivo pharmacokinetic study was conducted as follows. Beagles (n=5), weighing approximately 10 kg, received 1 mL of composition identification no. 8026-04-07 in two separate injections of approximately 0.5 mL. A separate set of beagles (n=5), also weighing approximately 10 kg, received 1.3 mL of composition identification no. 8026-09-01 in two separate injections of approximately 0.65 mL each (total of 1.3 mL). Plasma samples were collected from each dog at the following time points: t=0 (immediately prior to drug administration), 1, 3, 6, 8, 24, and 34 to 36 hours post-administration, and then daily for days 3-7 (48 through 168 hours). The plasma samples were subsequently analyzed by LC/MS/MS for bupivacaine and meloxicam.

The data from the study is shown in FIGS. 6A-6B. The data indicates that the compositions provide very similar plasma PK profiles with only a small increase in Cmax for the composition comprising a triglyceride viscosity reducing agent (open circles) in relation to the composition lacking the triglyceride viscosity reducing agent (triangles).

Example 10

Polymer Compositions Comprising Bupivacaine and Meloxicam and a Viscosity Reducing Agent Compositions containing between approximately 40% to 60% polyorthoester of Formula I, between approximately 3% and 10% of a polar aprotic solvent (NMP or DMSO), 2.5% to 5.0% bupivacaine, and 0.075% to 0.15% meloxicam were prepared. The compositions were prepared by dissolving bupivacaine into the aprotic solvent at approximately 80° C. and mixing until dissolved. Maleic acid was then added and dissolved, followed by the addition of meloxicam, with continued mixing until dissolved, to form a drug solution. Separately, the polymer and triacetin (glycerol triacetate) were combined and heated to 70° C. then thoroughly mixed. The drug solution was then combined with the polymer and triacetin blend at an elevated temperature and mixed until homogeneous. Viscosity of the compositions was measured as set forth in the Methods section above. Exemplary compositions are presented in Table 10-1.

TABLE 10-1

| Composition # | Wt % Bupivacaine | Wt % Meloxicam | Wt % Maleic Acid | Wt % POE | Wt % Solvent | Wt % Triacetin | Viscosity mPa-s (25° C.) |
|---|---|---|---|---|---|---|---|
| 8026-10-01 | 2.5% | 0.075% | 0.15% | 54.2 | 3% NMP | 40% | 3890 |
| 8026-10-02 | 2.5% | 0.075% | 0.10% | 52.3 | 5% DMSO | 40% | 2006 |
| 8026-10-03 | 2.5% | 0.15% | 0.15% | 54.2% | 8% DMSO | 35% | 2876 |
| 8026-10-04 | 5.0% | 0.15% | 0.15% | 49.7% | 10% DMSO | 35% | 1794 |
| 8026-10-05 | 2.5% | 0.15% | 0.15% | 57.2% | 10% DMSO | 30% | 4522 |
| 8026-10-06 | 2.5% | 0.075% | 0.15% | 54.3% | 8% DMSO | 35% | 3105 |
| 8026-10-07 | 2.5% | 0.075% | 0.075% | 57.35% | 10% DMSO | 30% | 3131 |
| 8026-10-08 | 2.5% | 0.075% | 0.05% | 62.38% | 10% DMSO | 25% | 8519 |
| 8026-10-09 | 5.0% | 0.15% | 0.4% | 59.45% | 10% DMSO | 25% | N/A |
| 8026-10-10 | 5.0% | 0.15% | 0.4% | 53.10% | 10% DMSO | 30% | 4876 |

The addition of the triglyceride viscosity reducing agent triacetin to these compositions decreased the viscosity at least 10-fold, at least 20-fold, or at least 40-fold, or more, as compared to compositions with no triglyceride viscosity reducing agent.

Example 11

In Vitro Release of Bupivacaine and Meloxicam from Compositions Comprising a Triglyceride Viscosity Reducing Agent The release of bupivacaine and meloxicam from the compositions of Example 10 was determined by placing 100 mg of the polymer composition (approximately 50 mg to 200 mg) into vials containing 200 mL of phosphate buffered saline. The vials were incubated at 37° C. on a shaker at 60 RPM. At 24 hour intervals, 1 mL samples were taken from the vials without any agitation of the solution. Each sample was analyzed by HPLC to determine the concentration of bupivacaine and meloxicam. The cumulative drug release from the depot was then calculated and is shown in Tables 11-1 and 11-2.

TABLE 11-1

In Vitro Release of Bupivacaine

| Composition # | Percent Bupivacaine Released for Compositions | | |
|---|---|---|---|
| | 24 hrs | 48 hrs | 72 hrs |
| 8026-10-01 | 29.13% | 58.94% | 75.66% |
| 8026-10-02 | 24.48% | 45.16% | 76.25% |
| 8026-10-03 | 28.92% | 51.95% | 74.48% |
| 8026-10-04 | 8.06% | 24.21% | 46.55% |
| 8026-10-05 | 20.08% | 47.04% | 70.51% |
| 8026-10-07 | 25.51% | 55.48% | 72.66% |
| 8026-10-08 | 16.60% | 44.00% | 63.90% |
| 8026-10-10 | 22.83% | 47.25% | 74.02% |

TABLE 11-2

In Vitro Release of Meloxicam

| Composition # | Percent Meloxicam Released for Compositions | | |
|---|---|---|---|
| | 24 hrs | 48 hrs | 72 hrs |
| 8026-10-01 | 37.30% | 64.83% | 91.20% |
| 8026-10-02 | 28.86% | 51.79% | 84.05% |
| 8026-10-03 | 41.52% | 74.59% | 99.35% |
| 8026-10-04 | 9.44% | 33.17% | 57.59% |
| 8026-10-05 | 30.30% | 67.09% | 89.30% |
| 8026-10-07 | 41.37% | 70.87% | 83.86% |
| 8026-10-08 | 33.60% | 58.40% | 76.70% |
| 8026-10-10 | 20.63% | 44.18% | 66.71% |

Example 12

In Vivo Analysis of Delivery Systems Comprising Bupivacaine and Meloxicam and a Triglyceride Viscosity Reducing Agent An in vivo pharmacokinetic study was conducted as follows. Beagles (n=5) weighing approximately 10 kg received 2 mL of composition identified nos. 8026-10-03 and 8026-10-05 in two separate injections of approximately 1 mL each. Plasma samples were collected from each dog at the following time points: t=0, (immediately prior to drug administration), 0.5, 1, 3, 6, 24, and daily up to day 5 (120 hrs). The plasma samples were subsequently analyzed by LC/MS/MS for bupivacaine and meloxicam.

The data from the study is shown in FIGS. 7A-7B. The compositions provided measurable plasma concentrations of bupivacaine (FIG. 7A) and meloxicam (FIG. 7B) over a period of at least 96 hours following administration, where the composition with 35 wt % triacetin (8026-10-03) is indicated by the triangles and the composition with 30 wt % triacetin (8026-10-05) is represented by the open circles.

Example 13

In Vivo Use of the Compositions as a Nerve Block

A study was performed to determine if the combination of an amide-type local anesthetic such as bupivacaine and an NSAID as described herein could be used for local anesthesia by way of a nerve block procedure. In order to conduct a perineural injection, the lower viscosity formulations, such as those described in Example 10, were evaluated.

The efficacy of the compositions were tested using the Von Frey assay, however, in these studies, as compared to the postoperative pain studies, no incisions were made. Four grams of each composition were injected into each of 4 animals and administered so as to be near the sciatic nerve in one flank of the pig. Table 13-1 below provides a summary of the compositions injected to each animal.

TABLE 13-1

| Group # | Composition # | Wt % Bupivacaine | Wt % Meloxicam | Wt % Maleic Acid | Wt % POE | Solvent Wt % | Wt % Triacetin |
|---|---|---|---|---|---|---|---|
| 1 | Saline | — | — | — | — | — | — |
| 2 | Bupivacaine Injection (5 mL) | 0.5% | — | — | — | — | — |
| 3 | 8026-10-01 | 2.5% | 0.075% | 0.15% | 54.20% | NMP 3% | 40% |
| 4 | 8026-13-01 | 2.5% | N/A | 0.10% | 54.35% | NMP 3% | 40% |
| 5 | 8026-10-02 | 2.5% | 0.075% | 0.10% | 52.33% | DMSO 5% | 40% |

Nerve Block Assessment: To assess the degree of nerve block, Von Frey filaments (Ugo Basile) are applied at the dorsal source surface of the foot. As the gram number of filaments increases, the force on the dorsal foot skin increases. The maximum force is 300 g. Filaments are applied until the animal withdraws from the stimuli. Each filament is applied 3-5 times. If withdrawal is not achieved, a thicker filament is applied. If a withdrawal is achieved, a thinner filament is applied (thicker or thinner refers to higher/thicker or lower/thinner gram force). By alternating the filament thickness, the force required to achieve withdrawal reaction is determined and recorded. Withdrawal reaction is considered as the act of lifting the leg and moving away from the stimuli.

The results of the Von Frey assay are presented in FIG. 8, where withdrawal force, in gram force, is shown as a function of time, in hours and days, after administration in vivo to pigs of compositions comprised of a polyorthoester delivery vehicle, 2.5 wt % bupivacaine alone (Group 4, 8026-13-01, vertical dashes fill) or 2.5 wt % bupivacaine, 0.075 wt % meloxicam and 0.15% maleic acid (Group 3, 8026-10-01, no fill, open bars) or 0.10 wt % maleic acid (Group 5, 8026-10-02, horizontal line fill), or a buffered solution of 0.5 wt % bupivacaine (vertical line fill, Group 2); bars with dotted fill represent the response for the control group treated with saline.

Example 14

Preparation of Compositions Comprising Granisetron and a Triglyceride Viscosity Reducing Agent Compositions containing between approximately 65 wt % to 88 wt % polyorthoester of Formula I, between approximately 5 wt % and 10 wt % of an polar aprotic solvent (NMP or DMSO), between approximately 0 wt % and 20 wt % triacetin, and approximately 2 wt % granisetron were prepared. The compositions were prepared by adding the granisetron into an aprotic solvent at approximately 80° C. mixing until dissolved to form a drug solution. Separately, the polymer and triacetin (glycerol triacetate) were combined and heated to 70° C. followed by thorough mixing. The drug solution was then combined with the polymer and triacetin blend at 70° C. and mixed until homogeneous. For comparison, a granisetron formulation consisting of 15% of a polar aprotic solvent was prepared.

Viscosity of the compositions was measured at 25° C. and at 37° C. using the method set forth in the Methods section above. Results are shown in Table 14-1. The addition of triacetin to the compositions decreased the viscosity when measured at 25° C. by at least about 5 fold (compare 8026-14-06 and 8026-14-03), at least about 7-fold (compare 8016-14-01 and 8026-14-02), at least about 20 fold (compare 8026-14-04 and 8025-14-03) or at least about 90-fold (compare 8026-14-05 and 8026-14-03). The addition of triacetin to the compositions decreased the viscosity when measured at 37° C. by at least about 5 fold (compare 8026-14-01 and 8026-14-02; and 8026-14-03 and 8026-14-03), at least about 30-fold (compare 8026-14-05 and 8026-14-03).

Example 15

In Vitro Release of Compositions Comprising Granisetron and a Triglyceride Viscosity Reducing Agent The release of granisetron from the compositions of Example 14 was determined by placing 200 mg of each composition into a vial containing 150 mL of phosphate buffered saline. The samples were then incubated at 37° C. on a shaker at 60 RPM for the first 24 hours and then incubated at 50° C. for 120 hours. At 24 hour intervals, 1 mL samples were taken from the vials without any agitation of the solution. Each sample was analyzed by HPLC to determine the concentration of granisetron. The cumulative drug release from each depot was calculated and is shown in Table. 15-1.

TABLE 15-1

In Vitro Release of Granisetron

| Composition # | Percent Granisetron Released | | | |
|---|---|---|---|---|
| | 24 hrs | 48 hrs | 72 hrs | 96 hrs |
| 8026-14-01 | 4.10% | 13.7% | 46.0% | 91.1% |
| 8026-14-02 | 5.90% | 20.6% | 43.2% | 77.5% |
| 8026-14-03 | 6.50% | 28.2% | 52.7% | 81.2% |
| 8026-14-04 | 6.80% | 34.6% | 57.9% | 88.8% |
| 8026-14-05 | 17.50% | 54.7% | 70.8% | 86.6% |
| 8026-14-06 | 6.60% | 31.7% | 58.4% | 79.9% |
| 8026-14-08 | 10.4% | 46.6% | 80.9% | 101.3 |

The compositions provided release of granisetron for at least about 3 days or at least about 4 days. The addition of triacetin to reduce viscosity of the compositions did not alter the in vitro release of granisetron relative to a similar composition lacking triacetin, as seen when comparing composition number 8026-14-03, with no triacetin, and 8026-14-04, with 10% triacetin. Release of granisetron from the triacetin composition (which had a 17 fold lower viscosity at 25° C.) was within 10% of the granisetron cumulative release provided by a similar composition lacking the triacetin. Similarly, a comparison of 8026-14-01 (with no triacetin) and 8026-14-02 (with 10 wt % triacetin) reveals that the triacetin-containing composition with a 7-fold lower viscosity at 25° C. released granisetron at a rate within about

TABLE 14-1

| Formulation ID | Wt % Granisetron | Wt % POE | Solvent Wt % | Triacetin Wt % | Viscosity 25° C. (mPa-s) | Viscosity 37° C. (mPa-s) |
|---|---|---|---|---|---|---|
| 8026-14-01 | 2.00% | 88.00% | DMSO 10.00% | 0.00% | 672,242 | 149,401 |
| 8026-14-02 | 2.00% | 78.00% | DMSO 10.00% | 10.00% | 93,506 | 35,228 |
| 8026-14-03 | 2.00% | 93.00% | NMP 5.00% | 0.00% | 5,712,695 | 490,174 |
| 8026-14-04 | 2.00% | 78.00% | NMP 5.00% | 10.00% | 330,859 | 78,205 |
| 8026-14-05 | 2.00% | 73.00% | NMP 5.00% | 20.00% | 62,520 | 17,745 |
| 8026-14-06 | 2.00% | 88.00% | NMP 5.00% | 5.00% | 1,028,656 | 192,472 |
| 8026-14-07 | 2.00% | 78.00% | NMP 5.00% | 15.00% | 120,342 | 31,592 |
| 8026-14-08 | 2.00% | 83.00% | NMP 15.00% | 0.00% | 90,232 | 26,202 |

15% of the release provided by the composition with no triacetin at the 24 hour, 72 hour and 96 hour time points.

It is claimed:

1. A delivery system for administration to a subject, the delivery system comprising:
   40 wt % to 75 wt % of a polyorthoester;
   3 wt % to 25 wt % dimethyl sulfoxide;
   10 wt % to 35 wt % triacetin;
   2 wt % to 5 wt % bupivacaine; and
   0.01 wt % to 1 wt % meloxicam;
wherein the polyorthoester is represented by the structure shown as Formula I:

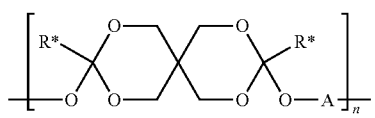

where
   R* is $C_{1-4}$ alkyl,
   n ranges from 5 to 400, and
   A is a diol; where A is $R^1$ and/or $R^3$, where the fraction of A units that are of formula $R^1$ is between 0 and 25 mole percent, where
when $R^3$ is

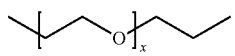

where x is 2; and
when $R^1$ is

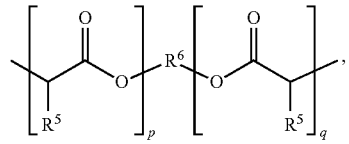

$R^5$ is H, and $R^6$ is

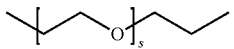

the sum of p and q is, on average, 2 and s is 2.

2. The delivery system of claim 1, wherein the delivery system has a viscosity less than 10000 mPa-s when measured at 37° C. using a viscometer.

3. The delivery system of claim 1, wherein the fraction of A units that are of formula $R^1$ is about 20 mole percent.

4. The delivery system of claim 1, wherein the polyorthoester has a weight average molecular weight between 2,500 daltons and 10,000 daltons.

5. The delivery system of claim 1, wherein the bupivacaine and the meloxicam are solubilized in a single phase.

6. The delivery system of claim 1, wherein the delivery system is an extended-release composition.

7. The delivery system of claim 1, further comprising maleic acid.

8. A method for providing analgesia or pain relief to a subject in need thereof, comprising: administering to the subject the delivery system according to claim 1.

9. The method of claim 8, wherein the delivery system is administered as a nerve block.

10. The method of claim 8, wherein the delivery system is administered as a peripheral nerve block.

11. The method of claim 8, wherein the delivery system is administered to a surgical wound.

12. The method according to claim 8, wherein the pain is post-operative pain.

13. A method for prophylactic treatment of pain in a subject, comprising: administering to the subject the delivery system according to claim 1.

14. The delivery system of claim 1, wherein the polyorthoester comprises the unit

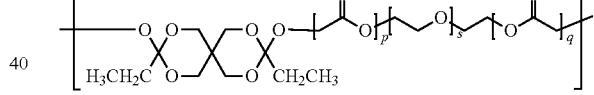

* * * * *